(12) United States Patent
Amundson et al.

(10) Patent No.: US 7,914,891 B2
(45) Date of Patent: Mar. 29, 2011

(54) WIPES INCLUDING MICROENCAPSULATED DELIVERY VEHICLES AND PHASE CHANGE MATERIALS

(75) Inventors: John David Amundson, Greenville, WI (US); Alan Edward Wright, Woodstock, GA (US); Frank P. Abuto, Duluth, GA (US); Michael S. Brunner, Roswell, GA (US); Wael R. Joseph, Appleton, WI (US); Larry E. Brown, Appleton, WI (US); David Charles Musil, Appleton, WI (US); Michael Allen Daley, Appleton, WI (US); Jeffrey David Shelley, Atlanta, GA (US); Brian Patrick Argo, Hortonville, WI (US); David J. Drath, Lakeland, MN (US); William A. Hendrickson, Stillwater, MN (US); Hal Arthur LaFleur, III, Maplewood, MN (US); Duane G. Krzysik, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/320,363

(22) Filed: Dec. 28, 2005

(65) Prior Publication Data
US 2007/0148447 A1 Jun. 28, 2007

(51) Int. Cl.
*B32B 33/00* (2006.01)
*B32B 5/02* (2006.01)
(52) U.S. Cl. .................... 428/402; 428/40.2; 428/402.2; 428/402.24; 428/402.21; 428/402.22
(58) Field of Classification Search .................. 428/40.2, 428/402.2, 402.21, 402.22, 402.24
See application file for complete search history.

(56) References Cited

U.S. PATENT DOCUMENTS

| | | | |
|---|---|---|---|
| 1,312,449 | A | 8/1919 | Lundberg |
| 2,766,478 | A | 10/1956 | Raley, Jr. et al. |
| 2,789,725 | A | 4/1957 | Carper |
| 3,016,308 | A | 1/1962 | Macaulay |
| 3,084,664 | A | 4/1963 | Solomon et al. |
| 3,175,558 | A | 3/1965 | Caillonette et al. |
| 3,199,490 | A | 8/1965 | Karlik |
| 3,261,347 | A | 7/1966 | Sherman |
| 3,310,353 | A | 3/1967 | Cordis |
| 3,363,604 | A | 1/1968 | Pschibul |

(Continued)

FOREIGN PATENT DOCUMENTS

CA 2346223 A 8/2001

(Continued)

OTHER PUBLICATIONS

International Search Report and Written Opinion from PCT/US2006/042050, dated May 2, 2007.

(Continued)

*Primary Examiner* — D. Lawrence Tarazano
*Assistant Examiner* — Matthew D Matzek
(74) *Attorney, Agent, or Firm* — Armstrong Teasdale LLP

(57) ABSTRACT

Microencapsulated delivery vehicles comprising an active agent are disclosed. In one embodiment, the microencapsulated delivery vehicles are heat delivery vehicles capable of generating heat upon activation. The microencapsulated heat delivery vehicles may be introduced into wet wipes such that, upon activation, the wet wipe solution is warmed resulting in a warm sensation on a user's skin. Any number of other active ingredients, such as cooling agents and biocides, can also be incorporated into a microencapsulated delivery vehicle.

14 Claims, 24 Drawing Sheets

U.S. PATENT DOCUMENTS

| | | | |
|---|---|---|---|
| 3,388,953 A | 6/1968 | Browning |
| 3,429,827 A | 2/1969 | Ruus |
| 3,441,353 A | 4/1969 | Claff |
| 3,464,413 A | 9/1969 | Goldfarb et al. |
| 3,472,675 A | 10/1969 | Gordon et al. |
| 3,516,941 A | 6/1970 | Matson |
| 3,585,982 A | 6/1971 | Hollinshead |
| 3,638,786 A | 2/1972 | Borecki et al. |
| 3,674,176 A | 7/1972 | Sagi |
| 3,676,190 A | 7/1972 | Lander et al. |
| 3,691,090 A | 9/1972 | Kitajima et al. |
| 3,691,270 A | 9/1972 | Charle et al. |
| 3,707,945 A | 1/1973 | Boone |
| 3,738,857 A | 6/1973 | Brockett et al. |
| 3,756,483 A | 9/1973 | Schraeder |
| 3,804,061 A | 4/1974 | Cassar et al. |
| 3,839,220 A | 10/1974 | Barchas |
| 3,849,241 A | 11/1974 | Butin et al. |
| 3,854,624 A | 12/1974 | Canci |
| 3,862,715 A | 1/1975 | Remenyik |
| 3,865,271 A | 2/1975 | Gold |
| 3,889,804 A | 6/1975 | Ravich |
| 3,936,573 A | 2/1976 | Brockett |
| 3,947,571 A | 3/1976 | Murphy et al. |
| 3,980,203 A | 9/1976 | Dearling |
| 3,982,659 A | 9/1976 | Ross |
| 3,994,417 A | 11/1976 | Boedecker |
| 4,004,711 A | 1/1977 | Ravich |
| 4,036,301 A | 7/1977 | Powers et al. |
| 4,041,900 A | 8/1977 | Charles |
| 4,077,390 A | 3/1978 | Stanley et al. |
| 4,088,751 A | 5/1978 | Kenkare et al. |
| 4,100,324 A | 7/1978 | Anderson et al. |
| 4,106,433 A | 8/1978 | Fernando et al. |
| 4,106,616 A | 8/1978 | Boone |
| 4,132,771 A | 1/1979 | Schreiber et al. |
| 4,159,316 A | 6/1979 | Januszewski et al. |
| 4,187,287 A | 2/1980 | Schreiber et al. |
| 4,362,715 A | 12/1982 | Strianse et al. |
| 4,375,448 A | 3/1983 | Appel et al. |
| 4,379,143 A | 4/1983 | Sherry et al. |
| 4,407,957 A | 10/1983 | Lim |
| 4,436,224 A | 3/1984 | McInery |
| 4,460,563 A | 7/1984 | Calanchi |
| 4,504,402 A | 3/1985 | Chen |
| 4,505,953 A | 3/1985 | Chen |
| 4,513,053 A | 4/1985 | Chen |
| 4,514,461 A | 4/1985 | Woo |
| 4,516,564 A | 5/1985 | Koiso et al. |
| 4,568,559 A | 2/1986 | Nuwayser et al. |
| 4,598,664 A | 7/1986 | Hamlin |
| 4,620,502 A | 11/1986 | Kimble |
| 4,626,550 A | 12/1986 | Hertzenberg |
| 4,667,846 A | 5/1987 | Marceau |
| 4,747,365 A | 5/1988 | Tusch |
| 4,756,299 A | 7/1988 | Podella |
| 4,798,691 A | 1/1989 | Kasai et al. |
| 4,853,266 A | 8/1989 | Cullen |
| 4,872,442 A | 10/1989 | Manker |
| 4,880,953 A | 11/1989 | Manker |
| 4,904,524 A | 2/1990 | Yoh |
| 4,923,645 A * | 5/1990 | Tsang et al. ................. 264/4.3 |
| 4,964,543 A | 10/1990 | Scheiber |
| 4,978,560 A | 12/1990 | Stone |
| 4,984,530 A | 1/1991 | Dutton |
| 4,991,538 A | 2/1991 | Davids et al. |
| 5,035,321 A | 7/1991 | Denton |
| 5,045,569 A | 9/1991 | Delgado |
| 5,071,706 A | 12/1991 | Soper |
| 5,107,734 A | 4/1992 | Armbruster |
| 5,156,885 A | 10/1992 | Budd |
| 5,180,637 A | 1/1993 | Sumii |
| 5,184,613 A | 2/1993 | Mintz |
| 5,187,011 A | 2/1993 | Manalastas |
| 5,192,615 A | 3/1993 | McDougall |
| 5,194,356 A | 3/1993 | Sacripante et al. |
| 5,204,183 A | 4/1993 | McDougall |
| 5,232,769 A | 8/1993 | Yamato et al. |
| 5,265,509 A | 11/1993 | Chen |
| 5,284,703 A | 2/1994 | Everhart et al. |
| 5,339,796 A | 8/1994 | Manker |
| 5,350,624 A | 9/1994 | Georger et al. |
| 5,366,801 A | 11/1994 | Bryant et al. |
| 5,375,616 A | 12/1994 | Chen |
| 5,385,737 A | 1/1995 | Shigeno et al. |
| 5,392,945 A | 2/1995 | Syrek |
| 5,415,222 A | 5/1995 | Colvin et al. |
| 5,418,062 A | 5/1995 | Budd |
| 5,425,975 A | 6/1995 | Koiso et al. |
| 5,435,465 A | 7/1995 | El-Amin |
| 5,439,104 A | 8/1995 | Wolska-Klis |
| 5,443,084 A | 8/1995 | Saleur |
| 5,462,197 A | 10/1995 | Pound |
| 5,484,895 A | 1/1996 | Meister et al. |
| 5,507,389 A | 4/1996 | Syrek |
| 5,538,531 A | 7/1996 | Hudson et al. |
| 5,589,194 A | 12/1996 | Tsuei et al. |
| 5,598,954 A | 2/1997 | Salzonao |
| 5,618,008 A | 4/1997 | Dearwester et al. |
| 5,624,025 A | 4/1997 | Hixon |
| 5,637,389 A | 6/1997 | Colvin et al. |
| 5,656,708 A | 8/1997 | Meister |
| 5,660,636 A | 8/1997 | Shangold et al. |
| 5,677,048 A | 10/1997 | Pushaw |
| 5,697,577 A | 12/1997 | Ogden |
| 5,712,212 A | 1/1998 | Scott et al. |
| 5,725,888 A | 3/1998 | Scott et al. |
| 5,728,454 A | 3/1998 | Inaba et al. |
| 5,733,272 A | 3/1998 | Brunner et al. |
| 5,738,082 A | 4/1998 | Page et al. |
| 5,747,004 A | 5/1998 | Giani et al. |
| 5,762,710 A | 6/1998 | Ngai et al. |
| 5,780,047 A | 7/1998 | Kamiya et al. |
| 5,785,179 A | 7/1998 | Buczwinski et al. |
| 5,819,989 A | 10/1998 | Saraceni |
| 5,839,608 A | 11/1998 | Gillberg-LaForce |
| 5,887,759 A | 3/1999 | Ayigbe |
| 5,944,709 A | 8/1999 | Barney et al. |
| 5,951,762 A | 9/1999 | Shangold et al. |
| 5,975,074 A | 11/1999 | Koiso et al. |
| 6,021,920 A | 2/2000 | Aldape |
| 6,057,372 A | 5/2000 | Nobuhiro |
| 6,059,882 A | 5/2000 | Steinhardt et al. |
| 6,063,406 A | 5/2000 | Hornack |
| 6,085,899 A | 7/2000 | Thorsbakken |
| 6,099,555 A | 8/2000 | Sabin |
| 6,121,165 A | 9/2000 | Mackey et al. |
| 6,127,294 A | 10/2000 | Koiso et al. |
| 6,170,426 B1 | 1/2001 | Thorsbakken |
| 6,171,647 B1 | 1/2001 | Holman |
| 6,180,124 B1 | 1/2001 | Ohta et al. |
| 6,207,738 B1 | 3/2001 | Zuckerman et al. |
| 6,213,424 B1 | 4/2001 | Helfer-Grand |
| 6,216,920 B1 | 4/2001 | Baggett |
| 6,217,889 B1 | 4/2001 | Lorenzi et al. |
| 6,238,682 B1 | 5/2001 | Klofta et al. |
| 6,267,975 B1 | 7/2001 | Smith, III et al. |
| 6,269,969 B1 | 8/2001 | Huang et al. |
| 6,287,580 B1 | 9/2001 | Gott et al. |
| 6,314,971 B1 | 11/2001 | Schneider |
| 6,319,318 B1 | 11/2001 | Pekarek et al. |
| 6,321,937 B1 | 11/2001 | Desimone et al. |
| 6,322,801 B1 | 11/2001 | Lorenzi et al. |
| 6,343,491 B1 | 2/2002 | Jung |
| 6,346,153 B1 | 2/2002 | Lake et al. |
| 6,355,281 B1 | 3/2002 | Cerchiari et al. |
| 6,387,385 B1 | 5/2002 | Wang |
| 6,401,968 B1 | 6/2002 | Huang et al. |
| 6,431,111 B1 | 8/2002 | Zhang |
| 6,436,128 B1 | 8/2002 | Usui |
| 6,457,434 B1 | 10/2002 | Lazar |
| 6,484,514 B1 | 11/2002 | Joseph et al. |
| 6,503,976 B2 | 1/2003 | Zuckerman et al. |
| 6,514,362 B1 | 2/2003 | Zuckerman et al. |
| 6,520,942 B1 | 2/2003 | Putman |
| 6,528,766 B1 | 3/2003 | Parks et al. |
| 6,547,063 B1 | 4/2003 | Zaveri et al. |

| | | |
|---|---|---|
| 6,547,881 B1 | 4/2003 | Klackner |
| 6,550,633 B2 | 4/2003 | Huang et al. |
| 6,562,318 B1 | 5/2003 | Filler |
| 6,579,570 B1 | 6/2003 | Lang et al. |
| 6,592,004 B2 | 7/2003 | Huang et al. |
| 6,601,737 B1 | 8/2003 | Sandler |
| 6,613,144 B1 | 9/2003 | Loertscher et al. |
| 6,663,686 B1 | 12/2003 | Geiger et al. |
| 6,673,358 B1 | 1/2004 | Cole et al. |
| 6,680,084 B1 | 1/2004 | Chtourou |
| 6,708,845 B2 | 3/2004 | Weng |
| 6,726,386 B1 | 4/2004 | Gruenbacher et al. |
| 6,742,689 B2 | 6/2004 | Formon et al. |
| 6,749,148 B2 | 6/2004 | Helfer-Grand |
| 6,752,998 B2 | 6/2004 | Verdrel-Lahaxe et al. |
| 6,766,919 B2 | 7/2004 | Huang et al. |
| 6,831,051 B2 | 12/2004 | Sommerville-Roberts et al. |
| 6,838,154 B1 | 1/2005 | Varona et al. |
| 6,847,011 B2 | 1/2005 | McConnell et al. |
| 6,858,666 B2 | 2/2005 | Hamer et al. |
| 6,863,682 B2 | 3/2005 | Usui |
| 6,890,553 B1 | 5/2005 | Sun et al. |
| 6,890,592 B2 | 5/2005 | Seehafer et al. |
| 6,903,307 B1 | 6/2005 | McConnell et al. |
| 6,918,513 B1 | 7/2005 | Downey |
| 6,946,413 B2 | 9/2005 | Lange et al. |
| 6,952,849 B2 | 10/2005 | Pacella |
| 6,958,103 B2 | 10/2005 | Anderson et al. |
| 7,021,848 B1 | 4/2006 | Gruenbacher et al. |
| 7,101,612 B2 | 9/2006 | Lang et al. |
| 7,108,440 B1 | 9/2006 | Gruenbacher et al. |
| 7,211,249 B2 | 5/2007 | Schnittger et al. |
| 7,229,611 B2 | 6/2007 | Zamudio-Tena et al. |
| 7,238,655 B2 | 7/2007 | Ness |
| 2002/0044968 A1 | 4/2002 | van Lengerich |
| 2002/0050659 A1 | 5/2002 | Toreki et al. |
| 2002/0061954 A1 | 5/2002 | Davis et al. |
| 2002/0086045 A1 | 7/2002 | Wang |
| 2002/0102488 A1 | 8/2002 | Yanaka et al. |
| 2002/0155281 A1 | 10/2002 | Lang et al. |
| 2002/0174863 A1 | 11/2002 | Saric et al. |
| 2002/0192268 A1 | 12/2002 | Alwattari et al. |
| 2003/0082217 A1* | 5/2003 | Afriat et al. ............ 424/401 |
| 2003/0084914 A1 | 5/2003 | Simon |
| 2003/0105192 A1 | 6/2003 | Li et al. |
| 2003/0118779 A1 | 6/2003 | Fish et al. |
| 2003/0175517 A1 | 9/2003 | Voigt et al. |
| 2003/0198652 A1 | 10/2003 | Shefer et al. |
| 2003/0228351 A1 | 12/2003 | Hasenoehrl et al. |
| 2003/0232090 A1 | 12/2003 | Ahmad et al. |
| 2004/0062732 A1 | 4/2004 | Friscia et al. |
| 2004/0062735 A1 | 4/2004 | Sun et al. |
| 2004/0063603 A1 | 4/2004 | Dave et al. |
| 2004/0069298 A1 | 4/2004 | Minami |
| 2004/0084791 A1 | 5/2004 | Han et al. |
| 2004/0116017 A1 | 6/2004 | Smith, III et al. |
| 2004/0118862 A1 | 6/2004 | Amundson |
| 2004/0121072 A1 | 6/2004 | Xing et al. |
| 2004/0147189 A1 | 7/2004 | Smith, III et al. |
| 2004/0164085 A1 | 8/2004 | Kitching et al. |
| 2004/0169299 A1 | 9/2004 | Davis et al. |
| 2004/0185023 A1 | 9/2004 | Schnittger et al. |
| 2004/0265589 A1 | 12/2004 | Yamada et al. |
| 2005/0048090 A1 | 3/2005 | Rau |
| 2005/0053647 A1 | 3/2005 | Matusch et al. |
| 2005/0067423 A1 | 3/2005 | Cho |
| 2005/0067726 A1 | 3/2005 | Yan et al. |
| 2005/0113771 A1 | 5/2005 | MacDonald et al. |
| 2005/0136765 A1* | 6/2005 | Shannon ............ 442/123 |
| 2005/0158395 A1 | 7/2005 | Zimmermann et al. |
| 2005/0169868 A1 | 8/2005 | Mohammadi et al. |
| 2005/0214242 A1 | 9/2005 | Mohammadi et al. |
| 2005/0226834 A1 | 10/2005 | Lambino et al. |
| 2005/0250169 A1 | 11/2005 | Gonzalez et al. |
| 2006/0018953 A1 | 1/2006 | Guillon et al. |
| 2006/0159776 A1 | 7/2006 | Ward |
| 2006/0173576 A1 | 8/2006 | Goerg et al. |
| 2006/0270585 A1 | 11/2006 | Jordan, IV et al. |
| 2006/0270586 A1 | 11/2006 | Jordan, IV et al. |
| 2006/0276356 A1 | 12/2006 | Panandiker et al. |
| 2007/0027415 A1 | 2/2007 | Kopreski |

FOREIGN PATENT DOCUMENTS

| | | |
|---|---|---|
| DE | 2 912 972 C2 | 8/1982 |
| DE | 3 101 471 A1 | 8/1982 |
| DE | 3447833 A1 | 7/1986 |
| DE | 35 35 330 A1 | 4/1987 |
| DE | 3 922 159 A1 | 1/1991 |
| DE | 29809967 U1 | 10/1998 |
| DE | 197 16 254 A1 | 1/1999 |
| DE | 19846375 A1 | 4/2000 |
| DE | 199 20 685 A1 | 11/2000 |
| DE | 199 37 884 A1 | 2/2001 |
| DE | 10002590 A1 | 8/2001 |
| DE | 10009252 | 9/2001 |
| DE | 201 08 351 U1 | 10/2001 |
| DE | 1026453 A1 | 11/2001 |
| DE | 10205872 A1 | 3/2003 |
| DE | 10209111 A1 | 9/2003 |
| DE | 20305272 | 9/2003 |
| DE | 10234257 | 2/2004 |
| DE | 10361100 A1 | 1/2005 |
| DE | 102005002169 A1 | 7/2006 |
| DE | 1005042236 A | 3/2007 |
| EP | 0247864 | 12/1987 |
| EP | 0252553 B1 | 1/1988 |
| EP | 0288 909 A1 | 11/1988 |
| EP | 0351907 A2 | 1/1990 |
| EP | 0 365 160 A2 | 4/1990 |
| EP | 0370600 A1 | 5/1990 |
| EP | 0436729 | 7/1991 |
| EP | 0897719 A1 | 2/1999 |
| EP | 0 953 312 A1 | 11/1999 |
| EP | 0974340 A2 | 1/2000 |
| EP | 1038793 A1 | 9/2000 |
| EP | 1084670 A2 | 3/2001 |
| EP | 1166866 A | 1/2002 |
| EP | 1181911 A1 | 2/2002 |
| EP | 1186286 A1 | 3/2002 |
| EP | 1191092 A | 3/2002 |
| EP | 1229097 A1 | 8/2002 |
| EP | 1247568 A1 | 10/2002 |
| EP | 1310186 | 5/2003 |
| EP | 1334921 A2 | 8/2003 |
| EP | 0994650 B1 | 2/2004 |
| EP | 1402879 | 3/2004 |
| EP | 1 410 753 A1 | 4/2004 |
| EP | 1407762 | 4/2004 |
| EP | 1421872 A2 | 5/2004 |
| EP | 1051478 B1 | 11/2004 |
| EP | 1479432 A1 | 11/2004 |
| EP | 1495704 A | 1/2005 |
| EP | 1 586 308 A1 | 10/2005 |
| FR | 2 669 205 A1 | 5/1992 |
| FR | 2823137 A1 | 10/2002 |
| GB | 1291377 | 10/1972 |
| GB | 1 370 633 A | 10/1974 |
| GB | 2142135 A | 1/1985 |
| GB | 2 168 031 A | 6/1986 |
| GB | 2168031 A | 6/1986 |
| GB | 2192171 A | 1/1988 |
| GB | 2297490 A | 8/1996 |
| GB | 2394898 | 5/2004 |
| JP | 63168484 A | 6/1988 |
| JP | 02142561 A | 5/1990 |
| JP | 03152894 A | 6/1991 |
| JP | 08067869 | 3/1996 |
| JP | 08067869 A | 3/1996 |
| JP | 08112303 A | 5/1996 |
| JP | 08173471 A | 7/1996 |
| JP | 09047376 | 2/1997 |
| JP | 10077134 | 3/1998 |
| JP | 10077134 A | 3/1998 |
| JP | 2002020739 A | 1/2002 |
| JP | 2003104465 | 4/2003 |
| WO | WO 92/19141 | 11/1992 |
| WO | WO 93/04622 | 3/1993 |

| | | |
|---|---|---|
| WO | 9322961 A1 | 11/1993 |
| WO | WO 99/24159 A1 | 5/1999 |
| WO | 9937747 A1 | 7/1999 |
| WO | WO 00/43286 A1 | 7/2000 |
| WO | WO 01/03619 A1 | 1/2001 |
| WO | WO 01/06903 | 2/2001 |
| WO | WO 01/08658 A1 | 2/2001 |
| WO | WO 01/12147 A1 | 2/2001 |
| WO | WO 01/12148 A1 | 2/2001 |
| WO | WO 01/12149 A1 | 2/2001 |
| WO | WO 01/26994 A1 | 4/2001 |
| WO | WO 01/35906 A2 | 5/2001 |
| WO | WO 01/39704 A1 | 6/2001 |
| WO | WO 01/39705 A1 | 6/2001 |
| WO | WO 01/42117 | 6/2001 |
| WO | WO 01/54661 A1 | 8/2001 |
| WO | WO 01/60298 A2 | 8/2001 |
| WO | WO 01/60305 A1 | 8/2001 |
| WO | WO 01/64525 | 9/2001 |
| WO | WO 01/76439 | 10/2001 |
| WO | WO 01/89353 | 11/2001 |
| WO | WO 02/01129 A1 | 1/2002 |
| WO | WO 02/06421 A1 | 1/2002 |
| WO | 0226911 A | 4/2002 |
| WO | 03000089 | 1/2003 |
| WO | WO 03/000487 A2 | 1/2003 |
| WO | WO 03/005876 A1 | 1/2003 |
| WO | WO 03/018186 A1 | 3/2003 |
| WO | WO 03/028515 | 4/2003 |
| WO | 03048654 A | 6/2003 |
| WO | WO 03/049939 A1 | 6/2003 |
| WO | WO 03/099427 A1 | 12/2003 |
| WO | WO 2004/014540 A1 | 2/2004 |
| WO | WO 2004/016234 A1 | 2/2004 |
| WO | WO 2004/033340 A1 | 4/2004 |
| WO | 2004041251 A1 | 5/2004 |
| WO | WO 2004/041134 A1 | 5/2004 |
| WO | WO 2004/047977 A1 | 6/2004 |
| WO | WO 2004/066800 | 8/2004 |
| WO | 2004105709 A1 | 12/2004 |
| WO | WO 2004/108075 A2 | 12/2004 |
| WO | WO 2005/011855 A1 | 2/2005 |
| WO | WO 2005/011856 A1 | 2/2005 |
| WO | 2005018794 | 3/2005 |
| WO | WO 2005/018795 A1 | 3/2005 |
| WO | WO 2005/055790 | 6/2005 |
| WO | WO 2005/087068 | 9/2005 |
| WO | 2005093029 | 10/2005 |
| WO | 2007075207 A | 7/2007 |
| WO | 2007075208 A | 7/2007 |
| WO | 2007075209 A | 7/2007 |
| WO | 2007075211 A | 7/2007 |
| WO | 2007075216 A | 7/2007 |
| WO | 2007078362 A | 7/2007 |
| WO | 2007078373 | 7/2007 |
| WO | 2007078393 | 7/2007 |
| WO | 2007078400 | 7/2007 |

OTHER PUBLICATIONS

Ahlstrom, B. et al., "The Effect of Hydrocarbon Chain Length, pH, and Temperature on the Binding and Bactericidal Effect of Amphiphilic Betaine Esters on *Salmonella typhimurium*," APMIS, Mar. 1999, pp. 318-324, 107(3).

Ahlstrom, B. et al., "Loss of Bactericidal Capacity of Long-chain Quaternary Ammonium Compounds with Protein at Lowered Temperature," APMIS, Jun. 1999, pp. 606-614, 107(6).

Akiyama, H. et al, "Antimicrobial Effects of Acidic Hot-Spring Water on *Staphlyococcus aureus* Strains Isolated From Atopic Dermatitis Patients," J. Dermatol. Sci., Nov. 2000, pp. 112-118, 24(2).

Bengoechea, J. et al., "Temperature-Regulated Efflux Pump/Potassium Antiporter System Mediates Resistance to Cationic Antimicrobial Peptides in *Yersinia*," Mol. Microbiol. Jul. 2000, pp. 67-80, 37(1).

CRC Handbook of Chemistry and Physics, 72nd Ed., 1991-1992, pp. 5-83-5-90.

Del Campo, J. et al., "Antimicrobial Effect of Rosemary Extracts," J. Food Prot., Oct. 2000, pp. 1359-1368, 63(10).

Folwaczny, M. et al, "Antibacterial Effects of Pulsed Nd:YAG Laser Radiation at Different Energy Settings in Root Canals," J. Endod., Jan. 2002, pp. 24-29, 28(1).

Martinez, M. et al., "Reduced Outer Membrane Permeability of *Escherichia coli* O157:H7: Suggested Role of Modified Outer Membrane Porins and Theoretical Function in Resistance to Antimicrobial Agents," Biochemistry, Oct. 9, 2001, pp. 11965-11974, 40(40).

Moro, M. et al, "Effects of Heat Stress on the Antimicrobial Drug Resistance of *Escherichia coli* of the Intestinal Flora of Swine," J. Appl. Microbiol., May 2000, pp. 836-844, 88(5).

Niwa, M. et al, "Differential Uptake of Grepafloxacin by Human Circulating Bllod Neutrophils and Those Exudated into Tissues," Eur. J. Pharmacol., Sep. 28, 2001, pp. 121-126, 428(1).

Lange, N., Lange's Handbook of Chemistry, 11th Ed., 1793, pp. 9-107-9-115, McGraw-Hill Book Company, New York, U.S.

Raj, P., et al, "Synthesis, Microbicidal Activity, and Solution Structure of the Dodecapeptide from Bovine Neutrophils," Biopolymers, Apr. 5, 2000, pp. 281-292, 53(4).

Technical Textiles International, "Phase Change Materials Shown Potential for Medical Applications," Sep. 1999.

Yamaguchi, S., et al, "Orientation and Dynamics of an Antimicrobial Peptide in the Lipid Bilayer by Solid-State NMR Spectroscopy," Biophys. J., Oct. 2001, pp. 2203-2214, 81(4).

International Search Report from PCT/US2006/041939 dated Mar. 8, 2007.

International Search Report from PCT/US2006/038914 dated Mar. 23, 2007.

International Search Report from PCT/US2006/042435 dated Mar. 23, 2007.

International Search Report from PCT/US2006/039137 dated Mar. 23, 2007.

A.V. Patel et al., "A Novel Encapsulation Technique for the Production of Artificial Seeds," Plant cell Reports, 19: 868-874 (2000).

International Cosmetic Ingredient Dictionary and Handbook, 10th Ed., vol. 3, pp. 2294-2296 (2004).

Araki et al., "Measurements of Thermophysical Properties of Sodium Acetate Hydrate," International J. of Thermo., 16(6): 1455-1466 (1995).

K. Sturley, "Fresh Data on the Latent Heats and Heat conductivities of Some Aqua-Crystalline Compounds," J. of the Society of Chem. Industr., 51:271T-273T (Aug. 12, 1932).

Chatterji et al., "The Rate of Crystal Growth in Supersaturated Solutions, Part I," J. Indian Chem. Soc., 28(12): 599-601 (Dec. 1951).

M. Telkes, "Nucleation of Supersaturated Inorganic Salt Solutions," Industrial and Engineering Chemistry, 44/6: 1308-1310 (Jun. 1952).

Dietz, Jr. et al., "Linear Crystallization Velocities of Sodium Acetate in Supersaturated Solutions," J. Phys. Chem., 61(7): 944-948 (Jul. 1957).

Meisingset, et al., "Thermodynamic Properties and Phase Transitions of Salt Hydrates between 270 and 400 K," J. Chem. Thermodynamics, 16(1-6): 523-536 (Jan. 1984).

Wada, et al., "Heat Storage Capacity of Sodium Acetate Trihydrate during Thermal Cycling," Solar Energy, 33(3/4): 373-375 (1984).

J.C. Deelman, Mechanism of formation of Magnesite and Dolomite, Ch. 8, pp. 278-329 (2003).

Rogerson, et al., "Solidification of Heat Packs: 1. Nucleation Rate," AIChE Journal, 49(2): 505-529 (Feb. 2003).

Non-final Office Action for U.S. Appl. No. 11/320,369 dated Jul. 3, 2007.

Non-final Office Action for U.S. Appl. No. 11/319,856 dated Jul. 2, 2007.

International Search Report for PCT/US2006/039138 dated Feb. 16, 2007.

International Search Report and Written Opinion from PCT/US2006/038834, dated Apr. 11, 2007.

International Search Report and Written Opinion from PCT/US2006/038915, dated Apr. 5, 2007.

International Search Report for PCT/US2006/038271 dated May 3, 2007.

International Search Report and Written Opinion from PCT/IB2007/051684, dated Nov. 27, 2007.

Nonfinal Office Action dated Jan. 10, 2008 regarding U.S. Appl. No. 11/747,036, 7 pages.

Final Office Action dated Jan. 25, 2008 regarding U.S. Appl. No. 11/320,369, 16 pages.

Office Action dated Oct. 1, 2007 regarding U.S. Appl. No. 11/319,881, 9 pages.

Griffin, "Classification of Surface-Active Agents by 'HLB,'" Journal of the Society of Cosmetic Chemists, vol. 1, pp. 311-326, 1949.

Rosen, Delivery System Handbook for Personal Care and Cosmetic Products—Technology, Applications and Formulations, 2005, William Andrew Publishing, pp. 259-263, online version available at http://www.knovel.com/knovel2/Toc.jsp?BookID=1280 &VerticalID=0.

Nonfinal Office action from U.S. Appl. No. 11/319,953, dated Nov. 19, 2007.

International Search Report and Written Opinion regarding PCT/IB2007/051691, 24 pages (Nov. 27, 2007).

International Search Report and Written Opinion from PCT/IB2007/051671, dated Nov. 27, 2007.

International Search Report and Written Opinion regarding PCT/IB2007/054642, dated Jun. 3, 2008.

Office action from U.S. Appl. No. 11/319,953, dated May 1, 2008.

International Search Report and Written Opinion regarding PCT/IB2007/054644, dated May 21, 2008.

International Search Report and Written Opinion regarding PCT/IB2007/054645, dated May 20, 2008.

International Search Report and Written Opinion regarding PCT/IB2007/054643, dated Jul. 2, 2008.

Office Action dated Mar. 18, 2008 regarding U.S. Appl. No. 11/420,993, 7 pages.

Office Action regarding U.S. Appl. No. 11/319,953, dated Dec. 12, 2008.

Office Action regarding U.S. Appl. No. 11/610,970, dated Dec. 26, 2008.

Non-final Office Action, Jul. 8, 2008 (U.S. Appl. No. 11/320,369) 13 pages.

Non-final Office Action U.S. Appl. No. 11/420,988, (Aug. 22, 2008).

Non-final Office Action regarding U.S. Appl. No. 11/319,881, dated Aug. 20, 2008.

Non-final Office Action regarding U.S. Appl. No. 11/420,980, dated Sep. 25, 2008.

Non-final Office Action regarding U.S. Appl. No. 11/319,881, dated Feb. 6, 2009.

Non-final Office Action regarding U.S. Appl. No. 12/174,459, dated Feb. 5, 2009.

Non-final Office Action regarding U.S. Appl. No. 11/610,980, dated Feb. 26, 2009.

Non-final Office Action, U.S. Appl. No. 11/420,988 (Feb. 25, 2009).

Non-final Office Action, U.S. Appl. No. 11/609,701 (Apr. 2, 2009).

Non-final Office Action, U.S. Appl. No. 11/319,853 (Apr. 1, 2009).

Non-final Office Action, U.S. Appl. No. 11/320,247 (Apr. 3, 2009).

Final Office Action regarding U.S. Appl. No. 11/319,953, dated Apr. 28, 2009.

Office Action dated Mar. 20, 2008 regarding U.S. Appl. No. 11/319,881.

Non-final Office Action from U.S. Appl. No. 11/320,049, dated May 4, 2009.

Non-final Office Action regarding U.S. Appl. No. 11/320,369, (Jan. 27, 2009).

Non-final Office Action, U.S. Appl. No. 11/420,980 (Mar. 12, 2009).

Non-final Office Action from U.S. Appl. No. 11/610,985, dated Jun. 8, 2009.

Final Office Action regarding U.S. Appl. No. 11/610,966, dated Aug. 7, 2009.

Non-final Office Action regarding U.S. Appl. No. 11/319,953, dated Sep. 2, 2009.

Final Office Action regarding U.S. Appl. No. 11/610,980, dated Sep. 21, 2009.

Final Office Action regarding U.S. Appl. No. 12/174,459, dated Aug. 5, 2009.

Final Office Action regarding U.S. Appl. No. 11/319,881, dated Jul. 13, 2009.

Notice of Allowance regarding U.S. Appl. No. 11/420,988, dated Sep. 21, 2009.

Non-final Office Action issued in U.S. Appl. No. 11/610,985, dated Dec. 9, 2009.

Non-final Office Action issued in U.S. Appl. No. 12/267,007, dated May 10, 2010.

Final Office Action issued in related U.S. Appl. No. 11/610,985, dated Jun. 15, 2010.

Non-final Office Action regarding U.S. Appl. No. 12/267,007, dated May 10, 2010.

Final Office action issued in U.S. Appl. No. 11/610,985 (dated Aug. 31, 2010).

* cited by examiner

WIPES INCLUDING MICROENCAPSULATED DELIVERY VEHICLES AND PHASE CHANGE MATERIALS

BACKGROUND OF THE DISCLOSURE

The present disclosure relates generally to microencapsulated delivery vehicles including an active agent and processes for producing the same, as well as products incorporating the microencapsulated delivery vehicles and processes for producing the products. More particularly, the present disclosure is directed to microencapsulated heat delivery vehicles that can be effectively utilized in a wipe or similar product such that, upon use and activation, the contents of the microencapsulated heat delivery vehicles are released and contacted with moisture, which causes a warming sensation on the skin upon product use. The microencapsulated heat delivery vehicles may include one or more moisture protective and fugitive layers to improve overall capsule performance. Additionally, the microencapsulated delivery vehicles may include other active ingredients.

Wet wipes and dry wipes and related products have been used for some time by consumers for various cleaning and wiping tasks. For example, many parents have utilized wet wipes to clean the skin of infants and toddlers before and after urination and/or defecation. Many types of wet wipes are currently commercially available for this purpose.

Today, many consumers are demanding that personal health care products, such as wet wipes, have the ability to not only provide their intended cleaning function, but also to deliver a comfort benefit to the user. In recent studies, it has been shown that baby wet wipes currently on the market are sometimes perceived to be uncomfortably cold upon application to the skin, particularly for newborns. To mitigate this problem, there have been many attempts to produce warming products to warm the wipes to comfort the wet wipe users from the inherent "chill" given off by the contact of the moistened wipes upon the skin.

These warming products are generally electrically operated and come in two distinct styles. One is an "electric blanket" style which is sized to wrap around the external surfaces of a plastic wet wipes container. The other is a self-contained plastic "appliance" style which warms the wet wipes with its internally positioned heating element. Though such currently known and available wet wipe warming products typically achieve their primary objective of warming the wet wipe prior to use, they possess certain deficiencies, which can detract from their overall utility and desirability.

Perhaps the biggest deficiency of the current wet wipe warming products is their inability to sustain the moisture content of the wet wipes. More specifically, drying of the wet wipes occurs due to heating of their moisture which accelerates dehydration. As a result, wet wipes may become dried-out and unusable.

Other complaints by wipe warmer users include discoloration of the wet wipes after heating, which appears to be inevitable because of a reaction of various chemicals in the wipes upon the application of heat. Wipe warmer users further complain about warmer inconvenience and potential electrical fire hazards, which can result with the use of electrical warming products.

Based on the foregoing, there is a need in the art for wet wipes that can produce a warming sensation just prior to, or at the point of use, without using external heating products. It would be desirable if the wet wipes could produce a warming sensation within less than about 10 seconds after activation and raise the temperature of the wet wipe solution and the wet wipe base substrate at least 20° C. or more for at least 20 seconds.

SUMMARY OF THE DISCLOSURE

The present disclosure relates to microencapsulated delivery vehicles, such as microencapsulated heat delivery vehicles or microencapsulated delivery vehicles including a cooling agent, suitable for use in personal care products, such as wet wipes, dry wipes, lotions, creams, cloths, and the like. Other active agents may also be employed in the microencapsulated delivery vehicles.

In one embodiment, the microencapsulated heat delivery vehicles, upon activation in a wet wipe, for example, can produce a warming sensation on the skin when the wet wipe is used. The microencapsulated heat delivery vehicles include a core composition comprising a matrix material, such as mineral oil, and a heating agent, such as magnesium chloride. Optionally, the core composition may also include a surfactant and a hydrophobic wax material surrounding the heating agent to improve overall performance. In some cases, the core composition of the microencapsulated heat delivery vehicle may contain a small amount of un-used encapsulating activator as described herein. The core composition and components therein are encapsulated in a thin capsule that may have one or more moisture protective layers and/or fugitive layers thereon to impart additional advantageous characteristics. Upon use in a wet wipe, the capsules containing the core composition including the matrix material and heating agent (and any other optional components) are ruptured such that the heating agent contacts water present in the wet wipe solution and releases heat to cause a warming sensation on the skin.

The present disclosure also relates to processes for manufacturing a microencapsulated delivery vehicle suitable for use in personal care products, such as wet wipes. In one embodiment, a composition including a core composition comprising a matrix material, such as mineral oil, and a heating agent that may or may not be surrounded by a hydrophobic wax material, an encapsulating activator, and optionally, a surfactant, is introduced into a liquid solution containing a crosslinkable compound. Once in the liquid solution, the encapsulating activator reacts with the crosslinkable compound to form an encapsulation layer that surrounds the core composition. After a sufficient time has passed, the encapsulated core composition containing the heating agent is removed from the liquid solution. Optionally, the encapsulated core composition may then be subjected to one or more further processing steps to introduce additional layers of encapsulation onto the formed shell. These layers may include, for example, a moisture protective layer to reduce the potential for premature heat release through deactivation of the heating agent through contact with water, and a fugitive layer to impart mechanical strength to the capsule.

The present disclosure further relates to self-warming wipes and methods of manufacturing the self-warming wipes. In one embodiment, the wipes are self-warming wet wipes. Generally, the wet wipes comprise a fibrous sheet material, a wetting solution, and a microencapsulated heat delivery vehicle that includes an encapsulation layer that surrounds a core composition including a heating agent. When the microencapsulated heat delivery vehicle is ruptured, the contents of the microencapsulated heat delivery vehicle contact the wetting solution and generate heat to create a warming sensation at the surface of the wet wipe.

The present disclosure further relates to self-warming wet wipes comprising a fibrous sheet material, a wetting solution, a heat delivery vehicle, and a first phase change material. The first phase change material present in the wet wipe is capable of providing thermal stability to the wipe and keeping the wet wipe from becoming too hot upon use.

The present disclosure further relates to cleansing compositions for use in cleaning both animate and inanimate surfaces. The cleansing compositions generally include the microencapsulated heat delivery vehicle in combination with a biocide agent. The cleansing compositions may further be incorporated in cleansing products. For example, in one embodiment, the cleansing composition is used in combination with a wet wipe. When the microencapsulated heat delivery vehicle contained in the wet wipe solution is ruptured, the contents of the microencapsulated heat delivery vehicle contact the wetting solution and generate heat, which can activate or enhance the biocidal function of the biocide agent.

As such, the present disclosure is directed to a microencapsulated heat delivery vehicle comprising a core composition surrounded by an encapsulation layer. The core composition material comprises a matrix material and a heating agent. The microencapsulated heat delivery vehicle has a diameter of from about 5 micrometers to about 5000 micrometers.

The present disclosure is further directed to a substantially fluid-impervious microencapsulated heat delivery vehicle comprising a core composition, an encapsulation layer surrounding the core composition, and a moisture protective layer surrounding the encapsulation layer. The core composition comprises a matrix material and a heating agent and the microencapsulated heat delivery vehicle has a diameter of from about 5 micrometers to about 5000 micrometers.

The present disclosure is further directed to a stabilized substantially fluid-impervious microencapsulated heat delivery vehicle comprising a core composition, an encapsulation layer surrounding the core composition, a moisture protective layer surrounding the encapsulation layer, and a fugitive layer surrounding the moisture protective layer. The core composition comprises a matrix material and a heating agent and the microencapsulated heat delivery vehicle has a diameter of from about 5 micrometers to about 5000 micrometers.

The present disclosure is further directed to a microencapsulated heat delivery vehicle comprising a core composition surrounded by an encapsulation layer. The core composition comprises a matrix material and a heating agent, and the heating agent is surrounded by a hydrophobic wax material. The microencapsulated heat delivery vehicle has a diameter of from about 5 micrometers to about 5000 micrometers.

The present disclosure is further directed to a substantially fluid-impervious microencapsulated heat delivery vehicle comprising a core composition, an encapsulation layer surrounding the core composition, and a moisture protective layer surrounding the encapsulation layer. The core composition comprises a matrix material and a heating agent, and the heating agent is surrounded by a hydrophobic wax material. The microencapsulated heat delivery vehicle has a diameter of from about 5 micrometers to about 5000 micrometers.

The present disclosure is further directed to a stabilized substantially fluid-impervious microencapsulated heat delivery vehicle comprising a core composition, an encapsulation layer surrounding the core composition, a moisture protective layer surrounding the encapsulation layer, and a fugitive layer surrounding the moisture protective layer. The core composition comprises a matrix material and a heating agent. The heating agent is surrounded by a hydrophobic wax material. The microencapsulated heat delivery vehicle has a diameter of from about 5 micrometers to about 5000 micrometers.

The present disclosure is further directed to a stabilized substantially fluid-impervious microencapsulated heat delivery vehicle comprising core composition, an encapsulation layer surrounding the core composition, a moisture protective layer surrounding the encapsulation layer, and a fugitive layer surrounding the moisture protective layer. The core composition comprises mineral oil, magnesium chloride, and a surfactant, wherein the magnesium chloride is surrounded by a hydrophobic wax material. The encapsulation layer comprises crosslinked sodium alginate and the moisture protection layer comprises vinyl toluene acrylate. The fugitive layer comprises starch. The encapsulation layer has a thickness of from about 1 micrometer to about 20 micrometers and the microencapsulated heat delivery vehicle has a diameter of from about 5 micrometers to about 5000 micrometers.

The present disclosure is further directed to a method of making a microencapsulated heat delivery vehicle. The method comprises first mixing a matrix material, a heating agent and an encapsulating activator to form a core composition. The core composition is then introduced into a liquid solution comprising a crosslinkable compound to form the microencapsulated heat delivery vehicle. Finally, the microencapsulated heat delivery vehicle is removed from the liquid solution.

The present disclosure is further directed to a method of making a microencapsulated heat delivery vehicle. The method comprises first mixing a matrix material and a heating agent to form a core composition. The core composition is then introduced into a liquid solution comprising a crosslinkable compound to form the microencapsulated heat delivery vehicle. Finally, the microencapsulated heat delivery vehicle is removed from the liquid solution.

The present disclosure is further directed to a method of making a substantially fluid-impervious microencapsulated heat delivery vehicle. The method comprises first mixing a matrix material, a heating agent, and an encapsulating activator to form a core composition. The core composition is then introduced into a liquid solution comprising a crosslinkable compound to form a microencapsulated heat delivery vehicle. The microencapsulated heat delivery vehicle is then removed from the liquid solution and a moisture protective layer is applied to the microencapsulated heat delivery vehicle such that the moisture protective layer surrounds the microencapsulated heat delivery vehicle.

The present disclosure is further directed to a method of making a stabilized substantially fluid-impervious microencapsulated heat delivery vehicle. The method comprises first mixing a heating agent, a matrix material, and an encapsulating activator to form a core composition. The core composition is then introduced into a liquid solution comprising a crosslinkable compound to form a microencapsulated heat delivery vehicle. The microencapsulated heat delivery vehicle is then removed from the liquid solution and a moisture protective layer is applied to the microencapsulated heat delivery vehicle such that the moisture protective layer surrounds the microencapsulated heat delivery vehicle. Finally, a fugitive layer is applied to the microencapsulated heat delivery vehicle such that the fugitive layer surrounds the moisture protective layer.

The present disclosure is further directed to a wet wipe comprising a fibrous sheet material, a wetting solution, and a microencapsulated heat delivery vehicle. The microencapsulated heat delivery vehicle includes an encapsulation layer that surrounds a core composition including a matrix material and a heating agent.

The present disclosure is further directed to a dry wipe comprising a fibrous sheet material and a microencapsulated heat delivery vehicle. The microencapsulated heat delivery vehicle includes an encapsulation layer that surrounds a core composition comprising a matrix material and a heating agent.

The present disclosure is further directed to a method of manufacturing a self-warming wet wipe. The method comprises embedding a microencapsulated heat delivery vehicle inside of a fibrous sheet material.

The present disclosure is further directed to a method of manufacturing a self-warming wet wipe. The method comprises depositing a microencapsulated heat delivery vehicle on an outer surface of a fibrous sheet material.

The present disclosure is further directed to a wet wipe comprising a fibrous sheet material, a wetting solution, a microencapsulated heat delivery vehicle, and a first phase change material, wherein the first phase change material is capable of providing thermal stability to the wipe.

The present disclosure is further directed to a dry wipe comprising a fibrous sheet material, a microencapsulated heat delivery vehicle, and a first phase change material, wherein the first phase change material is capable of providing thermal stability to the wipe.

The present disclosure is further directed to a method of manufacturing a self-warming wet wipe. The method comprises first embedding a microencapsulated heat delivery vehicle inside of a fibrous sheet material and then embedding a first phase change material inside of the fibrous sheet material. Finally, the fibrous sheet material containing the microencapsulated heat delivery vehicle and the first phase change material is contacted with a wetting solution.

The present disclosure is further directed to a method of manufacturing a self-warming wet wipe. The method comprises first depositing a microencapsulated heat delivery vehicle on an outer surface of a fibrous sheet material and depositing a first phase change material on the outer surface of the fibrous sheet material. Finally, the fibrous sheet material containing the microencapsulated heat delivery vehicle and first phase change material are contacted with a wetting solution.

The present disclosure is further directed to a cleansing composition comprising a biocide agent and a microencapsulated heat delivery vehicle. The microencapsulated heat delivery vehicle comprises an encapsulation layer surrounding a core composition comprising a matrix material and a heating agent.

The present disclosure is further directed to a wet wipe comprising a fibrous sheet material, a wetting solution, a biocide agent, and a microencapsulated heat delivery vehicle. The microencapsulated heat delivery vehicle comprises an encapsulation layer surrounding a core composition comprising a matrix material and a heating agent.

The present disclosure is further directed to a method of manufacturing a biocidal wet wipe. The method comprises embedding a microencapsulated heat delivery vehicle inside of the fibrous sheet material, embedding a biocide agent inside of the fibrous sheet material, and contacting the fibrous sheet material containing the microencapsulated heat delivery vehicle and biocide agent with a wetting solution.

The present disclosure is further directed to a method of manufacturing a biocidal wet wipe. The method comprises depositing a microencapsulated heat delivery vehicle on an outer surface of a fibrous sheet material, depositing a biocide agent on an outer surface of the fibrous sheet material, and contacting the fibrous sheet material containing the microencapsulated heat delivery vehicle and biocide agent with a wetting solution.

The present disclosure is further directed to a microencapsulated delivery vehicle comprising a core composition surrounded by an encapsulation layer. The core composition comprises a matrix material and a cooling agent and the microencapsulated delivery vehicle has a diameter of from about 5 micrometers to about 5000 micrometers.

The present disclosure is further directed to a substantially fluid-impervious microencapsulated delivery vehicle comprising a core composition, an encapsulation layer surrounding the core composition, and a moisture protective layer surrounding the encapsulation layer. The core. composition comprises a matrix material and a cooling agent and the microencapsulated heat delivery vehicle has a diameter of from about 5 micrometers to about 5000 micrometers.

The present disclosure is further directed to a stabilized substantially fluid-impervious microencapsulated delivery vehicle comprising a core composition, an encapsulation layer surrounding the core composition, a moisture protective layer surrounding the encapsulation layer, and a fugitive layer surrounding the moisture protective layer. The core composition comprises a matrix material and a cooling agent and the microencapsulated delivery vehicle has a diameter of from about 5 micrometers to about 5000 micrometers.

The present disclosure is further directed to a microencapsulated delivery vehicle comprising a core composition surrounded by an encapsulation layer. The core composition comprises a matrix material and a cooling agent. The cooling agent is surrounded by a hydrophobic wax material. The microencapsulated heat delivery vehicle has a diameter of from about 5 micrometers to about 5000 micrometers.

Other features of the present disclosure will be in part apparent and in part pointed out hereinafter.

DEFINITIONS

Figure 1:
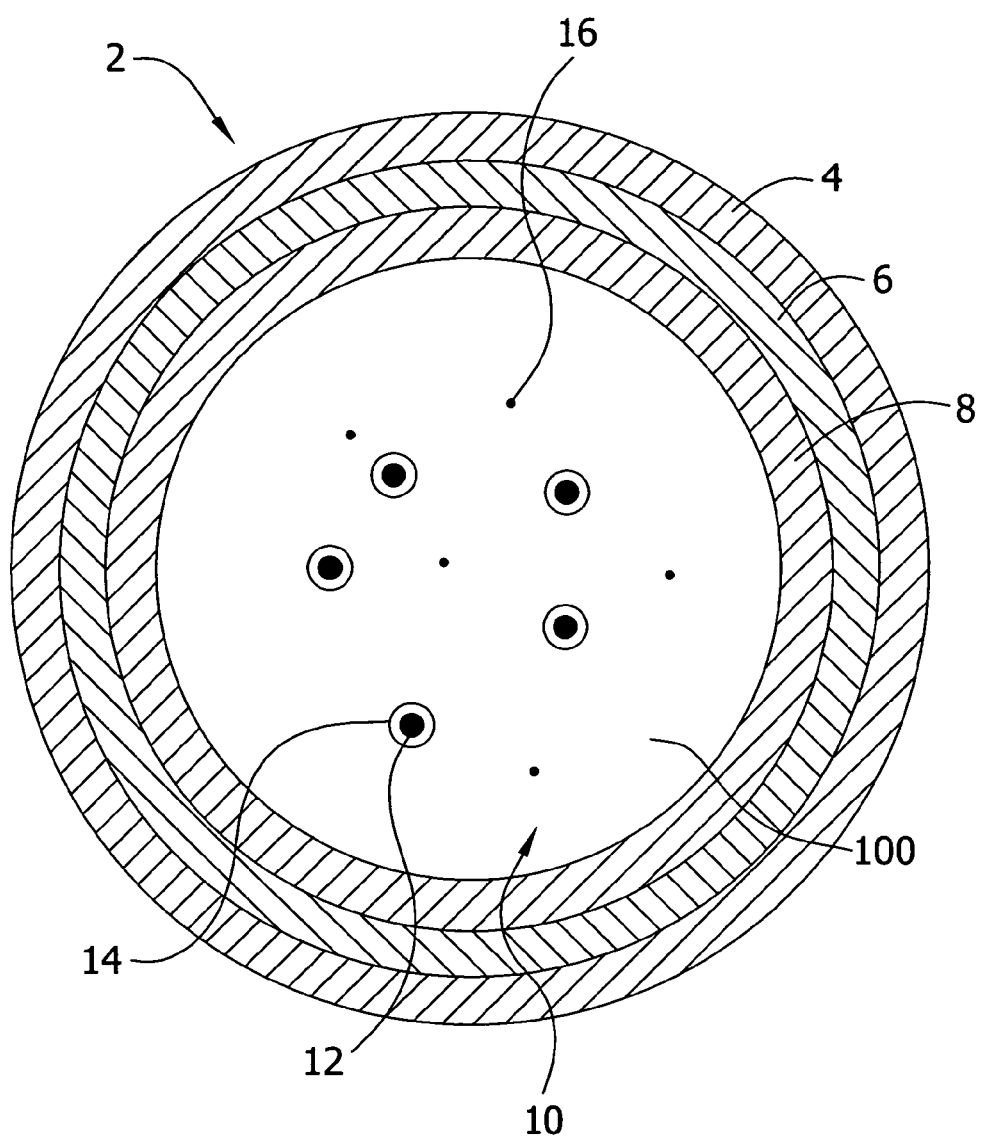
FIG. 1 depicts a cross sectional view of a microencapsulated heat delivery vehicle of the present disclosure.

Within the context of this specification, each term or phrase below will include, but not be limited to, the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Film" refers to a thermoplastic film made using a film extrusion and/or forming process, such as a cast film or blown film extrusion process. The term includes apertured films, slit films, and other porous films which constitute liquid transfer films, as well as films which do not transfer liquid.

(c) "Layer" when used in the singular can have the dual meaning of a single element or a plurality of elements.

(d) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. (Nov. 19, 1974). Meltblown fibers are microfibers which may be continuous or discontinuous, are generally smaller than about 0.6 denier, and are generally self bonding when deposited onto a collecting surface. Meltblown fibers used in the present disclosure are preferably substantially continuous in length.

(e) "Nonwoven" refers to materials and webs of material which are formed without the aid of a textile weaving or knitting process.

(f) "Polymeric" includes, but is not limited to, homopolymers, copolymers, such as for example, block, graft, random and alternating copolymers, terpolymers, etc. and blends and modifications thereof. Furthermore, unless otherwise specifically limited, the term "polymeric" shall include all possible geometrical configurations of the material. These configurations include, but are not limited to, isotactic, syndiotactic and atactic symmetries.

(g) "Thermoplastic" describes a material that softens when exposed to heat and which substantially returns to a nonsoftened condition when cooled to room temperature.

DETAILED DESCRIPTION OF THE PREFERRED EMBODIMENT

The present disclosure relates to microencapsulated delivery vehicles, such as microencapsulated heat delivery vehicles, suitable for use in personal care products such as wet wipes and dry wipes. The present disclosure also relates to self warming wipes that include a microencapsulated heat delivery vehicle and, optionally, a phase change material. The microencapsulated heat delivery vehicles, upon activation, are capable of evolving heat and causing a warming sensation on the skin of a user of the wet wipe. The microencapsulated heat delivery vehicles as described herein may include one or more encapsulating layers, moisture protective layers, and fugitive layers to impart various characteristics upon the encapsulated vehicles and the products in which they are used. Surprisingly, it has been discovered that an encapsulating activator can be included directly within a core composition and the combination introduced into a solution containing a crosslinkable compound and the thickness of the resulting crosslinked encapsulation layer closely controlled. Furthermore, in some embodiments disclosed herein, the encapsulating activator can also act as the heating agent. Additional active ingredients may also be included, with or without the heating agent, in the microencapsulated delivery vehicles.

Although discussed primarily herein in relation to microencapsulated heat delivery vehicles, it will be recognized by one skilled in the art based on the disclosure herein that other active agents or active ingredients, in addition to, or in place of, the heating agent, may be incorporated into the microencapsulated delivery vehicles described herein. For example, the microencapsulated delivery vehicles may include a heating agent and a biocide agent, or may simply include a biocide agent. A number of suitable active agents for incorporation into the microencapsulated delivery vehicles described herein are set forth below.

As noted above, the microencapsulated heat delivery vehicles as described herein may include a number of components and layers. Turning now to FIG. 1, there is shown a cross sectional view of a microencapsulated heat delivery vehicle 2 of the present disclosure. The microencapsulated heat delivery vehicle 2 includes a fugitive layer 4 surrounding a moisture protective layer 6 that surrounds an encapsulation layer 8. Additionally, microencapsulated heat delivery vehicle 2 includes a core composition 10 that includes a matrix material 100 and a heating agent 12 surrounded by a hydrophobic wax material 14, and an encapsulating activator 16. Each of these layers and components, some of which are optional, are more thoroughly discussed below.

The microencapsulated heat delivery vehicles as described herein are desirably of a size such that, when incorporated into a personal care product such as a wet wipe, they cannot readily be felt on the skin by the user. Generally, the microencapsulated heat delivery vehicles have a diameter of from about 5 micrometers to about 10,000 micrometers, desirably from about 5 micrometers to about 5000 micrometers, desirably from about 50 micrometers to about 1000 micrometers, and still more desirably from about 300 micrometers to about 700 micrometers.

The core composition includes all of the components or materials that are encapsulated as described herein by, for example, a crosslinked polymeric system, to form the microencapsulated delivery vehicles. The core composition may include, for example, the matrix material (i.e., mineral oil), the heating agent (i.e., magnesium chloride) (or other active agent as described herein), a surfactant, an encapsulating activator, and a hydrophobic wax material that surrounds the heating (or other active) agent.

Generally, the core composition is present in the microencapsulated heat delivery vehicle in an amount of from about 0.1% (by weight microencapsulated heat delivery vehicle) to about 99.99% (by weight microencapsulated heat delivery vehicle), desirably from about 1% (by weight microencapsulated heat delivery vehicle) to about 95% (by weight microencapsulated heat delivery vehicle), more desirably from about 5% (by weight microencapsulated heat delivery vehicle) to about 90% (by weight microencapsulated heat delivery vehicle), more desirably from about 10% (by weight microencapsulated heat delivery vehicle) to about 80% (by weight microencapsulated heat delivery vehicle), more desirably from about 15% (by weight microencapsulated heat delivery vehicle) to about 70% (by weight microencapsulated heat delivery vehicle), and even more desirably from about 20% (by weight microencapsulated heat delivery vehicle) to about 40% (by weight microencapsulated heat delivery vehicle).

The matrix material included in the core composition is used as a carrying or bulking agent for other components of the microencapsulated heat delivery vehicle, including, for example, the heating agent, the surfactant, and the encapsulating activator. Although generally preferred to be a liquid material, the matrix material may also be a low melting material that is a solid at room temperature. The matrix material is desirably a material that is emulsifiable in water. Preferred liquid matrix materials include oils commonly used in commercial cosmetic applications that may impart some skin benefit to the user, such as a moisturizing or lubricating benefit. Generally, these oils are hydrophobic oils.

Specific examples of suitable liquid matrix materials include, for example, mineral oil, isopropyl myristate, silicones, copolymers such as block copolymers, waxes, butters, exotic oils, dimethicone, thermoionic gels, plant oils, animal oils, and combinations thereof. One preferred material for use as the matrix material is mineral oil. The matrix material is generally present in the core composition of the microencapsulated heat delivery vehicle in an amount of from about 1% (by weight core composition) to about 99% (by weight core composition), desirably from about 10% (by weight core composition) to about 95% (by weight core composition), more desirably from about 15% (by weight core composition) to about 75% (by weight core composition), more desirably from about 20% (by weight core composition) to about 50% (by weight core composition), more desirably from about 25% (by weight core composition) to about 45% (by weight core composition), and even more desirably from about 30% (by weight core composition) to about 40% (by weight core composition).

The microencapsulated heat delivery vehicle as disclosed herein also includes a heating agent that is contained in the core composition. The heating agent releases heat when contacted with water and may result in a warm feeling on the skin if used in combination with a personal care product such as a wet wipe. Suitable heating agents for use in the microencapsulated heat delivery vehicles include compounds with an exothermic heat of hydration and compounds with an exothermic heat of solution. Suitable compounds for use as heating agents in the core composition include, for example, calcium chloride, magnesium chloride, zeolites, aluminum chloride, calcium sulfate, magnesium sulfate, sodium carbonate, sodium sulfate, sodium acetate, metals, slaked lime, quick lime, glycols, and combinations thereof. The heating agents may be in either hydrous or anhydrous forms, although anhydrous forms are generally preferred. Particularly preferred compounds include magnesium chloride and calcium chloride.

The heating agent is generally included in the core composition of the microencapsulated heat delivery vehicle in an amount of from about 0.1% (by weight core composition) to about 98% (by weight core composition), desirably from about 1% (by weight core composition) to about 80% (by weight core composition), more desirably from about 20% (by weight core composition) to about 70% (by weight core composition), more desirably from about 30% (by weight core composition) to about 60% (by weight core composition), more desirably from about 35% (by weight core composition) to about 55% (by weight core composition), and even more desirably about 55% (by weight core composition).

The heating agent utilized in the microencapsulated heat delivery vehicle generally has a particle size of from about 0.05 micrometers to about 4000 micrometers, desirably from about 10 micrometers to about 1000 micrometers, desirably from about 10 micrometers to about 500 micrometers, and more desirably from about 10 micrometers to about 100 micrometers to facilitate substantial and continuous heat release. In one specific embodiment, a particle size of from about 149 micrometers to about 355 micrometers is preferred. Although many heating agents as described herein are commercially available in a number of particle sizes, it will be recognized by one skilled in the art that any number of techniques can be used to grind and produce the desired particle sizes.

Along with the heating agent, a surfactant may optionally be included in the core composition. As used herein, "surfactant" is intended to include surfactants, dispersants, gelling agents, polymeric stabilizers, structurants, structured liquids, liquid crystals, Theological modifiers, grinding aids, defoamers, block copolymers, and combinations thereof. If a surfactant is utilized, it should be substantially non-reactive with the heating agent. A surfactant may be added along with a heating agent and matrix material to the core composition as a grinding and mixing aid for the heating agent and to reduce the surface tension of the core composition and allow for better mixing with water and an increase in heating ability upon use. In one embodiment, the use of a surfactant in the core composition generally allows for higher loading of the heating material (or other active agent as described herein) within the core composition without unwanted flocculation of the heating material occurring, which can hinder heat release by the heating agent.

Any one of a number of surfactant types including anionic, cationic, nonionic, zwitterionic, and combinations thereof can be utilized in the core composition. One skilled in the art will recognize, based on the disclosure herein, that different heating agents in combination with different matrix materials may benefit from one type of surfactant more than another; that is, the preferred surfactant for one chemistry may be different than the preferred surfactant for another. Particularly desirable surfactants will allow the core composition including the matrix material, heating agent, and surfactant mixture to have a suitable viscosity for thorough mixing; that is, the surfactant will not result in the mixture having an undesirably high viscosity. Generally, low HLB surfactants are desirable; that is, surfactants having an HLB of less than about 7. Examples of commercially available surfactants suitable for use in the matrix material include, for example, Antiterra 207 (BYK Chemie, Wallingford, Conn.) and BYK-P104 (BYK Chemie).

When included in the core composition of the microencapsulated heat delivery vehicles of the present disclosure, the surfactant is generally present in an amount of from about 0.01% (by weight core composition) to about 50% (by weight core composition), desirably from about 0.1% (by weight core composition) to about 25% (by weight core composition), more desirably from about 0.1% (by weight core composition) to about 10% (by weight core composition), more desirably from about 1% (by weight core composition) to about 5% (by weight core composition), and still more desirably about 1% (by weight core composition).

As will be described in more detail below, during the manufacturing process for the microencapsulated heat delivery vehicle, the core composition including the matrix material and the heating agent is introduced into an aqueous environment. During contact with this aqueous environment, it may be possible for the heating agent present in the core composition to come into contact with water. This contact can result in a loss of potency and deactivation of the heating agent and render the resulting microencapsulated heat delivery vehicle ineffective for its intended purpose. As such, in one embodiment of the present disclosure, the heating agent included in the core composition is substantially completely surrounded by a hydrophobic wax material prior to being introduced into the core composition and ultimately into the aqueous environment. As used herein, the term "hydrophobic wax material" means a material suitable to coat and protect the heating agent (or other active agent) from water. This hydrophobic wax material may provide the heating agent with temporary water protection during the timeframe of exposure to the aqueous environment; that is, the hydrophobic wax material may keep water from contacting the heating agent. Although the hydrophobic wax material provides protection of the heating agent during treatment of the core composition in an aqueous environment, in one embodiment it will gradually dissolve away and off of the heating agent within the core composition over time; that is, the hydrophobic wax material dissolves into the bulk of the core composition over time and off of the heating agent so that the heating agent can be directly contacted with water upon activation in a wipe or other product.

In an alternative embodiment, the hydrophobic wax material does not substantially dissolve into the core composition and off of the heating agent but is removed from the heating agent at the time of use through shearing or disruption of the hydrophobic wax material; that is, the hydrophobic wax material is mechanically broken off of the heating agent to allow the heating agent access to water.

It is generally desirable to have substantially complete coverage of the heating agent with the hydrophobic wax material to ensure that the heating agent is not susceptible to contact with water during the introduction of the core composition into the aqueous liquid as described herein. When contacted with a substantially continuous layer of hydrophobic wax material, the core composition including the matrix material and the heating agent can be encapsulated in the liquid environment without the heating agent losing potency. Generally, the hydrophobic wax material may be applied to the heating agent in from about 1 to about 30 layers, desirably in from about 1 to about 10 layers.

Generally, the hydrophobic wax material is present on the heating agent in an amount of from about 1% (by weight heating agent) to about 50% (by weight heating agent), desirably from about 1% (by weight heating agent) to about 40% (by weight heating agent), more desirably from about 1% (by weight heating agent) to about 30% (by weight heating agent), and even more desirably from about 1% (by weight heating agent) to about 20% (by weight heating agent). At these levels, there is sufficient hydrophobic wax material present on the heating agent to provide the desired level of protection, yet not too much to keep it from dissolving over time into the core composition to allow for water to access the heating agent at the desired time.

Suitable hydrophobic wax materials for coating the heating agent are relatively low temperature melting wax materials. Although other hydrophobic low temperature melting materials can be used to coat the heating agent in accordance with the present disclosure, low temperature melting hydrophobic wax materials are generally preferred. In one embodiment, the hydrophobic wax material has a melting temperature of less than about 140° C., desirably less than about 90° C. to facilitate the coating of the heating agent as described below.

Suitable hydrophobic wax materials for use in coating the heating agent (or other active agent) include, for example, organic ester and waxy compounds derived from animal, vegetable, and mineral sources including modifications of such compounds in addition to synthetically produced materials having similar properties. Specific examples that may be used alone or in combination include glyceryl tristearate, glyceryl distearate, canola wax, hydrogenated cottonseed oil, hydrogenated soybean oil, castor wax, rapeseed wax, beeswax, carnauba wax, candelilla wax, microwax, polyethylene, polypropylene, epoxies, long chain alcohols, long chain esters, long chain fatty acids such as stearic acid and behenic acid, hydrogenated plant and animal oils such as fish oil, tallow oil, and soy oil, microcrystalline waxes, metal stearates and metal fatty acids. Specific commercially available hydrophobic wax materials include, for example, Dynasan™ 110, 114, 116, and 118 (commercially available from DynaScan Technology Inc., Irvine, Calif.), Sterotex™ (commercially available from ABITEC Corp., Janesville, Wis.); Dritex C (commercially available from Dritex International, LTD., Essex, U.K.); Special Fat™ 42, 44, and 168T.

As noted herein, the microencapsulated heat delivery vehicles include an encapsulation layer that substantially completely surrounds the core composition that includes the matrix material, heating agent and optionally the hydrophobic wax material and the surfactant (and optionally an encapsulating activator as discussed below). The encapsulation layer allows the core composition including the heating agent or other active agent to undergo further processing and use without a loss of structural integrity; that is, the encapsulation layer provides structural integrity to the core composition and its contents to allow for further processing.

Although described in more detail below, and generally in relation to a crosslinked polymeric material, the encapsulation layer may be comprised of a polymeric material, a crosslinked polymeric material, a metal, a ceramic or a combination thereof, that results in a shell material that may be formed during manufacturing. Specifically, the encapsulation layer may be comprised of crosslinked sodium alginate, anionic dispersed latex emulsions, crosslinked polyacrylic acid, crosslinked polyvinyl alcohol, crosslinked polyvinyl acetate, silicates, carbonates, sulfates, phosphates, borates, polyvinyl pyrolidone, PLA/PGA, thermoionic gels, urea formaldehyde, melamine formaldehyde, polymelamine, crosslinked starch, nylon, ureas, hydrocolloids, and combinations thereof. One particularly preferred crosslinked polymeric system is crosslinked sodium alginate.

The encapsulation layer present in the microencapsulated heat delivery vehicle generally has a thickness of from about 0.1 micrometers to about 500 micrometers, desirably from about 1 micrometer to about 100 micrometers, more desirably from about 1 micrometer to about 50 micrometers, more desirably from about 1 micrometer to about 20 micrometers, and even more desirably from about 10 micrometers to about 20 micrometers. At these thicknesses, the crosslinked polymeric layer has a sufficient thickness to provide its intended function. The encapsulation layer may be one discrete layer, or may be comprised of multiple layers added in one or more steps. Suitable methods for measuring the thickness of the encapsulation layer (once fractured), and the other optional layers described herein, include Scanning Electron Microscopy (SEM) and Optical Microscopy.

Generally, the encapsulation layer will be present in from about 1 layer to about 30 layers, desirably in from about 1 layer to about 20 layers, and more desirably in from about 1 layer to about 10 layers to provide further protection.

The encapsulation layer is generally present in the microencapsulated heat delivery vehicle in an amount of from about 0.001% (by weight microencapsulated heat delivery vehicle) to about 99.8% (by weight microencapsulated heat delivery vehicle), desirably from about 0.1% (by weight microencapsulated heat delivery vehicle) to about 90% (by weight microencapsulated heat delivery vehicle), more desirably from about 1% (by weight microencapsulated heat delivery vehicle) to about 75% (by weight microencapsulated heat delivery vehicle), more desirably from about 1% (by weight microencapsulated heat delivery vehicle) to about 50%(by weight microencapsulated heat delivery vehicle), more desirably from about 1% (by weight microencapsulated heat delivery vehicle) to about 20% (by weight microencapsulated heat delivery vehicle), and still more desirably about 1% (by weight microencapsulated heat delivery vehicle).

The microencapsulated heat delivery vehicle as described herein may optionally comprise a moisture protective layer to produce a substantially fluid-impervious microencapsulated heat delivery vehicle. As used herein, "fluid" is meant to include both water (and other fluids) and oxygen (and other gases) such that "fluid-impervious" includes both water-impervious and oxygen-impervious. Although referred to throughout herein as a "moisture protective layer," one skilled in the art based on the disclosure herein will recognize that this layer may be both "moisture protective" and "oxygen protective;" that is, the layer will protect and insulate the core composition and its contents from both water and oxygen.

When present, the moisture protective layer substantially completely surrounds the crosslinked polymeric encapsulation layer described above. The moisture protective layer may be utilized when it is desirable to impart additional water (and/or oxygen) repelling characteristics onto the microencapsulated heat delivery vehicle. For example, if the microencapsulated heat delivery vehicle is to be used in a wet wipe, it may be desirable to utilize a moisture protective layer on top of the encapsulating layer such that the active heating agent is shielded from the water contained in the wet wipe solution until the end user ruptures the microencapsulated heat delivery vehicle at the desired time of use to allow water to contact the heating agent. In the absence of a moisture protective layer, when the microencapsulated heat delivery vehicle is used in a wet wipe, it may be possible that over time the water present in the wet wipe solution can diffuse and gain access through the crosslinked encapsulated shell described above and gain access to the heating agent causing it to release its heat prematurely.

The moisture protective layer may be present on the microencapsulated heat delivery vehicle in one layer or in multiple layers. Desirably, the moisture protective layer will be present in from about 1 layer to about 30 layers, desirably in from about 1 layer to about 20 layers, and more desirably in from about 1 layer to about 10 layers to provide further protection. As noted above, the moisture protective layer substantially completely surrounds the encapsulating layer to keep water from reaching the internal matrix material and ultimately the heating agent. To ensure the moisture protective layer substantially completely covers the encapsulating layer, multiple layers may be utilized as noted above. Each of the moisture protective layers generally has a thickness of from about 1 micrometer to about 200 micrometers, desirably from about 1 micrometer to about 100 micrometers, and even more desirably from about 1 micrometer to about 50 micrometers.

The moisture protective layer may comprise any number of materials including, for example, polyols in combination with isocynate, styrene-acrylate, vinyl toluene-acrylate, styrene-butadiene, vinyl-acrylate, polyvinyl butyral, polyvinyl acetate, polyethylene terephthalate, polypropylene, polystyrene, polymethyl methacrylate, poly lactic acid, polyvinylidene chloride, polyvinyldichloride, polyethylene, alkyd polyester, carnauba wax, hydrogenated plant oils, hydrogenated animal oils, fumed silica, silicon waxes, titanium dioxide, silicon dioxide, metals, metal carbonates, metal sulfates, ceramics, metal phosphates, microcrystalline waxes, and combinations thereof.

Generally, the moisture protective layer is present in the microencapsulated heat delivery vehicle in an amount of from about 0.001% (by weight microencapsulated heat delivery vehicle) to about 99.8% (by weight microencapsulated heat delivery vehicle), desirably from about 0.1% (by weight microencapsulated heat delivery vehicle) to about 90% (by weight microencapsulated heat delivery vehicle), more desirably in an amount of from about 1% (by weight microencapsulated heat delivery vehicle) to about 75% (by weight microencapsulated heat delivery vehicle), more desirably in an amount of from about 1% (by weight microencapsulated heat delivery vehicle) to about 50% (by weight microencapsulated heat delivery vehicle), and even more desirably in an amount of from about 5% (by weight microencapsulated heat delivery vehicle) to about 35% (by weight microencapsulated heat delivery vehicle).

In addition to the moisture protective layer, the microencapsulated heat delivery vehicle may also optionally include a fugitive layer that surrounds the moisture protective layer, if present, or the encapsulating layer if the moisture protective layer is not present. The fugitive layer can act to stabilize and protect the microencapsulated heat delivery vehicle from rupturing prematurely due to mechanical load, or can provide other benefits. When present on the microencapsulated heat delivery vehicle, the fugitive layer can impart strength and withstand a given mechanical load until a time when the fugitive layer is ruptured by the end user or is decomposed or degraded in a predictable manner in a wet wipe solution, usually during shipment and/or storage of the product prior to use. Consequently, the fugitive layer allows the microencapsulated heat delivery vehicle to survive relatively high mechanical load conditions commonly experienced in shipping and/or manufacturing.

In one embodiment, the fugitive layer substantially completely surrounds the moisture protective layer (or the encapsulating layer) such that there are substantially no access points to the underlying layer. Alternatively, the fugitive layer may be a non-continuous, porous or non-porous layer surrounding the moisture protective layer (or the encapsulating layer).

The fugitive layer, similar to the moisture protective layer, may be present in multiple layers. Specifically, the fugitive layer may be present in anywhere from about 1 to about 30 layers, desirably from about 1 to about 20 layers, and more desirably from about 1 to about 10 layers. Generally, each fugitive layer may have a thickness of from about 1 micrometer to about 200 micrometers, desirably from about 1 micrometer to about 100 micrometers, and more desirably from about 1 micrometer to about 50 micrometers.

The fugitive layer is generally present in the microencapsulated heat delivery vehicle in an amount of from about 0.001% (by weight microencapsulated heat delivery vehicle) to about 99.8% (by weight microencapsulated heat delivery vehicle), desirably in an amount of from about 0.1% (by weight microencapsulated heat delivery vehicle) to about 90% (by weight microencapsulated heat delivery vehicle), more desirably in an amount of from about 1% (by weight microencapsulated heat delivery vehicle) to about 80% (by weight microencapsulated heat delivery vehicle), more desirably in an amount of from about 1% (by weight microencapsulated heat delivery vehicle) to about 75% (by weight microencapsulated heat delivery vehicle), and even more desirably in an amount of from about 1% (by weight microencapsulated heat delivery vehicle) to about 50% (by weight microencapsulated heat delivery vehicle).

The fugitive layer may be comprised of any one of a number of suitable materials including, for example, polylactic acid, polymers of dextrose, hydrocolloids, alginate, zein, and combinations thereof. One particularly preferred material for use as the fugitive layer is starch.

The microencapsulated heat delivery vehicles as described herein may be manufactured in any number of ways as discussed below. The first step in the manufacturing process is generally to coat the desired heat delivery vehicle (i.e., magnesium chloride) with a hydrophobic wax material as described above prior to incorporating the hydrophobic wax material-coated heating agent into the core composition. As would be recognized by one skilled in the art based on the disclosure herein, this hydrophobic wax material coating of the heating agent step is optional and can be eliminated if such a coating is not desired and the heating agent is to be incorporated into the core composition without any protective coating.

In one embodiment, the hydrophobic wax material is coated onto the heating agent by blending the heating agent and hydrophobic wax material together at an elevated temperature sufficient to melt the hydrophobic wax material in the presence of the heating agent and the melted wax material and heating agent stirred sufficiently to coat the heating agent. After the coating of the heating agent is complete, the mixture is allowed to cool to room temperature to allow the wax to solidify on the heating agent particles. After the coated heating agent particles have cooled, they can be ground to the desired size prior to incorporation into the matrix material.

After the grinding of the hydrophobic wax material-coated heating agent, it may be desirable to subject the ground material to a further process to ensure that the hydrophobic wax material coating is substantially complete around the heating agents. Suitable additional processes include, for example, spheroidization (high heat fluidization slightly below the melt temperature of the hydrophobic wax material) and ball milling. These additional processes can be used to ensure substantially complete coverage of the heating agent with the hydrophobic wax material.

In preparing the microencapsulated heat delivery vehicle, a core composition including the hydrophobic wax material-coated (or uncoated) heating agent, an optional encapsulating activator, and surfactant (if utilized) are first mixed together with the matrix material. This core composition is the resulting "core material" inside of the encapsulating layer(s), although it will be recognized by one skilled in the art based on the disclosure herein that the encapsulating activator, if initially present in the core composition, may be substantially or completely used up in the crosslinking reaction described herein. As will be further recognized by one skilled in the art, some methods of forming an outer layer on the core composition (i.e., coacervation) may not require a chemical encapsulating activator to be present in the core composition, but may utilize a change in pH, a change in temperature, and/or a change in ionic strength of the liquid solution to initiate the formation of the encapsulating layer around the core composition. Additionally, it will be further recognized by one skilled in the art based on the disclosure herein that the encapsulating activator, when present, may be located outside of the core composition; that is, the encapsulating activator may be located in the liquid solution for example, although it is generally desirable to have it located within the core composition.

The encapsulating activator, when present in the core composition, acts as a crosslinking agent to crosslink the encapsulating layer discussed herein. Once the core composition is introduced into a liquid solution containing a crosslinkable compound as described below, the encapsulating activator interacts with the crosslinkable compound and causes it to crosslink on the outer surface of the composition to form a crosslinked shell. Because the encapsulating activator chemically reacts with the crosslinkable compound contained in the liquid solution, the resulting microencapsulated heat delivery vehicle may not contain any encapsulating activator in its final form; or, it may contain a small amount of encapsulating activator not consumed in the crosslinking reaction, which in some cases may then act as an additional heating agent.

The encapsulating activator may be any activator capable of initiating a crosslinking reaction in the presence of a crosslinkable compound. Suitable encapsulating activators include, for example, polyvalent ions of calcium, polyvalent ions of copper, polyvalent ions of barium, silanes, aluminum, titanates, chelators, acids, and combinations thereof. Specifically, the encapsulating activator may be calcium chloride, calcium sulfate, calcium oleate, calcium palmitate, calcium stearate, calcium hypophosphite, calcium gluconate, calcium formate, calcium citrate, calcium phenylsulfonate, and combinations thereof. A preferred encapsulating activator is calcium chloride.

The encapsulating activator is generally present in the core composition in an amount of from about 0.1% (by weight core composition) to about 25% (by weight core composition), desirably from about 0.1% (by weight core composition) to about 15% (by weight core composition), and still more desirably from about 0.1% (by weight core composition) to about 10% (by weight composition).

One skilled in the art will recognize based on the disclosure herein that the encapsulating activator may be the same chemical compound as the heating agent; that is, the same chemical compound may act as both the encapsulating activator and the heating agent. For example, in one embodiment, calcium chloride may be added to the composition as both heating agent and encapsulating activator. When a single compound is to function as both heating agent and encapsulating activator, an increased amount is utilized in the composition to ensure there is sufficient compound remaining after the crosslinking reaction to function as the heating agent. Of course, if a single compound, such as calcium chloride, is to function as both heating agent and encapsulating activator, a portion of the calcium chloride may be surrounded as described herein by a hydrophobic wax material prior to incorporation into the composition. This protected portion of the dual function compound would not be available in this embodiment to act as an encapsulating activator.

To produce the core composition including the matrix material, heating agent (which may or may not be surrounded by a hydrophobic wax material), encapsulating activator and surfactant (if any), the desired amounts of these components may be optionally passed through a milling device that serves. to thoroughly mix the components together for further processing. Suitable wet milling operations include, for example, bead milling and wet ball milling. Additionally, processes known to those skilled in the art such as hammer milling and jet milling may be used to first prepare the heating agent, and then disperse the treated heating agent into the matrix material containing the surfactant and encapsulating activator followed by thorough mixing.

Once the core composition is prepared, it is introduced into a liquid solution, generally held at room temperature, to activate a crosslinking reaction to form an outer encapsulating shell that protects the core composition and its components (core material) and allows for immediate use or further processing. Although described herein primarily in reference to a "crosslinking reaction," it will be recognized by one skilled in the art based on the disclosure herein that the encapsulation layer can be formed around the core composition not only by a crosslinking reaction, but also by coacervation, coagulation, flocculation, adsorbtion, complex coacervation and self-assembly, all of which are within the scope of the present disclosure. As such, the term "crosslinking reaction" is meant to include these other methods of forming the encapsulation layer around the core composition.

One particular advantage of one embodiment described herein is that the presence of the encapsulating activator in the core composition allows for almost instantaneous crosslinking when the core composition is introduced into the solution containing the crosslinkable compound; this reduces the potential for unwanted heating agent deactivation. In one embodiment, the core composition is added dropwise into the liquid containing the crosslinkable compound and the beads that form when the drops contact the liquid are kept separated during the crosslinking reaction using a sufficient amount of stirring and mixing. It is preferred to use sufficient stirring and mixing to keep the beads separate during the crosslinking reaction to ensure that they remain separate, individual beads and do not form larger agglomerated masses that are susceptible to numerous defects. Generally, the drops added to the liquid solution can have a diameter of from about 0.05 millimeters to about 10 millimeters, desirably from about 1 millimeter to about 3 millimeters, and still more desirably from about 0.5 millimeters to about 1 millimeter. Alternatively, the core composition may be introduced or poured into the liquid solution including the crosslinkable compound and then subjected to shear sufficient to break the paste into small beads for crosslinking thereon.

In one embodiment, the liquid solution includes a crosslinkable compound that can be crosslinked in the presence of the encapsulating activator to form the outer encapsulate shell. Optionally, a surfactant as described herein can also be introduced into the liquid solution to facilitate crosslinking. When the core composition including the encapsulating activator is introduced into the liquid containing the crosslinkable compound, the encapsulating activator migrates to the interface between the core composition and the liquid solution and initiates the crosslinking reaction on the surface of the core composition to allow the encapsulation layer to grow outward toward the liquid solution. The thickness of the resulting encapsulation layer surrounding the core composition can be controlled by (1) controlling the amount of encapsulating activator included in the core composition; (2) controlling the amount of time the core composition including the encapsulating activator is exposed to the liquid solution including the crosslinkable compound; and/or (3) controlling the amount of crosslinkable compound in the liquid solution. Generally, an encapsulating layer of sufficient and desired thickness can be formed around the core composition by allowing the core composition to dwell in the liquid solution including the crosslinkable compound for from about 10 seconds to about 40 minutes, desirably from about 5 minutes to about 30 minutes, and still more desirably from about 10 minutes to about 20 minutes.

It is generally desirable that the liquid solution containing the crosslinkable compound has a viscosity suitable for allowing sufficient mixing of the formed beads therein; that is, the viscosity of the liquid solution should not be so high that stirring and mixing is substantially impaired and the ability to keep the formed beads separated reduced. To that end, the liquid solution containing the crosslinkable compound generally contains from about 0.1% (by weight liquid solution) to about 50% (by weight liquid solution), desirably from about 0.1% (by weight liquid solution) to about 25% (by weight liquid solution) and more desirably from about 0.1% (by weight liquid solution) to about 1% (by weight liquid solution) crosslinkable compound.

Any number of crosslinkable compounds can be incorporated into the liquid solution to form the encapsulated layer around the core composition upon contact with the encapsulating activator. Some suitable crosslinkable compounds include, for example, sodium alginate, anionic dispersed latex emulsions, polyacrylic acid, polyvinyl alcohol, polyvinyl acetate, silicates, carbonates, sulfates, phosphates, borates, and combinations thereof. A particularly desirable crosslinkable compound is sodium alginate.

Once a sufficient amount of time has passed for the encapsulating layer to form on the core composition, the formed beads may be removed from the liquid including the crosslinkable compound. The resulting microencapsulated heat delivery vehicles may optionally be washed several times to remove any crosslinkable compound thereon and dried and are then ready for use or for further processing. One suitable washing liquid is deionized water.

In one embodiment, the microencapsulated heat delivery vehicles formed as described above are subjected to a process to impart a moisture protective layer thereon that surrounds the encapsulated layer that comprises the crosslinked compound. This moisture protective layer provides the microencapsulated heat delivery vehicle with increased protection from water; that is, it makes the microencapsulated heat delivery vehicle substantially fluid impervious and allows the microencapsulated heat delivery vehicle to survive long term in an aqueous environment and not degrade until the moisture protective layer is ruptured by mechanical action. The moisture protective layer may be a single layer applied onto the microencapsulated heat delivery vehicle, or may comprise several layers one on top of the other.

The moisture protective layer may be applied to the microencapsulated heat delivery vehicle utilizing any number of suitable processes including, for example, atomizing or dripping a moisture protective material onto the microencapsulated heat delivery vehicle. Additionally, a Wurster coating process may be utilized. When a solution is used to provide the moisture protective coating, the solids content of the solution is generally from about 0.1% (by weight solution) to about 70% (by weight solution), desirably from about 0.1%

(by weight solution) to about 60% (by weight solution), and still more desirably from about 5% (by weight solution) to about 40% (by weight solution). Generally, the viscosity of the solution (at 25° C.) including the moisture protective material is from about 0.6 centipoise to about 10,000 centipoise, desirably from about 20 centipoise to about 400 centipoise, and still more desirably from about 20 centipoise to about 100 centipoise.

Figure 2:
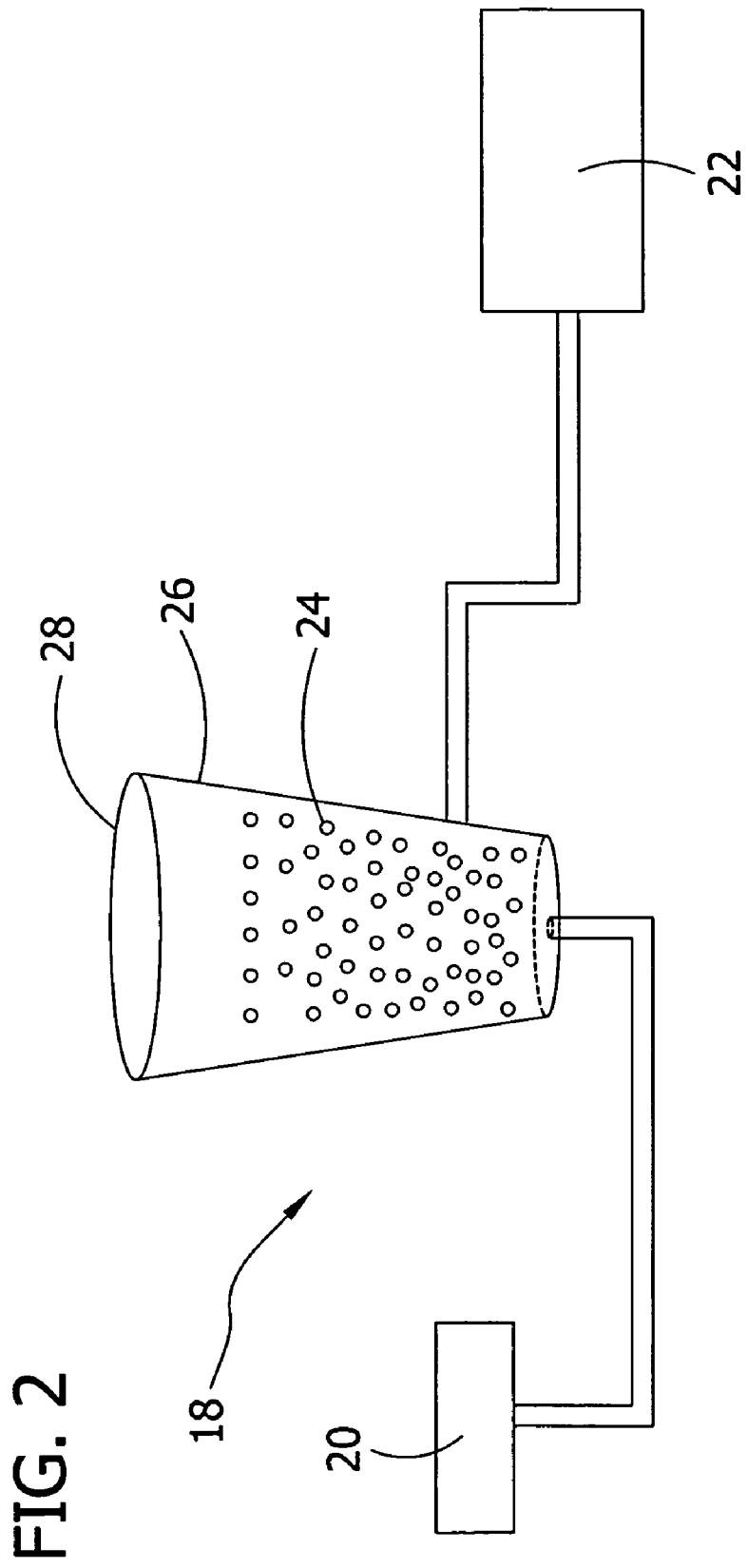
FIG. 2 depicts a fluidized bed coating apparatus for use imparting a moisture protective layer to a microencapsulated heat delivery vehicle.

In one specific embodiment, a fluidized bed process is utilized to impart the moisture protective layer on the microencapsulated heat delivery vehicle. The fluidized bed is a bed or layer of microencapsulated heat delivery vehicles through which a stream of heated or unheated carrier gas is passed at a rate sufficient to set the microencapsulated heat delivery vehicles in motion and cause them to act like a fluid. As the vehicles are fluidized, a spray of a solution comprising a carrier solvent and the moisture protective material is injected into the bed and contacts the vehicles imparting the moisture protective material thereon. The treated vehicles are collected when the desired moisture protective layer thickness is achieved. The microencapsulated heat delivery vehicles can be subjected to one or more fluidized bed processes to impart the desired level of moisture protective layer. A suitable fluidized bed coating apparatus is illustrated in FIG. 2 wherein the fluidized bed reactor 18 includes heated carrier gas supply 20, solvent and moisture protective material supply 22, and microencapsulated heat delivery vehicles 24 contained in chamber 26. The heated gas and solvent exit the chamber 26 at the top 28 of chamber 26.

In another embodiment, the microencapsulated heat delivery vehicle, which may or may not include a moisture protective layer as described above, is subjected to a process for imparting a fugitive layer thereon surrounding the outermost layer. For example, if the microencapsulated heat delivery vehicle includes a moisture protective layer, the fugitive layer would be applied on the microencapsulated heat delivery vehicle such that it substantially completely covered the moisture protective layer. The fugitive layer can be applied in a single layer, or may be applied in multiple layers.

The fugitive layer may be applied to the microencapsulated heat deliver vehicle utilizing any number of suitable processes including, for example, atomizing or dripping a fugitive material onto the microencapsulated heat delivery vehicle. When a solution is used to provide the fugitive coating, the solids content of the solution is generally from about 1% (by weight solution) to about 70% (by weight solution), desirably from about 10% (by weight solution) to about 60% (by weight solution). The pH of the solution is generally from about 2.5 to about 11. Generally, the viscosity of the solution (at 25° C.) including the fugitive material is from about 0.6 centipoise to about 10,000 centipoise, desirably from about 20 centipoise to about 400 centipoise, and still more desirably from about 20 centipoise to about 100 centipoise. Similar to the moisture protective layer, a preferred method of applying the fugitive layer utilized a fluidized bed reactor. Also, a Wurster coating process may also be used.

In an alternative embodiment of the present disclosure, the heating agent in the core composition can be combined with one or more other active ingredients to impart additional benefits to the end user; that is, the core composition may comprise two or more active agents. The two or more active agents may include a heating agent, or may not include a heating agent. Also, the core composition may include a single active agent that is not a heating agent. Additionally, the active agent or combination of active agents can be located in one or more of the layers surrounding the core composition including, for example, in the encapsulation layer, the moisture protective layer, and/or the fugitive layer. Also, the active agent or combination of active agents can be located in-between two of the layers on the microencapsulated delivery vehicle. For example, in one embodiment the microencapsulated delivery vehicle may include a heating agent in the core composition surrounded by a crosslinked encapsulation layer surrounded by a moisture protective layer that includes therein a fragrance oil.

A number of alternative or additional active agents are suitable for inclusion in the core composition. Active agents such as neurosensory agents (agents that induce a perception of temperature change without involving an actual change in temperature such as, for example peppermint oil, eucalyptol, eucalyptus oil, methyl salicylate, camphor, tea tree oil, ketals, carboxamides, cyclohexanol derivatives, cyclohexyl derivatives, and combinations thereof), cleansing agents (e.g., tooth health agents, enzymes), appearance modifying agents (e.g., tooth whitening agents, exfoliation agents, skin-firming agents, anti-callous agents, anti-acne agents, anti-aging agents, anti-wrinkle agents, anti-dandruff agents, antiperspirant agents, wound care agents, enzyme agents, scar repair agents, colorant agents, humectant agents, hair care agents such as conditioners, styling agents, and detangling agents), powders, skin coloration agents such as tanning agents, lightening agents, and brightening agents, shine control agents and drugs), nutrients (e.g., anti-oxidants, transdermal drug delivery agents, botanical extracts, vitamins, magnets, magnetic metals, foods, and drugs), pesticides (e.g., tooth health ingredients, anti-bacterials, anti-virals, anti-fungals, preservatives, insect repellants, anti-acne agents, anti-dandruff agents, anti-parasite agents, wound care agents, and drugs), surface conditioning agents (e.g., pH adjusting agents, moisturizers, skin conditioners, exfoliation agents, shaving lubricants, skin-firming agents, anti-callous agents, anti-acne agents, anti-aging agents, anti-wrinkle agents, anti-dandruff agents, wound care agents, skin lipids, enzymes, scar care agents, humectants, powders, botanical extracts, and drugs), hair care agents (e.g., shaving lubricants, hair growth inhibitors, hair growth promoters, hair removers, anti-dandruff agents, colorant agents, humectants, hair care agents such as conditioners, styling agents, detangling agents, and drugs), anti-inflammatory agents (e.g., tooth health ingredients, skin conditioners, external analgesic agents, anti-irritant agents, anti-allergy agents, anti-inflammatory agents, wound care agents, transdermal drug delivery, and drugs), emotional benefit agents (e.g., gas generating agents, fragrances, odor neutralizing materials, exfoliation agents, skin-firming agents, anti-callous agents, anti-acne agents, anti-aging agents, soothing agents, calming agents, external analgesic agents, anti-wrinkle agents, anti-dandruff agents, antiperspirants, deodorants, wound care agents, scar care agents, coloring agents, powders, botanical extracts and drugs), indicators (e.g., soil indicators), and organisms.

Additional suitable active agents include abrasive materials, abrasive slurries, acids, adhesives, alcohols, aldehydes, animal feed additives, antioxidants, appetite suppressants, bases, biocides, blowing agents, botanical extracts, candy, carbohydrates, carbon black, carbonless copying materials, catalysts, ceramic slurries, chalcogenides, colorants, cooling agents, corrosion inhibitors, curing agents, detergents, dispersants, EDTA, enzymes, exfoliation, fats, fertilizers, fibers, fire retardant materials, flavors, foams, food additives, fragrances, fuels, fumigants, gas forming compounds, gelatin, graphite, growth regulators, gums, herbicides, herbs, spices, hormonal based compounds, humectants, hydrides, hydrogels, imaging materials, ingredients that are easily oxidized or not UV stable, inks, inorganic oxides, inorganic salts, insecticides, ion exchange resins, latexes, leavening agents, liquid crystals, lotions, lubricants, maltodextrins, medicines, metals, mineral supplements, monomers, nanoparticles, nematicides, nicotine-based compounds, oil recovery agents, organic solvents, paint, peptides, pesticides, pet food additives, phase change materials, phase change oils, pheromones, phosphates, pigments, dyes, plasticizers, polymers, propellants, proteins, recording materials, silicates, silicone oils, stabilizers, starches, steroids, sugars, surfactants, suspensions, dispersions, emulsions, vitamins, warming materials, waste treatment materials, adsorbents, water insoluble salts, water soluble salts, water treatment materials, waxes, and yeasts.

As noted herein, one or more of these additional active ingredients can be used in place of the heating agent in the microencapsulated delivery vehicle; that is, the active ingredient can be an active ingredient other than a heating agent.

One particular active agent that can be used in place of a heating agent as the active material in the microencapsulated delivery vehicle is a cooling agent. In many situations it may be beneficial to provide a product that is capable of providing a cooling sensation on the skin to soothe and relieve skin irritation, or to relax muscles. Some situations that may require a cooling sensation on the skin include, for example, sore muscles, sunburned skin, skin over-heated from exercise, hemorrhoids, minor scrapes and burns, and the like. Specific products that may include a cooling agent include, for example, spa gloves and socks, foot creams and wraps, cooling moist bath tissue, topical analgesics, cooling lotions, cooling acne cloths, sunburn relief gels and creams, cooling suntan lotions, cooling insect bite relief sprays and/or lotions, cooling diaper rash creams, cooling anti-irritation/anti-inflammatory creams, and cooling eye patches.

Suitable cooling agents are chemical compounds that have a negative heat of solution; that is, suitable cooling agents are chemical compounds that when dissolved in water feel cool due to an endothermic chemical reaction. Some suitable cooling agents for inclusion in the microencapsulated heat delivery vehicle include, for example, ammonium nitrate, sodium chloride, potassium chloride, xylitol, barium hydroxide ($Ba(OH)_2.8H_2O$), barium oxide ($BaO.9H_2O$), magnesium potassium sulfate ($MgSO_4.K_2SO_4.6H_2O$), potassium aluminum sulfate ($KAl(SO_4)_2.12H_2O$), sodium borate (tetra) ($Na_2B_4O_7.10H_2O$), sodium phosphate ($Na_2HPO_4.12H_2O$), and combinations thereof. Similar to the heating agents described herein, in some embodiments, the cooling agent may be surrounded by a hydrophobic wax material prior to being incorporated into the matrix material.

As noted above, the microencapsulated heat (or other active agent, such as a cooling agent, for example, alone or in combination with a heating agent) delivery vehicles as described herein are suitable for use in a number of products, including wipe products, wraps, such as medical wraps and bandages, headbands, wristbands, helmet pads, personal care products, cleansers, lotions, emulsions, oils, ointments, salves, balms, and the like. Although described primarily herein in relation the wipes, it will be recognized by one skilled in the art that the microencapsulated delivery vehicles described herein could be incorporated into any one or more of the other products listed above.

Generally, the wipes of the present disclosure including the microencapsulated heat delivery vehicles can be wet wipes or dry wipes. As used herein, the term "wet wipe" means a wipe that includes greater than about 70% (by weight substrate) moisture content. As used herein, the term "dry wipe" means a wipe that includes less than about 10% (by weight substrate) moisture content. Specifically, suitable wipes for use in the present disclosure can include wet wipes, hand wipes, face wipes, cosmetic wipes, household wipes, industrial wipes, and the like. Particularly preferred wipes are wet wipes, and other wipe-types that include a solution.

Materials suitable for the substrate of the wipes are well know to those skilled in the art, and are typically made from a fibrous sheet material which may be either woven or nonwoven. For example, suitable materials for use in the wipes may include nonwoven fibrous sheet materials which include meltblown, coform, air-laid, bonded-carded web materials, hydroentangled materials, and combinations thereof. Such materials can be comprised of synthetic or natural fibers, or a combination thereof. Typically, the wipes of the present disclosure define a basis weight of from about 25 grams per square meter to about 120 grams per square meter and desirably from about 40 grams per square meter to about 90 grams per square meter.

In one particular embodiment, the wipes of the present disclosure comprise a coform basesheet of polymer fibers and absorbent fibers having a basis weight of from about 60 to about 80 grams per square meter and desirably about 75 grams per square meter. Such coform basesheets are manufactured generally as described in U.S. Pat. Nos. 4,100,324, issued to Anderson, et al. (Jul. 11, 1978); 5,284,703, issued to Everhart, et al. (Feb. 8, 1994); and 5,350,624, issued to Georger, et al. (Sep. 27, 1994), which are incorporated by reference to the extent to which they are consistent herewith. Typically, such coform basesheets comprise a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, Vistamaxx® elastic olefin copolymer resin designated PLTD-1810, available from ExxonMobil Corporation (Houston, Tex.) or KRATON G-2755, available from Kraton Polymers (Houston, Tex.) may be used to provide stretchable polymeric meltblown fibers for the coform basesheets. Other suitable polymeric materials or combinations thereof may alternatively be utilized as known in the art.

As noted above, the coform basesheet additionally may comprise various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. of Federal Way (Wash.); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

The relative percentages of the polymeric meltblown fibers and cellulosic fibers in the coform basesheet can vary over a wide range depending upon the desired characteristics of the wipes. For example, the coform basesheet may comprise from about 10 weight percent to about 90 weight percent, desirably from about 20 weight percent to about 60 weight percent, and more desirably from about 25 weight percent to about 35 weight percent of the polymeric meltblown fibers based on the dry weight of the coform basesheet being used to provide the wipes.

In an alternative embodiment, the wipes of the present disclosure can comprise a composite which includes multiple layers of materials. For example, the wipes may include a three layer composite which includes an elastomeric film or meltblown layer between two coform layers as described above. In such a configuration, the coform layers may define a basis weight of from about 15 grams per square meter to about 30 grams per square meter and the elastomeric layer may include a film material such as a polyethylene metallocene film. Such composites are manufactured generally as described in U.S. Pat. No. 6,946,413, issued to Lange, et al. (Sep. 20, 2005), which is hereby incorporated by reference to the extent it is consistent herewith.

In accordance with the present disclosure, the contents (i.e., heating agent) of the microencapsulated heat delivery vehicle as described herein are capable of generating heat to produce a warming sensation in the wipe upon being activated (i.e., ruptured) and wetted. In one embodiment, the wipe is a wet wipe comprising a wetting solution in addition to the fibrous sheet material and the microencapsulated heat delivery vehicle. When the microencapsulated heat delivery vehicle is ruptured, its contents contact the wetting solution of the wet wipe, and an exothermic reaction occurs, thereby warming the wipe. The wetting solution can be any wetting solution known to one skilled in the wet wipe art. Generally, the wetting solution can include water, emollients, surfactants, preservatives, chelating agents, pH adjusting agents, skin conditioners, fragrances, and combinations thereof. For example, one suitable wetting solution for use in the wet wipe of the present disclosure comprises about 98% (by weight) water, about 0.6% (by weight) surfactant, about 0.3% (by weight) humectant, about 0.3% (by weight) emulsifier, about 0.2% (by weight) chelating agent, about 0.35% (by weight) preservative, about 0.002% (by weight) skin conditioning agent, about 0.03% (by weight) fragrance, and about 0.07% (by weight) pH adjusting agent. One specific wetting solution suitable for use in the wet wipe of the present disclosure is described in U.S. Pat. No. 6,673,358, issued to Cole et al. (Jan. 6, 2004), which is incorporated herein by reference to the extent it is consistent herewith.

In another embodiment, the wipe is a dry wipe. In this embodiment, the wipe can be wetted with an aqueous solution just prior to, or at the point of, use of the wipe. The aqueous solution can be any aqueous solution known in the art to be suitable for use in wipe products. Generally, the aqueous solution includes mainly water, and can further include additional components, such as cleansers, lotions, preservatives, fragrances, surfactants, emulsifiers, and combinations thereof. Once the wipe is wetted with the aqueous solution and the contents of the microencapsulated heat delivery vehicle contact the aqueous solution, an exothermic reaction similar to the wet wipe embodiment above is produced, thereby warming the wipe.

It has been determined that the ideal temperature for a wipe to be utilized is a temperature of from about 30° C. to about 40° C. (86° F.-104° F.). A conventional wipe will typically be stored at room temperature (about 23° C. (73.4° F.). As such, when the microencapsulated heat delivery vehicle ruptures, and releases its contents, and the contents contact an aqueous solution, a warming sensation is produced, increasing the temperature of the solution and wipe by at least about 5° C. More suitably, the temperature of the solution and wipe is increased by at least about 10° C., even more suitably, increased by at least about 15° C., and even more suitably increased by at least about 20° C. or more.

Generally, the elapsed time between the dispensing of a wipe product and use of the product is about 2 seconds or less, and typically is about 6 seconds or less. As such, once the microencapsulated heat delivery vehicle of the present disclosure is ruptured and its contents contacted by water, the contents of the microencapsulated heat delivery vehicle begin to generate heat and a warming sensation is suitably perceived in less than about 20 seconds. More suitably, the warming sensation is perceived in less than about 10 seconds, even more suitably, in less than about 5 seconds, and even more suitably, in less than about 2 seconds.

Additionally, once the warming sensation begins, the warming sensation of the wipe product is suitably maintained for at least about 5 seconds. More suitably, the warming sensation is maintained for at least about 8 seconds, even more suitably for at least about 15 seconds, even more suitably for at least about 20 seconds, even more suitably for at least about 40 seconds, and even more suitably for at least about 1 minute.

To generate the temperature increase described above, the wipes of the present disclosure suitably comprise from about 0.33 grams per square meter to about 500 grams per square meter microencapsulated heat delivery vehicle. More suitably, the wipes comprise from about 6.0 grams per square meter to about 175 grams per square meter microencapsulated heat delivery vehicle, even more suitably from about 16 grams per square meter to about 90 grams per square meter, and even more suitably, from about 30 grams per square meter to about 75 grams per square meter microencapsulated heat delivery vehicle.

The microencapsulated heat delivery vehicle can be applied to the wipe using any means known to one skilled in the art. Preferably, the microencapsulated heat delivery vehicle is embedded into the core of the fibrous sheet material of the wipe. By embedding the microencapsulated heat delivery vehicle into the core of the fibrous sheet material, the wipe will have a reduced grittiness feel because of a cushion effect and the ruptured shells of the microencapsulated heat delivery vehicle will not come into direct contact with the user's skin. Additionally, when the microencapsulated heat delivery vehicle is located in the core of the fibrous sheet material, the microencapsulated heat delivery vehicle is better protected from premature heat release caused by the conditions of manufacturing, storage, and transportation of the wipe.

In one embodiment, the microencapsulated heat delivery vehicle is embedded inside of the fibrous sheet material. For example, in one specific embodiment, the fibrous sheet material is one or more meltblown layers made by providing a stream of extruded molten polymeric fibers. To incorporate the microencapsulated heat delivery vehicles, a stream of microencapsulated heat delivery vehicles can be merged with the stream of extruded molten polymeric fibers and collected on a forming surface such as a forming belt or forming drum to form the wipe comprising the microencapsulated heat delivery vehicle. Optionally, a forming layer can be placed on the forming surface and used to collect the microencapsulated heat delivery vehicles in the wipe. By using this method, the microencapsulated heat delivery vehicle is mechanically entrapped within the forming layer.

The stream of meltblown polymeric fibers may be provided by meltblowing a copolymer resin or other polymer. For example, in one embodiment, the melt temperature for a copolymer resin such as Vistamaxx® PLTD 1810 can be from about 450° F. (232° C.) to about 540° F. (282° C.). As noted above, suitable techniques for producing nonwoven fibrous webs, which include meltblown fibers, are described in the previously incorporated U.S. Pat. Nos. 4,100,324 and 5,350,624. The meltblowing techniques can be readily adjusted in accordance with the knowledge of one skilled in the art to provide turbulent flows that can operatively intermix the fibers and the microencapsulated heat delivery vehicles. For example, the primary air pressure may be set at 5 pounds per square inch (psi) and the meltblown nozzles may be 0.020 inch spinneret hole nozzles.

Additionally, immediately following the formation of the meltblown structure, the meltblown polymeric fibers can be tacky, which can be adjusted to provide additional adhesiveness between the fibers and the microencapsulated heat delivery vehicles.

In another embodiment, the fibrous sheet material is a coform basesheet comprising a matrix of thermoplastic polymeric meltblown fibers and absorbent cellulosic fibers. Similar to the meltblown embodiment above, when the fibrous sheet material is a matrix of thermoplastic polymeric meltblown fibers and absorbent cellulosic fibers, a stream of microencapsulated heat delivery vehicles can be merged with a stream of cellulosic fibers and a stream of polymeric fibers into a single stream and collected on a forming surface such as a forming belt or forming drum to form a wipe comprising a fibrous sheet material with the microencapsulated heat delivery vehicles within its core.

The stream of absorbent cellulosic fibers may be provided by feeding a pulp sheet into a fiberizer, hammermill, or similar device as is known in the art. Suitable fiberizers are available from Hollingsworth (Greenville, S.C.) and are described in U.S. Pat. No. 4,375,448, issued to Appel, et al. (Mar. 1, 1983), which is incorporated by reference to the extent to which it is consistent herewith. The stream of polymeric fibers can be provided as described above.

The thickness of the fibrous sheet material will typically depend upon the diameter size of the microencapsulated heat delivery vehicle, the fibrous sheet material basis weight, and the microencapsulated heat delivery vehicle loading. For example, as the size of the microencapsulated heat delivery vehicle is increased, the fibrous sheet material must be thicker to prevent the wipe from having a gritty feel.

In another embodiment, the fibrous sheet material is made up of more than one layer. For example, when the fibrous sheet material is a meltblown material, the fibrous sheet material can suitably be made up of two meltblown layers secured together, more suitably three meltblown layers, even more suitably four meltblown layers, and even more suitably five or more meltblown layers. When the fibrous sheet material is a coform basesheet, the fibrous sheet material can suitably be made up of two coform basesheet layers secured together, more suitably three coform basesheet layers, even more suitably four coform basesheet layers, even more suitably five or more coform basesheet layers. Moreover, when the fibrous sheet material includes a film, the fibrous sheet material can suitably be made up of two film layers, more suitably three film layers, even more suitably four film layers, and even more suitably five or more film layers. In one embodiment, the layers are separate layers. In another embodiment, the layers are plied together.

Using the additional layers will allow for improved capture of the microencapsulated heat delivery vehicle. This helps to ensure the microencapsulated heat delivery vehicle will remain in the wipe during shipping and storage. Additionally, as the microencapsulated heat delivery vehicle becomes further entrapped in the fibrous sheet material, the grittiness of the wipe is reduced.

To incorporate the microencapsulated heat delivery vehicle in between the layers of fibrous sheet material, the microencapsulated heat delivery vehicle is sandwiched between a first layer and a second layer of the fibrous sheet material, and the layers are then laminated together using any means known in the art. For example, the layers can be secured together thermally or by a suitable laminating adhesive composition.

Thermal bonding includes continuous or discontinuous bonding using a heated roll. Point bonding is one suitable example of such a technique. Thermal bonds should also be understood to include various ultrasonic, microwave, and other bonding methods wherein the heat is generated in the non-woven or the film.

In a preferred embodiment, the first layer and second layer are laminated together using a water insoluble adhesive composition. Suitable water insoluble adhesive compositions can include hot melt adhesives and latex adhesives as described in U.S. Pat. Nos. 6,550,633, issued to Huang, et al. (Apr. 22, 2003); 6,838,154, issued to Anderson, et al. (Oct. 25, 2005); and 6,958,103, issued to Varona et al. (Jan. 4, 2005), which are hereby incorporated by reference to the extent they are consistent herewith. Suitable hot melt adhesives can include, for example, RT 2730 APAO and RT 2715 APAO, which are amorphous polyalphaolefin adhesives (commercially available from Huntsman Polymers Corporation, Odessa, Tex.) and H2800, H2727A, and H2525A, which are all styrenic block copolymers (commercially available from Bostik Findley, Inc., Wauwatosa, Wis.). Suitable latex adhesives include, for example, DUR-O-SET E-200 (commercially available from National Starch and Chemical Co., Ltd., Bridgewater, N.J.) and Hycar 26684 (commercially available from B. F. Goodrich, Laval, Quebec).

The water insoluble adhesive composition can additionally be used in combination with the microencapsulated heat delivery vehicle between the first and second layers of the fibrous sheet material. The water insoluble adhesive composition will provide improved binding of the microencapsulated heat delivery vehicle to the first and second layers of the fibrous sheet material. Typically, the adhesive composition can be applied to the desired area by spraying, knifing, roller coating, or any other means suitable in the art for applying adhesive compositions.

Suitably, the adhesive composition can be applied to the desired area of the wipe in an amount of from about 0.01 grams per square meter to about 20 grams per square meter. More suitably, the adhesive composition can be applied in an amount of from about 0.05 grams per square meter to about 0.5 grams per square meter.

In yet another embodiment, the microencapsulated heat delivery vehicle may be distributed within a pocket of the fibrous sheet material. Similar to the pattern distribution method described herein below, the pockets of microencapsulated heat delivery vehicles provide for a targeted warming sensation in the wipe.

As an alternative to embedding the microencapsulated heat delivery vehicles into the core of the fibrous sheet material, the microencapsulated heat delivery vehicles can be deposited on the outer surface of the fibrous sheet material. In one embodiment, the microencapsulated heat delivery vehicles are deposited on one outer surface of the fibrous sheet material. In another embodiment, the microencapsulated heat delivery vehicles are deposited on both outer surfaces of the fibrous sheet material.

To provide for better attachment of the microencapsulated heat delivery vehicles to the outer surface of the fibrous sheet material, a water insoluble adhesive composition can be applied with the microencapsulated heat delivery vehicles onto the outer surface of the fibrous sheet material. Suitable water insoluble adhesive compositions are described herein above. Suitably, the adhesive composition can be applied to the outer surface of the fibrous sheet material in an amount of from about 0.01 grams per square meter to about 20 grams per square meter. More suitably, the adhesive composition can be applied in an amount of from about 0.05 grams per square meter to about 0.5 grams per square meter.

The microencapsulated heat delivery vehicles may be embedded in or distributed on the fibrous sheet material in a continuous layer or a patterned layer. By using a patterned layer, a targeted warming sensation can be achieved. These methods of distribution can additionally reduce manufacturing costs as reduced amounts of microencapsulated heat delivery vehicles are required. Suitably, the microencapsulated heat delivery vehicles can be distributed in patterns including, for example, characters, an array of separate lines, swirls, numbers, or dots of microencapsulated heat delivery vehicles. Continuous patterns, such as stripes or separate lines that run parallel with the machine direction of the web, are particularly preferred as these patterns may be more process-friendly.

Additionally, the microencapsulated heat delivery vehicles may be colored using a coloring agent prior to applying the microencapsulated heat delivery vehicles to the fibrous sheet material. The coloring of the microencapsulated heat delivery vehicles can improve the aesthetics of the wipe. Additionally, in embodiments where targeted warming is desired, the coloring of the microencapsulated heat delivery vehicles can direct the consumer of the wipe product to the location of the microencapsulated heat delivery vehicles in the wipe.

Suitable coloring agents include, for example, dyes, color additives, and pigments or lakes. Suitable dyes include, for example, Blue 1, Blue 4, Brown 1, External Violet 2, External Violet 7, Green 3, Green 5, Green 8, Orange 4, Orange 5, Orange 10, Orange 11, Red 4, Red 6, Red 7, Red 17, Red 21, Red 22, Red 27, Red 28, Red 30, Red 31, Red 33, Red 34, Red 36, Red 40, Violet 2, Yellow 5, Yellow 6, Yellow 7, Yellow 8, Yellow 10, Yellow 11, Acid Red 195, Anthocyanins, Beetroot Red, Bromocresol Green, Bromothymol Blue, Capsanthin/Capsorubin, Curcumin, and Lactoflavin. Also, many dyes found suitable for use in the European Union and in Japan may be suitable for use as coloring agents in the present disclosure.

Suitable color additives include, for example, aluminum powder, annatto, bismuth citrate, bismuth oxychloride, bronze powder, caramel, carmine, beta carotene, chloraphyllin-copper complex, chromium hydroxide green, chromium oxide greens, copper powder, disodium EDTA-copper, ferric ammonium ferrocyanide, ferric ferrocyanide, guauazulene, guanine, henna, iron oxides, lead acetate, manganese violet, mica, pyrophylite, silver, titanium dioxide, ultramarines, zinc oxide, and combinations thereof.

Suitable pigments or lakes include, for example, Blue 1 Lake, External Yellow 7 Lake, Green 3 Lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 36 Lake, Red 40 Lake, Yellow 5 Lake, Yellow 6 Lake, Yellow 7 Lake, Yellow 10 Lake, and combinations thereof.

Any means known to one of skill in the art capable of producing sufficient force to break the capsules can be used in the present disclosure. In one embodiment, the microencapsulated heat delivery vehicles can be broken by the user at the point of dispensing the wipe from a package. For example, a mechanical device located inside of the package containing the wipes can produce a rupture force sufficient to rupture the capsules upon dispensing the wipe, thereby exposing the contents of the microencapsulated heat delivery vehicles.

In another embodiment, the capsules can be broken by the user just prior to or at the point of use of the wipe. By way of example, in one embodiment, the force produced by the hands of the user of the wipe can break the capsules, exposing the contents of the microencapsulated heat delivery vehicles.

Under certain conditions, such as in high ambient temperature conditions, the self-warming wipes of the present disclosure may be perceived by the user as uncomfortably warm. Conversely, the self-warming wipe may begin cooling prior to the end use of the wipe. Since the self-warming wipes are manufactured to provide a designated temperature rise, one or more phase change materials may optionally be included in the wipe to provide thermal stability to the wipe when the wipe is subjected to extreme heat.

The phase change materials use their heat of fusion to automatically regulate the temperature of the self-warming wipe. As well known in the art, "heat of fusion" is the heat in joules required to convert 1.0 gram of a material from its solid form to its liquid form at its melting temperature. Accordingly, if the contents of the microencapsulated heat delivery vehicle are activated and the temperature of the wipe reaches or exceeds the melting point of the phase change material, the phase change material will liquefy, thereby absorbing the heat from the wipe. Once the wipe begins to cool, the phase change material will resolidify by releasing the absorbed heat. In one embodiment, to provide thermal stability to the wipe, the phase change material can suitably liquefy and resolidify for one cycle. In another embodiment, such as during transportation where the temperature of the wipe can fluctuate, the phase change material undergoes multiple cycles of liquefying and resolidifying.

Suitably, the wipes of the present disclosure may comprise one or more phase change materials for regulating the temperature of the wipe. In one specific embodiment, the wipe comprises a first phase change material. In another embodiment, the wipe comprises a first phase change material and a second phase change material.

As noted above, the ideal temperature for the wipes of the present disclosure is a temperature of from about 30° C. to about 40° C. (86° F.-104° F.). As such, suitable phase change materials for use as the first phase change material have a melting point of from about 22° C. to about 50° C. More suitably, the first phase change material has a melting point of from about 30° C. to about 40° C., and even more suitably about 35° C.

Additionally, the first phase change materials have a heat of fusion suitable for regulating the temperature of the self-warming wipes of the present disclosure. Suitably, the first phase change materials have a heat of fusion of from about 8.0 joules/gram to about 380 joules/gram. More suitably, the first phase change materials have a heat of fusion of from about 100 joules/gram to about 380 joules/gram.

Suitable materials for use as the first phase change materials include, for example, n-Tetracosane, n-Tricosane, n-Docosane, n-Heneicosane, n-Eicosane, n-Nonadecane, n-Octadecane, n-Heptadecane, and combinations thereof.

In one embodiment, a second phase change material can be included to provide additional protection against the wipe becoming too hot. The second phase change material is different than the first phase change material. For example, the second phase change material typically has a higher melting point as compared to the first phase change material. By having a higher melting point, the second phase change materials are capable of absorbing heat at a higher temperature level, and as such can provide improved protection against thermal discomfort of the skin. Specifically, the second phase change materials suitably have a melting point of from about 50° C. to about 65° C., more suitably, from about 50° C. to about 60° C.

Suitable materials for the second phase change materials include, for example, n-Octacosane, n-Heptacosane, n-Hexacosane, n-Pentacosane, and combinations thereof.

Any of the phase change materials described above can be introduced into the wipe in solid or liquid form. For example, in one embodiment, the phase change materials are in solid powder form or particles. Suitably, the phase change material particles have a particle size of from about 1.0 micrometers to about 700 micrometers. More suitably, the phase change material particles have a particle size of from about 300 micrometers to about 500 micrometers.

In one embodiment, the phase change material particles can be microencapsulated. Generally, the phase change material particles can be microencapsulated using any method known in the art. In one preferred embodiment, the phase change material particles are microencapsulated using the alginate encapsulation method described above for the microencapsulated heat delivery vehicles. In another embodiment, the phase change material particles are microencapsulated using the fluid bed coating described above for the microencapsulated heat delivery vehicles. Other suitable means of encapsulating the phase change material particles can include, for example, pan coating, annular-jet encapsulation, complex coacervation, spinning-disk coating, and combinations thereof.

The microencapsulation shell thickness may vary depending upon the phase change material utilized, and is generally manufactured to allow the encapsulated phase change material particle to be covered by a thin layer of encapsulation material, which may be a monolayer or thicker laminate layer, or may be a composite layer. The microencapsulation layer should be thick enough to resist cracking or breaking of the shell during handling or shipping of the product. The microencapsulation layer should also be constructed such that atmospheric conditions during manufacturing, storage, and/or shipment will not cause a breakdown of the microencapsulation layer and result in a release of the phase change material.

In another embodiment, the phase change material is in liquid form, specifically, in a liquid coating composition. To produce the liquid coating composition, the phase change material, preferably in a pure powder form is combined with an aqueous solution. The solution is then heated to a temperature above the phase change material melting point and stirred to shear the phase change material to form the liquid coating composition comprising the liquid phase change material. In one specific embodiment, the aqueous solution can be the wetting solution of a wet wipe described herein above.

In one embodiment, once the liquid coating composition is applied to the fibrous sheet material of the wipe, the composition dries and the phase change materials solidify into small particles that are distributed throughout the fibrous sheet material of the wipe.

The liquid coating composition may optionally comprise additional components to improve the properties, such as spreadability and adhesiveness, of the composition. For example, in one embodiment, the liquid coating composition can comprise a tackifier. Using a tackifier will improve the binding of the liquid coating composition, and in particular the phase change material, to the fibrous sheet material.

Typically, the phase change material can be embedded inside of the fibrous sheet material or deposited onto the outer surface of the fibrous sheet material. In one embodiment, the phase change material is embedded inside of the fibrous sheet material. The phase change material can be embedded into the core of the fibrous sheet material using any method described above for embedding the microencapsulated heat delivery vehicles into the core.

In another embodiment, the phase change material can be deposited on an outer surface of the fibrous sheet material. Typically, the phase change material can be deposited on an outer surface of the fibrous sheet material using any method described above for depositing the microencapsulated heat delivery vehicles on an outer surface of the fibrous sheet material. Similar to the microencapsulated heat delivery vehicles, when depositing the phase change material, the phase change material can be deposited on one outer surface of the fibrous sheet material, or the phase change material can be applied to both outer surfaces of the fibrous sheet material.

In addition to the methods of application described above, the phase change materials described herein can be applied to the desired area of the fibrous sheet material using the methods of spray coating, slot coating and printing, or a combination thereof. In slot coating, the phase change material is introduced directly onto or into the desired area of the fibrous sheet material in "slots," discrete row patterns, or other patterns. Similar to applying the microencapsulated heat delivery vehicle in patterns described above, slot coating may be advantageous in certain applications where it is not desirable to coat the entire fibrous sheet material with a phase change material.

The phase change material should suitably be applied to the fibrous sheet material similar to the microencapsulated heat delivery vehicle. Specifically, when the microencapsulated heat delivery vehicle is applied in a continuous layer, the phase change material should be applied in a continuous layer. Likewise, when the microencapsulated heat delivery vehicle is applied in a patterned layer, the phase change material should be applied in a patterned layer. Suitable patterns for applying the phase change materials are those patterns described above for the microencapsulated heat delivery vehicles. Specifically, the phase change materials can be applied in the patterns including, for example, stripes, characters, swirls, numbers, dots, and combinations thereof. Applying the phase change material in a similar manner as the microencapsulated heat delivery vehicle will allow for the phase change material to more easily and efficiently absorb the heat generated by the microencapsulated heat delivery vehicle, thus, providing better protection against thermal discomfort to the user of the wipe.

The amount of phase change material to be applied to the fibrous sheet material will depend upon the desired temperature increase of the wipe, the type of microencapsulated heat delivery vehicle used, the amount of microencapsulated heat delivery vehicle used, and the type of phase change material used. In one embodiment, when all of the heat generated by the heating agent is absorbed by the wipe, the formula for calculating the amount of phase change material required for use in the wipe is as follows:

$$m_{(PCM)} = [\Delta H_{(HA)} \times m_{(HA)}]/\Delta H_{(PCM)}$$

wherein $m_{(PCM)}$ is the required mass of phase change material; $\Delta H_{(HA)}$ is the heat of solution or the heat generated by the microencapsulated heat delivery vehicle, per unit mass; $m_{(HA)}$ is the mass of the microencapsulated heat delivery vehicle used; and $\Delta H_{(PCM)}$ is the heat of fusion of the phase change material, per unit mass.

As noted above, in one specific embodiment, the microencapsulated heat delivery vehicles as described herein are suitable for combination with a biocide agent for use in cleansing compositions, which may be used alone, or in combination with a cleansing product such as a wipe. Generally, the cleansing composition includes the microencapsulated heat delivery vehicle as described above and a biocide agent and is suitable for cleaning both animate and inanimate surfaces.

Using the microencapsulated heat delivery vehicles in the cleansing composition in combination with the biocide agents results in an increased biocidal effect when the microencapsulated heat delivery vehicles are activated. Specifically, the increase in temperature has been found to activate or enhance the function of the biocide agents present in the cleansing composition.

Generally, the three main factors affecting the efficacy of biocide agents include: (1) mass transfer of biocide agents in the cleansing composition to the microbe-water interface; (2) chemisorption of biocide agents to the cell wall or cell membrane of the microbes; and (3) diffusion of the activated chemisorbed biocide agent into the cell of the microbe. It has been found that temperature is a primary regulator of all three factors. For example, the lipid bilayer cell membrane structure of many microbes "melts" at higher than room temperatures, allowing holes to form in the membrane structure. These holes can allow the biocide agent to more easily diffuse through the microbe cell wall or membrane and enter the cell.

Generally, the cleansing compositions of the present disclosure are capable of killing or substantially inhibiting the growth of microbes. Specifically, the biocide agent of the cleansing compositions interfaces with either the reproductive or metabolic pathways of the microbes to kill or inhibit the growth of the microbes.

Microbes suitably affected by the biocide agents of the cleansing composition include viruses, bacteria, fungi, and protozoans. Viruses that can be affected by the biocide agents include, for example, Influenza, Parainfluenza, Rhinovirus, Human Immunodeficiency Virus, Hepatitis A, Hepatitis B, Hepatitis C, Rotavirus, Norovirus, Herpes, Coronavirus, and Hanta virus. Both gram positive and gram negative bacteria are affected by the biocide agents of the cleansing composition. Specifically, bacteria affected by the biocide agents used in the cleansing compositions include, for example, *Staphylococcus aureus, Streptococcus pneumoniae, Streptococcus pyogenes, Pseudomonas aeruginose, Klebsiella pneumoniae, Escherichia coli, Enterobacter aerogenes, Enterococcus faecalis, Bacillus subtilis, Salmonella typhi, Mycobacterium tuberculosis*, and *Acinetobacter baumannii*. Fungi affected by the biocide agents include, for example, *Candida albicans, Aspergillus niger*, and *Aspergillus fumigates*. Protozoans affected by the biocide agents include, for example, *cyclospora cayetanensis, Cryptosporidum parvum*, and species of microsporidum.

Suitable biocide agents for use in the cleansing compositions include, for example, isothiazolones, alkyl dimethyl ammonium chloride, triazines, 2-thiocyanomethylthio benzothiazol, methylene bis thiocyanate, acrolein, dodecylguanidine hydrochloride, chlorophenols, quarternary ammonium salts, gluteraldehyde, dithiocarbamates, 2-mercaptobenzothiazole, para-chloro-meta-xylenol, silver, chlorohexidine, polyhexamethylene biguanide, n-halamines, triclosan, phospholipids, alpha hydroxyl acids, 2,2-dibromo-3-nitrilopropionamide, 2-bromo-2-nitro-1,3-propanediol, farnesol, iodine, bromine, hydrogen peroxide, chlorine dioxide, alcohols, ozone, botanical oils (e.g., tee tree oil and rosemary oil), botanical extracts, benzalkonium chloride, chlorine, sodium hypochlorite, and combinations thereof.

The cleansing compositions of the present disclosure may also optionally contain a variety of other components which may assist in providing the desired cleaning properties. For example, additional components may include non-antagonistic emollients, surfactants, preservatives, chelating agents, pH adjusting agents, fragrances, moisturizing agents, skin benefit agents (e.g., aloe and vitamin E), antimicrobial actives, acids, alcohols, or combinations or mixtures thereof. The composition may also contain lotions, and/or medicaments to deliver any number of cosmetic and/or drug ingredients to improve performance.

The cleansing compositions of the present disclosure are typically in solution form and include water in an amount of about 98% (by weight). The solution can suitably be applied alone as a spray, lotion, foam, or cream.

When used as a solution, the biocide agents are typically present in the cleansing composition in an amount of from about $3.0 \times 10^{-6}$% (by weight) to about 95% (by weight). Suitably, the biocide agents are present in the cleansing composition in an amount of from about 0.001% (by weight) to about 70.0% (by weight), even more suitably from about 0.001% (by weight) to about 10% (by weight), and even more suitably in an amount of from about 0.001% (by weight) to about 2.0% (by weight).

When used in combination with the biocide agent in the solution of cleansing composition, the microencapsulated heat delivery vehicles as described above are suitably present in the cleansing compositions in an amount of from about 0.05% (by weight cleansing composition) to about 25% (by weight cleansing composition). More suitably, the microencapsulated heat delivery vehicles are present in the cleansing compositions in an amount of from about 1.0% (by weight cleansing composition) to about 25% (by weight cleansing composition).

In another embodiment, the cleansing composition is incorporated into a substrate which can be a woven web, non-woven web, spunbonded fabric, meltblown fabric, knit fabric, wet laid fabric, needle punched web, cellulosic material or web, and combinations thereof, for example, to create products such as hand towels, bathroom tissue, dry wipes, wet wipes, and the like. In one preferred embodiment, the cleansing composition is incorporated into the wet wipe described above.

Typically, to manufacture the wet wipe with the cleansing composition, the microencapsulated heat delivery vehicle and biocide agent can be embedded inside of the fibrous sheet material or deposited on the outer surface of the fibrous sheet material. In one embodiment, the microencapsulated heat delivery vehicle and biocide agent are both embedded inside of the fibrous sheet material. The microencapsulated heat delivery vehicle can be embedded inside of the fibrous sheet material as described above. Additionally, the biocide agent can be embedded inside of the fibrous sheet material using any method described above for embedding the microencapsulated heat delivery vehicle into the core.

In another embodiment, both the microencapsulated heat delivery vehicle and the biocide agent are deposited on an outer surface of the fibrous sheet material. The microencapsulated heat delivery vehicle can be deposited on one or both outer surfaces of the fibrous sheet material as described above. Typically, the biocide agent can be deposited on an outer surface of the fibrous sheet material using any method described above for depositing the microencapsulated heat delivery vehicle on an outer surface of the fibrous sheet material. Similar to the microencapsulated heat delivery vehicle, when depositing the biocide agent, the biocide agent can be deposited on one outer surface of the fibrous sheet material, or the biocide agent can be applied to both outer surfaces of the fibrous sheet material.

In yet another embodiment, the microencapsulated heat delivery vehicle can be embedded into the core of the fibrous sheet material using any method described above and the biocide agent can be deposited on one or both outer surfaces of the fibrous sheet material using any method described above.

In addition to the methods of application described above, the biocide agents described herein can be applied to the desired area of the fibrous sheet material using the methods of spray coating, slot coating and printing, and combinations thereof.

In one embodiment, the biocide agents can be microencapsulated in a shell material prior to being introduced into or onto the fibrous sheet material. Generally, the biocide agent can be microencapsulated using any method known in the art. Suitable microencapsulation shell materials include cellulose-based polymeric materials (e.g., ethyl cellulose), carbohydrate-based materials (e.g., cationic starches and sugars) and materials derived therefrom (e.g., dextrins and cyclodextrins) as well as other materials compatible with human tissues.

The microencapsulation shell thickness may vary depending upon the biocide agent utilized, and is generally manufactured to allow the encapsulated formulation or component to be covered by a thin layer of encapsulation material, which may be a monolayer or thicker laminate layer, or may be a composite layer. The microencapsulation layer should be thick enough to resist cracking or breaking of the shell during handling or shipping of the product. The microencapsulation layer should also be constructed such that atmospheric conditions during manufacturing, storage, and/or shipment will not cause a breakdown of the microencapsulation layer and result in a release of the biocide agent.

Microencapsulated biocide agents applied to the outer surface of the wipes as discussed above should be of a size such that the user cannot feel the encapsulated shell on the skin during use. Typically, the capsules have a diameter of no more than about 25 micrometers, and desirably no more than about 10 micrometers. At these sizes, there is no "gritty" or "scratchy" feeling on the skin when the wipe is utilized.

When used in a product such as a wipe, the microencapsulated heat delivery vehicles are present in the fibrous sheet material in an amount suitably of from about 0.33 grams per square meter to about 500 grams per square meter microencapsulated heat delivery vehicle. More suitably, the wipes comprise from about 6 grams per square meter to about 175 grams per square meter microencapsulated heat delivery vehicle, and even more suitably, from about 16 grams per square meter to about 75 grams per square meter microencapsulated heat delivery vehicle.

Suitably, the biocide agent is present in the fibrous sheet material of the wet wipe in an amount of suitably 0.01 grams per square meter to about 50 grams per square meter. More suitably, the biocide agent is present in the fibrous sheet material in an amount of from about 0.01 grams per square meter to about 25 grams per square meter, and even more suitably, in an amount of from about 0.01 grams per square meter to about 0.1 grams per square meter.

The present disclosure is illustrated by the following examples which are merely for the purpose of illustration and are not to be regarded as limiting the scope of the disclosure or manner in which it may be practiced.

EXAMPLE 1

In this example, samples incorporating various size ranges of anhydrous calcium chloride suspended in mineral oil at 35 wt % were evaluated for their ability to generate heat upon introduction into water.

The five size ranges of anhydrous calcium chloride evaluated were: (1) less than 149 microns; (2) 149-355 microns; (3) 710-1190 microns; (4) 1190-2000 microns; and (5) 2000-4000 microns. The samples of anhydrous calcium chloride (Dow Chemical, Midland, Mich.) were dispersed in mineral oil (available as Drakeol 7 LT NF from Penreco, Dickinson, Tex.). The as received anhydrous calcium chloride were screened dry using a Gilson Sonic Sieve (Gilson Company, Inc. Columbus, Ohio) to create two sizes, a 1190-2000 micron size and a 2000-4000 micron size. These powders were then suspended at 35 wt % in mineral oil to form a slurry using a cowles mixing blade. To achieve the smaller size distributions, the anhydrous calcium chloride powder required further processing.

Specifically, the sample of anhydrous calcium chloride having a size range of 710-1190 microns was produced by grinding the as received anhydrous calcium chloride with a size range of 2000-4000 microns in a hammermill, screening the powder to the desired size, and then suspending the calcium chloride particles at 35 wt % in mineral oil using a cowles mixing blade. The sample of anhydrous calcium chloride having a size range of 149-355 microns was produced by grinding the as received anhydrous calcium chloride with a size range of 2000-4000 microns in a hammermill, suspending the calcium chloride particles at 35 wt % in mineral oil using a cowles mixing blade and then further processing this slurry in a Buhler K8 media mill (Buhler, Inc. Switzerland). This media milling process used 0.5 millimeter alumina grinding media, and rotated at a speed of 1800 revolutions per minute (rpm), for 1.5 hours while slurry was pumped through the milling chamber. While being milled, 0.5 wt % surfactant, available as Antiterra 207 (BYK-Chemie, Wesel, Germany) was mixed with the anhydrous calcium chloride to control the viscosity. The sample of anhydrous calcium chloride having a size range of less than 149 microns was produced by grinding the as received anhydrous calcium chloride with a size range of 2000-4000 microns in a hammermill, suspending the calcium chloride particles at 35 wt % in mineral oil using a cowles mixing blade and then further processing this slurry in a Buhler K8 media mill (Buhler, Inc. Switzerland). This media milling process used 0.5 millimeter alumina grinding media, and rotated at a speed of 1800 revolutions per minute (rpm), for 2.5 hours while slurry was pumped through the milling chamber. While being milled, 0.5 wt % surfactant, available as Antiterra 207 (BYK-Chemie, Wesel, Germany) was mixed with the anhydrous calcium chloride to control the viscosity.

All five samples were then individually added to 7.0 grams de-ionized water and the resulting temperature rise was measured using a Barnant Scanning Thermocouple (available from Therm-X of California, Hayward, Calif.). The results are shown in FIG. 3.

Figure 3:
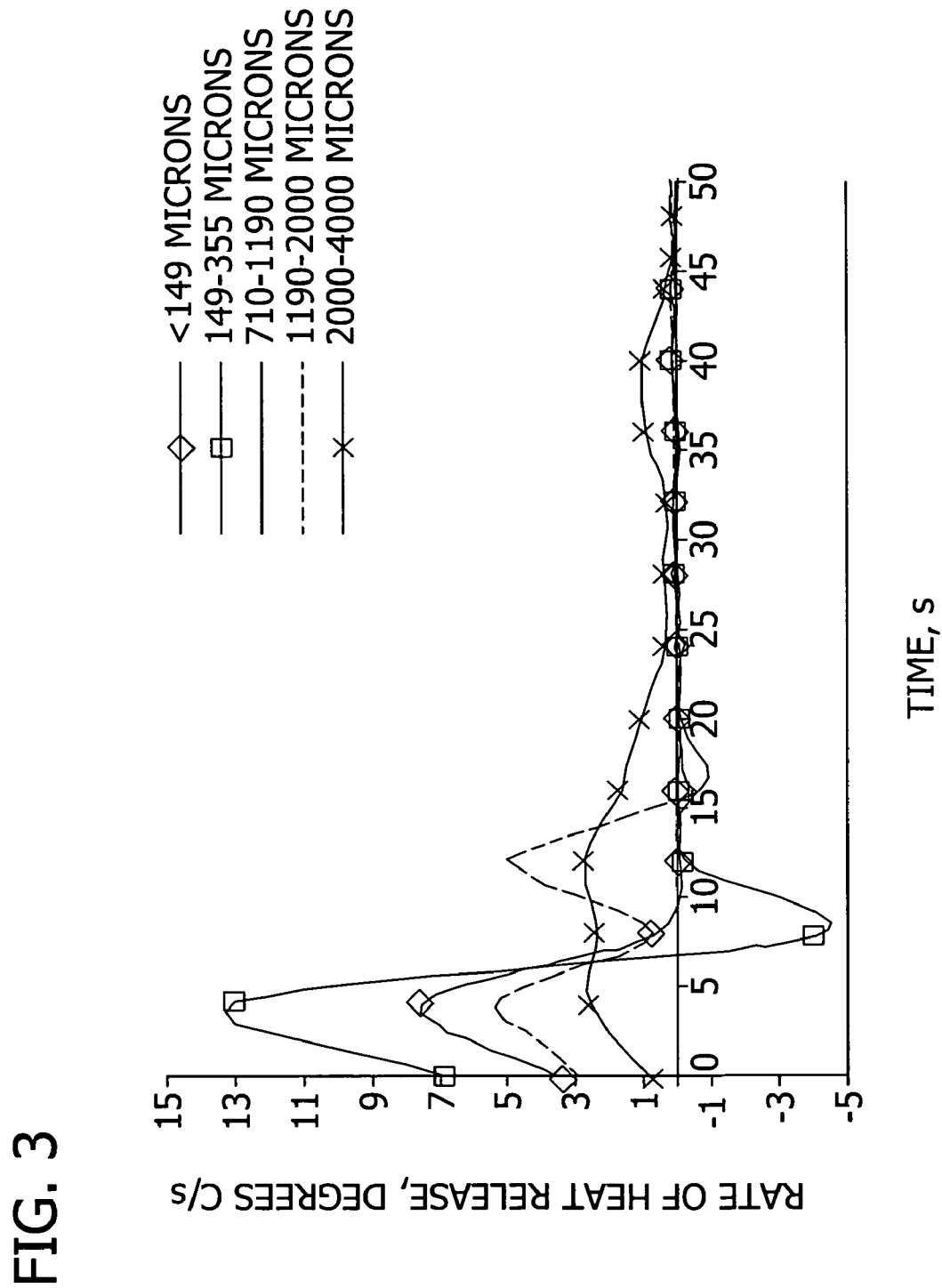
FIG. 3 is a graph illustrating the heat generation rate for five size ranges of calcium chloride that were tested in accordance with an experiment described herein.

As shown in FIG. 3, although all samples delivered an increase in the rate of heat release, the sample using anhydrous calcium chloride having a particle size in the range of 149-355 micrometers generated heat at the highest rate.

EXAMPLE 2

In this example, samples incorporating various size ranges of anhydrous magnesium chloride suspended in mineral oil at 35 wt % were evaluated for their ability to generate heat upon introduction into water.

The four size ranges of anhydrous magnesium chloride evaluated were: (1) 1000-1500 microns; (2) 600-1000 microns; (3) 250-600 microns; and (4) less than 250 microns. To produce the samples of anhydrous magnesium chloride in mineral oil, the various size ranges of anhydrous magnesium chloride powder (Magnesium Interface Inc. (Vancouver, B.C., Canada) were suspended at 35 wt % in mineral oil (available as Drakeol 7 LT NF from Penreco, Dickinson, Tex.). To produce the samples having anhydrous magnesium chloride with size ranges of 1000-1500 microns, 600-1000 microns, and 250-600 microns, the as received anhydrous magnesium chloride powder was hand screened into the size ranges desired and the powders collected. These powders were suspended at 35 wt % in mineral oil using a cowles mixing blade. The sample of anhydrous magnesium chloride having a size range of less than 250 microns was produced by coffee grinding (Mr. Coffee Grinder No. 10555, Hamilton Beach) the anhydrous magnesium chloride having a size range of 1000-1500 microns for 30 seconds to reduce the size. This sample was then processed using a Gilson Sonic Sieve (Gilson Company, Inc., Columbus, Ohio) to collect the particles having a particle size of less than 250 microns. This powder was suspend at 35 wt % in mineral oil using a cowles mixing blade.

All four samples were then added to 7.0 grams de-ionized water and the resulting temperature rise was measured using a J type Thermocouple (available from Omega Engineering, Inc., Stamford, Conn.). The results are shown in FIG. 4.

Figure 4:
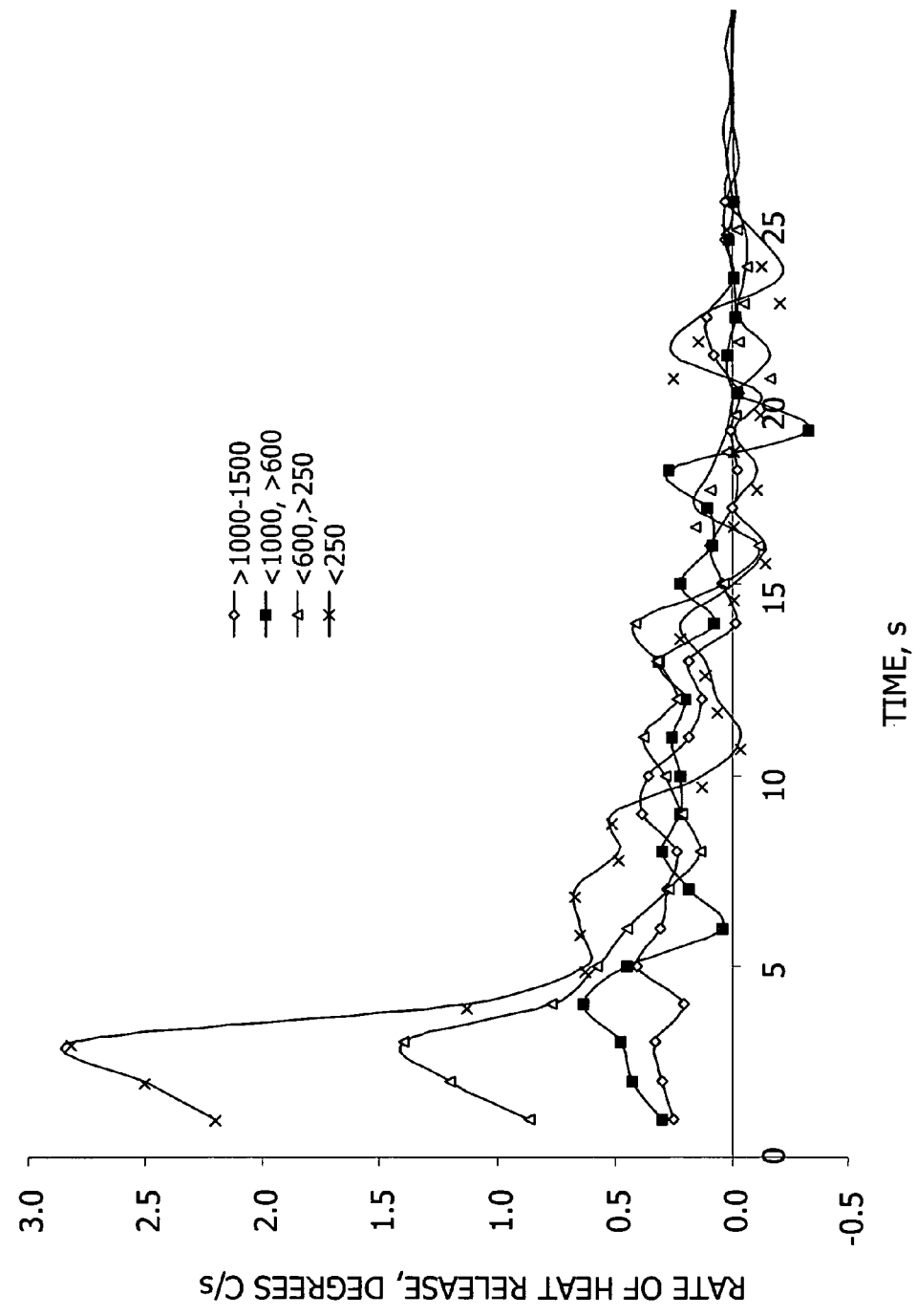
FIG. 4 is a graph illustrating the heat generation rate for four size ranges of magnesium chloride that were tested in accordance with an experiment described herein.

As shown in FIG. 4, although all samples delivered an increase in the rate of heat release, the sample using anhydrous magnesium chloride having a particle size of less than 250 micrometers generated heat at the highest rate.

EXAMPLE 3

In this Example, six compositions including a heating agent, matrix material, and various surfactants were produced. The viscosities (at 23° C.) of the compositions were measured using a Brookfield Viscometer to determine which surfactants were preferred for use in the compositions of the present disclosure.

To produce the compositions, 34.7% (by weight composition) anhydrous magnesium chloride (available from Magnesium Interface Inc., Vancouver, B.C., Canada), 64.3% (by weight composition) mineral oil (available as Drakeol 7 LT NF from Penreco, Dickinson, Tex.), and 1.0% surfactant (by weight composition) were milled together using a vertical attritor mill using one quarter inch, spherical, ceramic media for a total of 90 minutes. The surfactants utilized in the six compositions and their properties are shown in Table 1.

TABLE 1

| Surfactant | Commercial Source | Ionic Activity |
| --- | --- | --- |
| Antiterra 207 | BYK Chemie (Wesel, Germany) | Anionic |
| Disperbyk 166 | BYK Chemie (Wesel, Germany) | Proprietary |
| Disperbyk 162 | BYK Chemie (Wesel, Germany) | Cationic |
| BYK-P104 | BYK Chemie (Wesel, Germany) | Anionic |
| Tergitol TMN-6 | Union Carbide (Houston, Texas) | Non-ionic HLB = 11.7 |
| Span 85 | Uniqema/ICI Surfactants (Malaysia) | Non-ionic HLB = 1.8 |

The viscosities of the compositions (at 23° C.) were measured using a Brookfield Viscometer having a spindle rotating at 100 revolutions per minute (rpm). The results are shown in Table 2.

TABLE 2

| Surfactant | Viscosity at 23° C. (cP) | Spindle Number of Viscometer |
| --- | --- | --- |
| Antiterra 207 | 208 | RU3 |
| Disperbyk 166 | 208 | RU3 |
| Disperbyk 162 | 1366 | RU6 |
| BYK-P104 | 306 | RU3 |
| Tergitol TMN-6 | 7120 | RU6 |
| Span 85 | 352 | RU3 |

Samples with the lower viscosities are better suited for use in compositions utilized to make the microencapsulated heat delivery vehicles of the present disclosure as these compositions are easier to work with and allow for higher loading of heating agents. As such, as shown in Table 2, the compositions made with Antiterra 207 and BYK-P104 have the lowest viscosities, and as such, would be preferred surfactants for use in some of the compositions of the present disclosure. Moreover, the composition made with Tergitol TMN-6 had the highest viscosity and would thus be a less preferred surfactant for use in the compositions of the present disclosure.

EXAMPLE 4

In this Example a microencapsulated heat delivery vehicle was manufactured utilizing calcium chloride as both the encapsulating activator and the heating agent.

Calcium chloride (about 20 micrometers in diameter) was introduced into mineral oil (available as Drakeol 7 LT NF from Penreco, Dickinson, Tex.) to form a 25% (by weight) calcium chloride in mineral oil composition that was mixed together thoroughly and had a resulting viscosity (25° C.) of about 300 centipoise. This composition was introduced dropwise from a separatory funnel into two liters of an Manugel DMB aqueous sodium alginate solution (1% by weight in deionized water, 300 centipoise at 25° C., available from ISP Technologies, Inc., Scotland) and allowed to dwell in the solution for about 30 minutes under sufficient stirring to keep the drops formed upon addition into the sodium alginate solution separate. It is also significant to avoid overstirring, as this can cause high excess calcium release and alginate broth gelation. Most drops of the composition added were between about 3 millimeters in diameter and about 5 millimeters in diameter. After 30 minutes dwell time the formed microencapsulated beads were removed from the sodium alginate solution and rinsed three times with de-ionized water and cast to air-dry overnight at room-temperature. Stable microencapsulated heat delivery vehicles were formed.

EXAMPLE 5

In this Example a microencapsulated heat delivery vehicle including magnesium oxide was manufactured utilizing calcium chloride as the encapsulating activator.

Calcium chloride (about 20 micrometers in diameter) was introduced into 133 grams of propylene glycol and 70 grams of magnesium oxide to form a 3% (by weight) calcium chloride composition that was mixed together thoroughly and had a resulting viscosity (25° C.) of about 500 centipoise. This composition was introduced dropwise from a separatory funnel into two liters of an aqueous sodium alginate solution (1% by weight in de-ionized water, 250 centipoise at 25° C.) and allowed to dwell in the solution for about 30 minutes under sufficient stirring to keep the drops formed upon addition into the sodium alginate solution separate. It is also significant to avoid overstirring, as this can cause high excess calcium release and alginate broth gelation. Most drops of the composition added were between about 3 millimeters in diameter and about 5 millimeters in diameter. After 30 minutes dwell time the formed microencapsulated beads were removed from the sodium alginate solution and rinsed three times with de-ionized water and cast to air-dry overnight at room-temperature. Stable microencapsulated heat delivery vehicles were formed.

EXAMPLE 6

In this Example, a microencapsulated heat delivery vehicle including calcium chloride as the encapsulating activator was produced.

Calcium chloride (about 20 micrometers in diameter) was introduced into mineral oil (available as Drakeol 7 LT NF from Penreco, Dickinson, Tex.) to form a 25% (by weight) calcium chloride composition that was mixed together thoroughly and had a resulting viscosity (25° C.) of about 300 centipoise. This composition was introduced dropwise from a separatory funnel into one half liter of an anionic water dispersed butadiene/acrylonitrile latex emulsion (100 grams of Eliochem Chemigum Latex 550 (commercially available from Eliochem, France) dissolved in 500 grams of de-ionized water) and allowed to dwell in the solution for about 10 minutes under sufficient stirring to keep the drops formed upon addition into the latex emulsion solution separate. Most drops of the composition added were between about 3 millimeters in diameter and about 5 millimeters in diameter. During a 30-minute dwell time, the microencapsulated beads were formed in a latex shell. These beads were removed from the latex emulsion and rinsed three times with de-ionized water and cast to air-dry overnight at room-temperature. Stable microencapsulated vehicles were formed.

EXAMPLE 7

In this Example a microencapsulated heat delivery vehicle including a fragrance oil was manufactured utilizing calcium chloride as the encapsulating activator.

A mixture (1 gram) of 25% (by weight) calcium chloride and 75% (by weight) mineral oil (available as Drakeol 7 LT NF from Penreco, Dickinson, Tex.) was added to 9 grams of Red Apple Fragrance Oil (commercially available from Intercontinental Fragrances, Houston, Tex.) and the resulting composition thoroughly mixed. The resulting composition was added dropwise from a separatory funnel to a 1% (by weight) sodium alginate in de-ionized water solution and allowed to dwell in the solution for about 20 minutes under sufficient stirring to keep the drops formed upon addition to the sodium alginate solution separate. It is also significant to avoid overstirring, as this can cause high excess calcium release and alginate broth gelation. After the 20 minute dwell time, the formed microencapsulated beads were removed from the sodium alginate solution and rinsed three times with de-ionized water and cast to air-dry overnight at room-temperature. Stable microencapsulated vehicles were formed.

EXAMPLE 8

In this Example, a microencapsulated heat delivery vehicle including a heating agent surrounded by a hydrophobic wax material was produced using a method of the present disclosure. This microencapsulated heat delivery vehicle was then analyzed to determine its ability to generate heat after being contacted with water as compared to a control sample, which was a microencapsulated heat delivery vehicle including a heating agent not surrounded by a hydrophobic wax material.

To produce the heating agent surrounded by a hydrophobic wax material for inclusion in the microencapsulated heat delivery vehicle, 100 grams of a hydrophobic wax material, available as Polywax 500 from Fischer-Tropsch Wax Products (Sugar Land, Tex.) was melted in a steel beaker at a temperature of about 110° C. and thoroughly mixed with 200 grams anhydrous magnesium chloride salt grains (available from Magnesium Interface Inc., Vancouver, B.C., Canada) having a particle size of about 100 micrometers. The agglomerated mass was allowed to cool to room temperature. A coffee grinder (commercially available as Mr. Coffee® Grinder from Hamilton Beach) was then used to break the mass into particles having a particle size of approximately 3 micrometers to 5 micrometers in diameter. A portion of these particles was introduced into water and found not to be soluble. This indicated the presence of a continuous wax coating surrounding the magnesium chloride.

Thirty grams of wax-coated magnesium chloride was added to a 30-gram suspension of 10% (by weight) calcium chloride/25% (by weight) magnesium chloride/65% (by weight) mineral oil to make a paste. The paste was added slowly to 2 liters of a 0.5% (by weight) aqueous sodium alginate solution. Using an overhead stirrer rotating at 700 revolutions per minute (rpm), the paste was broken down into emulsion forming beads having a diameter of about 2 millimeters. The beads were allowed to dwell for approximately 10 minutes in the high shear aqueous environment to form a crosslinked alginate shell. After 10 minutes, the beads were removed and rinsed with de-ionized water.

Three grams of the microencapsulated heat delivery vehicles were crushed in the presence of 7.0 grams water to determine the ability of the microencapsulated heat delivery vehicles to generate heat. The temperature of the water increased by approximately 10° C.

A control sample was then produced and compared to the microencapsulated heat delivery vehicles produced above. To produce the control sample, a 5% (by weight) calcium chloride/25% (by weight) magnesium chloride/70% (by weight) mineral oil paste was produced as described above with the exception that there was not any wax coated magnesium chloride. The resulting beads were then crushed in the presence of 7.0 grams water. With the control sample, a temperature increase of approximately 5° C. was detected.

The results show that the heat of hydration and heat of solution of the anhydrous magnesium chloride of the microencapsulated heat delivery vehicle including a heating agent surrounded by a hydrophobic wax material was maintained, while the magnesium chloride of the control sample was deactivated either during the high shear emulsion/encapsulation processes or in the rinsing and drying of the beads.

EXAMPLE 9

In this Example, a microencapsulated heat delivery vehicle including a heating agent surrounded by a hydrophobic wax material was produced. This microencapsulated heat delivery vehicle was analyzed to determine its ability to generate heat upon contact with water.

To produce the heating agent surrounded by a hydrophobic wax material, a blend of 95% (by weight) anhydrous magnesium chloride (available from Magnesium Interface Inc., Vancouver, B.C., Canada) and 5% (by weight) Polywax 500 (available from Fischer-Tropsch Wax Products, Sugar Land, Texas) was prepared by heating 500 grams of the blend to a temperature of 110° C. in a closed container. The blend was periodically stirred over a 2-hour period. While still hot, 4-millimeter ceramic milling media (Dynamic Ceramic, United Kingdom) were added to the container and rolled on a jar mill until the blend cooled to room temperature.

Fifty grams of the 95% (by weight) anhydrous magnesium chloride/5% (by weight) wax blend was added to 50 grams of a composition comprising 10% (by weight) calcium chloride and 90% (by weight) mineral oil. The resulting paste was added slowly into 2 liters of a 0.5% (by weight) aqueous sodium alginate solution. Using an overhead stirrer rotating at 650 rpm, the paste was broken down into emulsion forming beads having a diameter of between about 2 to 4 millimeters. The beads were allowed to dwell for approximately 10 minutes in the high shear aqueous environment to form a crosslinked alginate shell. After 10 minutes the beads were removed and rinsed with water.

Three grams of the microencapsulated heat delivery vehicle were crushed in the presence of 7.0 grams water to determine the ability of the microencapsulated heat delivery vehicle to generate heat. The temperature of the water increased by approximately 18° C. indicating that the wax coating protected the heating agent during the aqueous crosslinking process.

EXAMPLE 10

In this Example, spherical core materials containing a water soluble material were encapsulated with a moisture protective layer. These samples were then added to low conductivity water and the conductivity of this solution was monitored over time to compare the behavior of moisture protected and unprotected particles.

To produce the spherical core material including a moisture protective layer, 7.0 grams of approximately 2-millimeter sized beads containing 80 wt % wax (available as Dritex C from Dritex International Limited, Essex, United Kingdom) and 20 wt % sodium sulfate (a water soluble material) were formed in the following manner. Dritex C wax and sodium sulfate were melted to 100° C. in a pressure pot. A standard prilling process was used to form the beads wherein the melted composition was sprayed out of a single nozzle fluid and the 2 millimeter beads were collected. To form the moisture protective layer, 7 grams of these beads were introduced into a glass beaker. Using a dropper, 0.295 grams of Pluracol GP-430, which is a polyol, available from BASF Corporation (Wyandotte, Mich.), was added to the glass beaker. The mixture was hand stirred using a spatula for about 5 minutes to fully coat the core material. After stirring the mixture, 0.314 grams Lupranate M20-S, which is a polyether polyol available from BASF Corporation (Wyandotte, Mich.), was added to the mixture using a dropper. The mixture, including the Lupranate, was hand stirred using a spatula for about 15 minutes. The mixture was then allowed to oven cure at 60° C. for 15 minutes to form the moisture protective layer on the spherical core material.

2.0 grams of core material particles were added to 120 grams of deionized water in a 150 milliliter beaker. The conductivity of the deionized water was then measured as a function of time using an Orion model 135 Waterproof Conductivity/TDS/Salinity/Temperature Meter (Fischer Scientific). The conductivity of the control sample (spherical core material without any moisture protective coating was also analyzed. The results are shown in FIG. 5.

Figure 5:
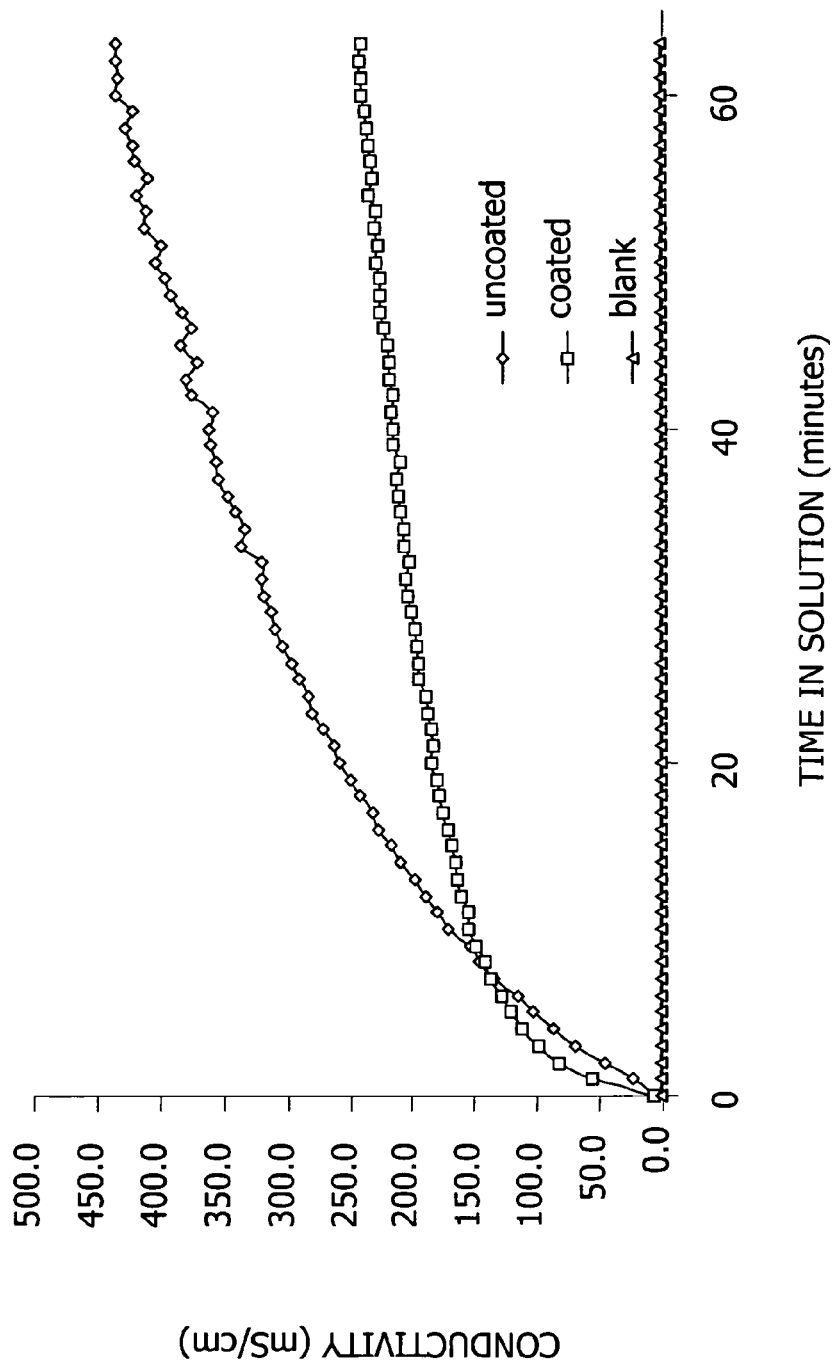
FIG. 5 is a graph illustrating the conductivity of a solution including a microencapsulated delivery vehicle having a moisture protective layer made in accordance with an experiment described herein.

As shown in FIG. 5, the core material particles with a protective layer have a slower rate of conductivity increase over non protected materials. It is advantageous to have a low release of water sensitive materials to insure moisture protection of the core material.

EXAMPLE 11

In this Example, anhydrous calcium chloride particles were treated to impart a moisture protective layer thereon. The ability of the calcium chloride particles including the moisture protective layer to generate heat after contact with water was analyzed and compared to a control sample, which included calcium chloride particles without a moisture protective layer.

To impart the moisture protective layer onto the calcium chloride particles, 250 grams anhydrous calcium chloride with a particle size of about 2 millimeters (available from The Dow Chemical Company, Midland, Mich.) were added to a V-blender, rotating at a speed of 62 revolutions per minute (rpm) and maintained at a temperature of 60° C. Rotation of the V-blender was stopped and a dropper was used to add 2.50 grams of Pluracol GP 430, a polyol available from BASF Corporation (Wyandotte, Mich.) to form a mixture of anhydrous calcium chloride and Pluracol GP 430. The mixture was blended in the V-blender for approximately one minute. The V-blender was again stopped and 2.50 grams Lupranate M20-S, a polyether polyol available from BASF Corporation (Wyandotte, Mich.), was added. The mixture was blended for about 10 minutes. After blending the mixture, about 2.50 grams of refined yellow #1 Carnauba wax, available from Sigma-Aldrich Co. (St. Louis, Mo.) was added and the blender again started. The temperature of the mixture in the blender was increased to 95° C. The blending was continued for about 15 minutes at 95° C. The blending was stopped and the mixture was allowed to cool to ambient temperature.

A second addition of Pluracol GP 430, Lupranate M20-S, and yellow #1 Carnauba wax was added to the blended mixture in the same manner as described above. Additionally, a third addition of Pluracol GP 430 and Lupranate was added and blended as described above. After blending the mixture, the mixture was allowed to oven cure at 60° C. for 15 minutes. The mixture was allowed to cool and sealed in a jar. After 24 hours, the yellow #1 Carnauba wax was added to the cooled mixture in the manner described above and the mixture was again allowed to cool to form the microencapsulated heat delivery vehicle including a moisture protective layer.

Four samples of the calcium chloride particles including a moisture protective layer were then analyzed for their ability to generate heat after exposure to water. A control sample (calcium chloride) was also tested for heat generating capabilities and compared to the four samples of calcium chloride having a moisture protective layer.

To analyze the samples for heat generation, 0.80 grams of each sample of calcium chloride including a moisture protective layer was added to four separate vials each containing 7.0 grams of de-ionized water and 0.73 grams of the control sample was added to a fifth vial containing 7.0 grams of de-ionized water. Using a J type thermocouple (commercially available from Omega Engineering, Inc., Stamford, Conn.) and a data logger, the temperature of the samples was measured over a period of 180 seconds. The four vials containing the samples of microencapsulated heat delivery vehicle including a moisture protective layer were allowed to remain in the de-ionized water for 0.5 hours, 1.0 hour, 1.5 hours, and 2.0 hours, respectively, at which time the samples were activated by crushing the samples by hand using a metal rod. The temperature of the water in the four vials was measured for a period of 180 seconds after crushing the samples. The results are shown in FIG. 6.

Figure 6:
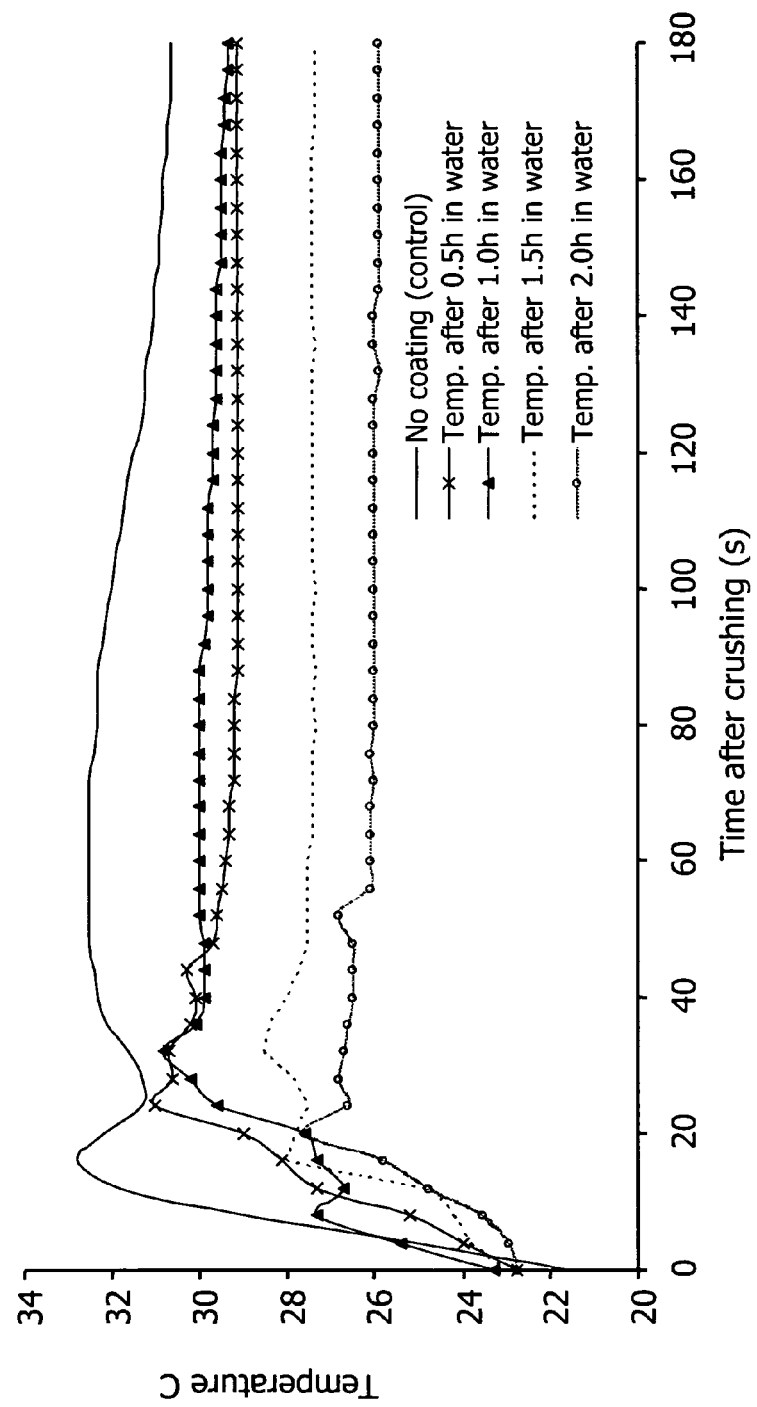
FIG. 6 is a graph illustrating the ability of various samples of microencapsulated heat delivery vehicles including moisture protective layers to generate heat as tested in accordance with an experiment described herein.

As shown in FIG. 6, the samples of microencapsulated heat delivery vehicles including a moisture protective layer continued to produce heat after soaking in de-ionized water after two hours. The control sample having no protective layer, however, produced heat immediately upon being introduced into water but only for a short period of time.

EXAMPLE 12

In this Example, microencapsulated heat delivery vehicles including a moisture protective layer comprising various amounts of a mixture of Saran F-310 and polymethylmethacrylate were produced. The samples were then evaluated for water barrier properties by soaking the samples in a wetting solution at a temperature of approximately 50° C., and then submitting the samples to a heat test.

Three levels of moisture protective layer on the microencapsulated heat delivery vehicles were evaluated: (1) 17% (by weight microencapsulated heat delivery vehicle); (2) 23% (by weight microencapsulated heat delivery vehicle; and (3) 33% (by weight microencapsulated heat delivery vehicle). To produce the Saran F-310/polymethylmethacrylate solution for application to the microencapsulated heat delivery vehicles to form the moisture protective layer, 80 grams Saran F-310, available from Dow Chemical Company (Midland, Mich.) was dissolved in a 320-gram solution of 70% (by weight) methyl ethyl ketone (MEK) and 30% (by weight) toluene, and 20 grams polymethylmethacrylate was dissolved in 180 grams acetone. The Saran F-310 and polymethylmethacrylate solutions were then blended together to produce a solution comprising 20% (by weight) solids wherein 90% (by weight solids) was Saran F-310 and 10% (by weight solids) was polymethylmethacrylate (treatment solution).

Once the treatment solution was produced, the microencapsulated heat delivery vehicles including the desired amounts of moisture protective layer were produced. First, in order to provide a continuous layer of shell material at the "base" or bottom of the microencapsulated heat delivery vehicles, a glass syringe was used to apply 1.5 grams of the treatment solution to a sheet of Saran film, which had been stretched over a flat surface (17"×22" metal sheet). The treatment solution was allowed to dry until it reached the tacky stage. The Saran film surface was marked with circles of approximately three inches in diameter in order to be used as a guide and to facilitate even coating of the shell material. For the 17% (by weight) coating, three grams of microencapsulated heat delivery vehicles as produced in Example 8 were then placed in an aluminum weigh pan and blended with 1.5 grams of the treatment solution until the beads were well coated. Using a scoopula, the beads were stirred in the solution until well coated. The coated beads were then poured with the remaining treatment solution onto the base coat layer on the Saran film and allowed to dry completely.

The samples including 23% (by weight) moisture protective layer were produced using the method described above with the exception of using 2.25 grams of the treatment solution instead of 1.5 grams of treatment solution.

To produce the samples including 33% (by weight) shell material, two base coats were produced using the method described above, each comprising 1.9 grams of treatment solution. The first base coat was allowed to dry prior to applying the second base coat. Three grams of the alginate beads were blended with 1.9 grams of treatment solution in the aluminum weigh pan. The coated microencapsulated heat delivery vehicles were then poured onto the base coat layers and allowed to dry to the tacky stage. An additional 1.9 grams of treatment solution was applied over the coated alginate beads and allowed to completely dry.

Figure 7:
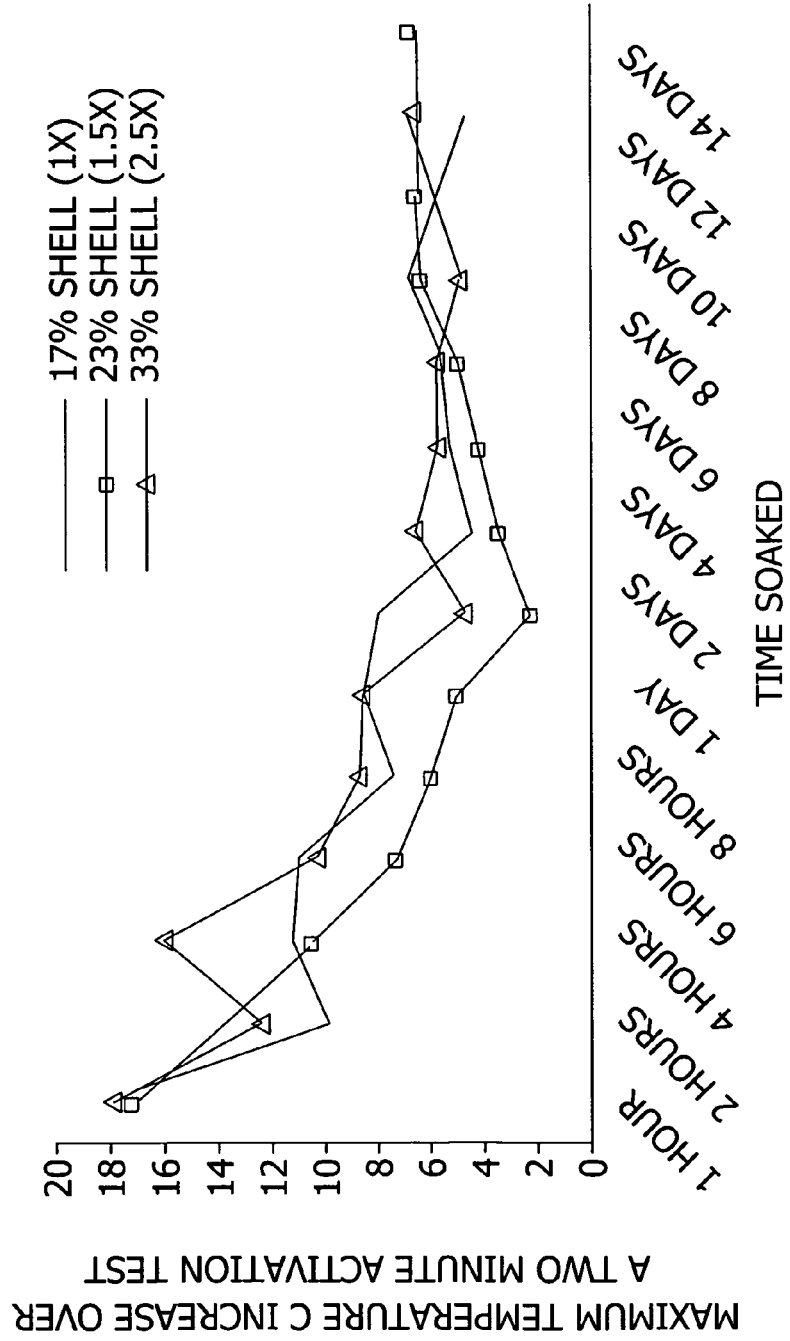
FIG. 7 is a graph illustrating the ability of microencapsulated heat delivery vehicles including various coating levels of moisture protective layers to generate heat as tested in accordance with an experiment described herein.

Sixteen samples of each coating amount were then analyzed for their ability to generate heat after being immersed in the wetting solution and held at a temperature of 50° C. for various lengths of time ranging from 0 to 14 days. To analyze the samples, 3.0 grams of each sample are added to an empty balloon. A wetting solution (7 grams) comprising: 98% (by weight) water, 0.6% (by weight) potassium laureth phosphate, 0.3% (by weight) glycerin, 0.3% (by weight) polysorbate 20, 0.2% (by weight) tetrasodium EDTA, 0.2% (by weight) DMDM hydrantoin, 0.15% (by weight) methylparaben, 0.07% (by weight) malic acid, 0.001% (by weight) aloe barbadensis, and 0.001% (by weight) tocopheryl acetate. A thermocouple is then introduced into the balloon to monitor the temperature. The sample beads were then activated by hand crushing the beads and the temperature increase is measured. The results for each coating amount were averaged and shown in FIG. 7.

EXAMPLE 13

In this Example, samples of microencapsulated heat delivery vehicles including non-polymeric moisture protective layers were produced using electroless silver plating on microencapsulated heat delivery vehicles. The samples were then analyzed for their ability to generate heat.

To produce the electroless silver coating solutions, a sensitizer solution, reducer solution, and silver coating solution were produced. The sensitizer solution was produced by adding 4.8 grams of 22° Baume HCl (Fischer Scientific Technical Grade) to 946 milliliters of de-ionized water. 10 grams of 98% (by weight) stannous chloride, available from Sigma-Aldrich Co. (St. Louis, Mo.) was then added to the solution. To produce the reducer solution, 170 grams dextrose was dissolved in 946 milliliters de-ionized water. To produce the silver coating solution, 10 grams potassium hydroxide was dissolved in 3 liters of de-ionized water. Once dissolved, 50 milliliters of ammonium hydroxide was added to the solution and then finally, 25 grams of silver nitrate was added during vigorous agitation using a 3 blade-2 stirrer mixer, mixing at about 2000 revolutions per minute (rpm). The agitation was continued until the brown precipitate was re-dissolved. De-ionized water was added to the mixture in an amount to produce one gallon of silver coating solution.

Prior to coating the microencapsulated heat delivery vehicles as described below, the vehicles were analyzed to determine their ability to generate heat as measured in Example 12 above.

Fifteen grams of microencapsulated heat delivery vehicles as made in Example 8 were placed into a quart jar, which was then filled three-quarters full with sensitizer solution. The jar was then agitated by turning the jar end-to-end for about 10 minutes. The beads were then agitated by stirring by hand for about 10 minutes and rinsed thoroughly with water. The beads were then transferred to a quart jar filled three-quarters full with silver coating solution. To the quart jar, 24 milliliters of reducer solution was added and the jar was capped and turned end-to-end for approximately 5 minutes. The solution was then poured through a screen to strain the beads and the beads were washed 3 to 5 times thoroughly with de-ionized water. This electroless silver plating process was repeated three more times to produce a four-layer silver coating on the alginate beads.

Three grams of coated microencapsulated heat delivery vehicles were analyzed for their ability to generate heat after being immersed in the wetting solution of Example 12 and held at 50° C. The beads were tested at intervals of 4 hours, 8 hours, 24 hours, and 48 hours. The results are shown in FIG. 8.

Figure 8:
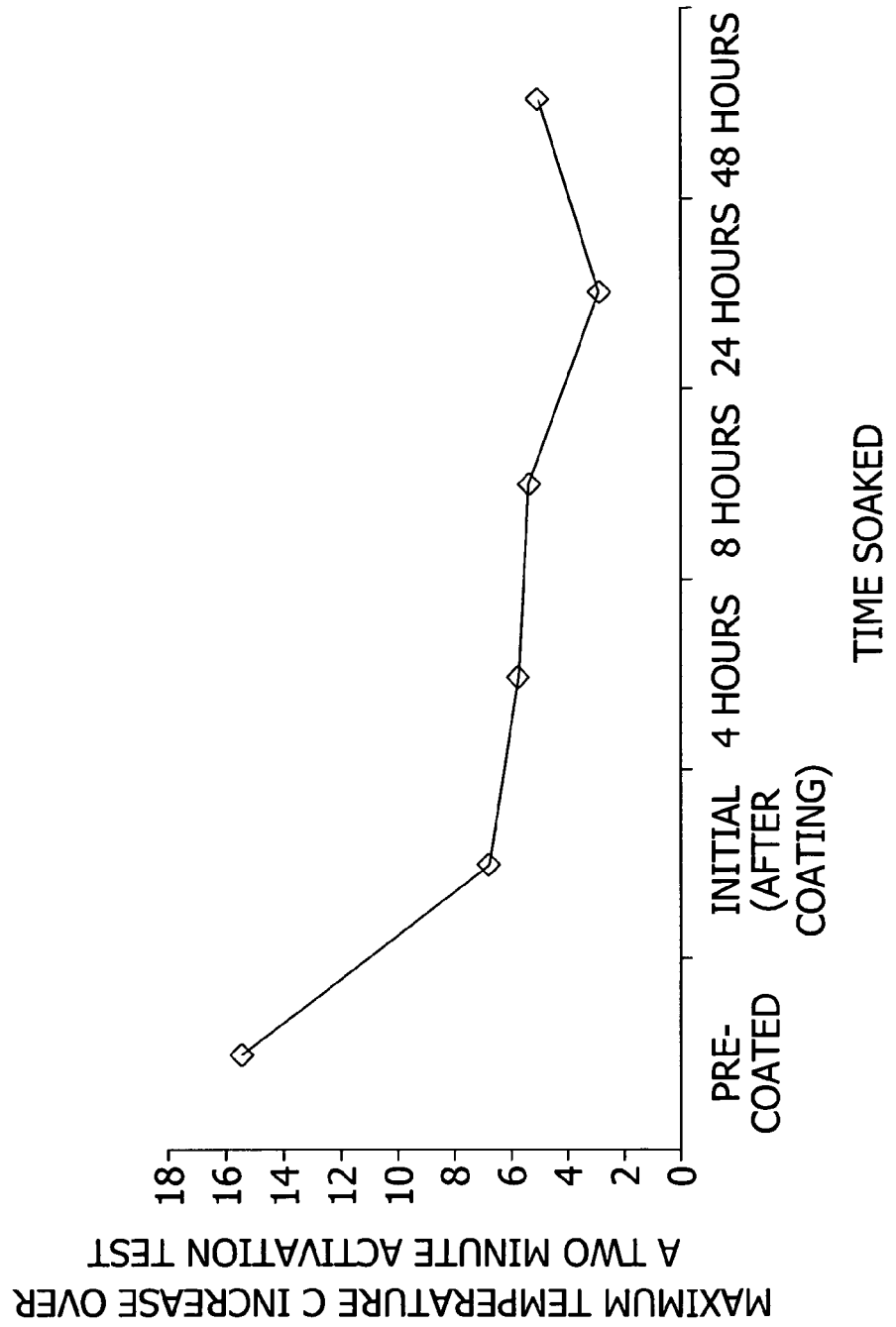
FIG. 8 is a graph illustrating the ability of microencapsulated heat delivery vehicles including moisture protective layers to generate heat after being flooded over various intervals of time with a wetting solution as tested in accordance with an experiment described herein.

As shown in FIG. 8, while the electroless silver plating process does produce a microencapsulated heat delivery vehicle including a moisture protective layer, the plating process greatly diminishes the heat generating ability of the alginate beads.

EXAMPLE 14

In this Example, samples of pan coated alginate microencapsulated heat delivery vehicles having three different coating thicknesses were produced and analyzed for particle strength. Specifically, the samples were analyzed to determine the rupture point or the point at which the rupture force is strong enough to rupture the particles.

Four samples of P7-A pan coated alginate microencapsulated heat delivery vehicle were produced by using the method of Example 12. Two samples of P7-B pan coated alginate microencapsulated heat delivery vehicle were produced using the same method as used to produce the P7-A samples with the exception that 1.5 times the amount of coating was used to coat the microencapsulated heat delivery vehicle. Three samples of P7-C pan coated alginate microencapsulated heat delivery vehicle were produced using the same method as used to produce the P7-A samples with the exception that 2.5 times the amount of coating was used to coat the microencapsulated heat delivery vehicle.

To test particle strength, a TA Texture Analyzer (Software Version 1.22) (available from Texture Technologies Corporation, Scarsdale, N.Y.) was used. Specifically, a single particle of each sample was independently placed on a polycarbonate plate and force measurements were made using a one-quarter inch to one inch diameter flat probe, moving at a rate of about 0.25 millimeter/second to about 5.0 millimeters/second. As the force load was applied by the probe, the particle deformed until it cracked or collapsed. Generally, the deformation of the particle continues until the applied force increases exponentially, indicating that the shell of the particle has been ruptured. As used herein, the "rupture point" is defined as the height of the first peak on the graphs in FIGS. 9-11, indicating a decrease in resistance caused by the outer shell breaking. The results of the measurements are shown in Table 3 and FIGS. 9-11.

TABLE 3

| Pan Coated Alginate Microencapsulated Heat Delivery Vehicle Sample | Sample No. | Force (grams) required to rupture sample particle |
|---|---|---|
| P7-A | 1 | 284 |
| | 2 | 283 |
| | 3 | 71 |
| | 4 | 264 |
| P7-B | 1 | 228 |
| | 2 | 151 |
| P7-C | 1 | 526 |
| | 2 | 297 |
| | 3 | 323 |

Figure 9:
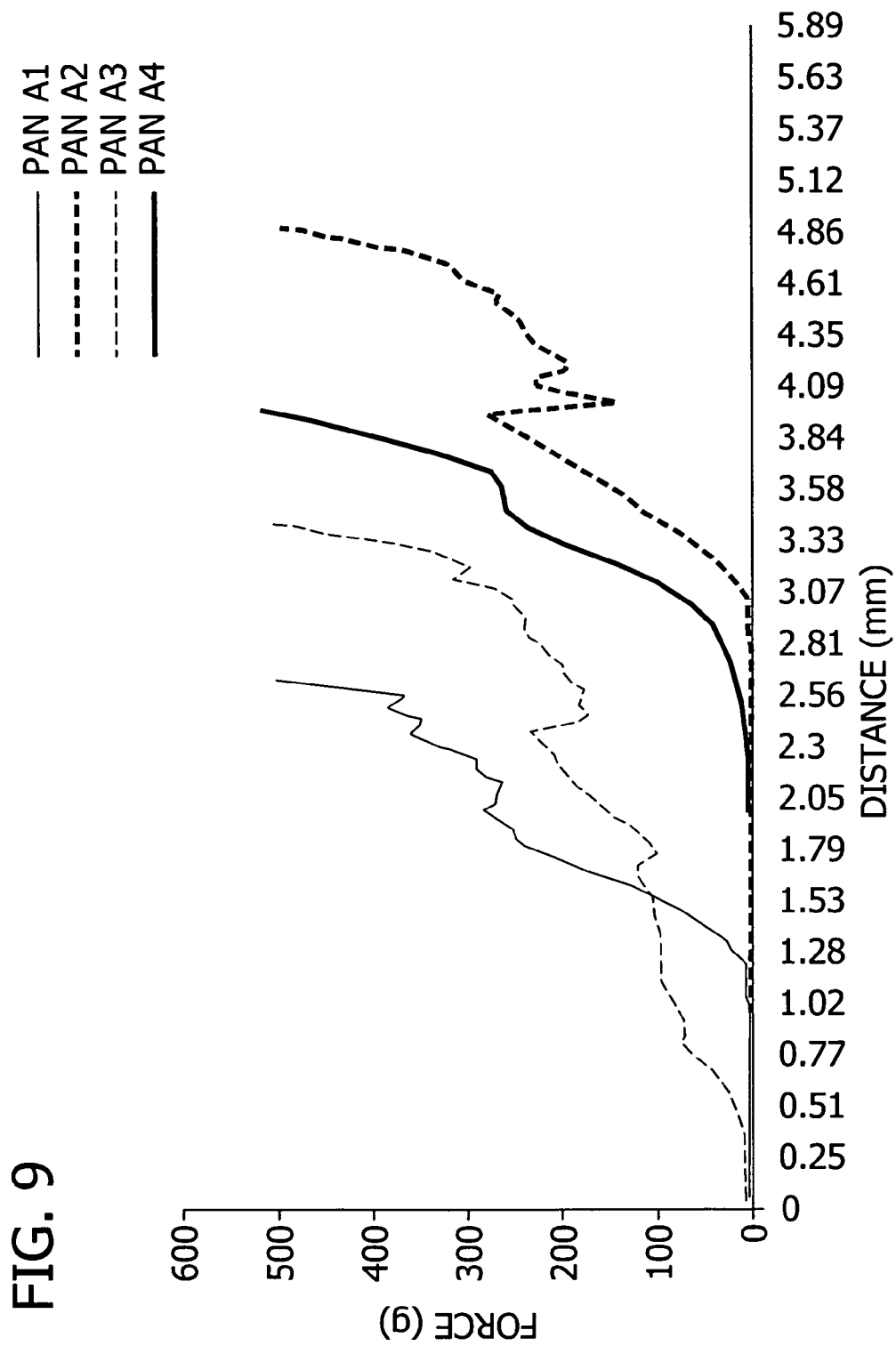
FIGS. 9-11 are graphs illustrating the rupture force required to rupture various microencapsulated heat delivery vehicles as tested in accordance with an experiment described herein.
Figure 10:
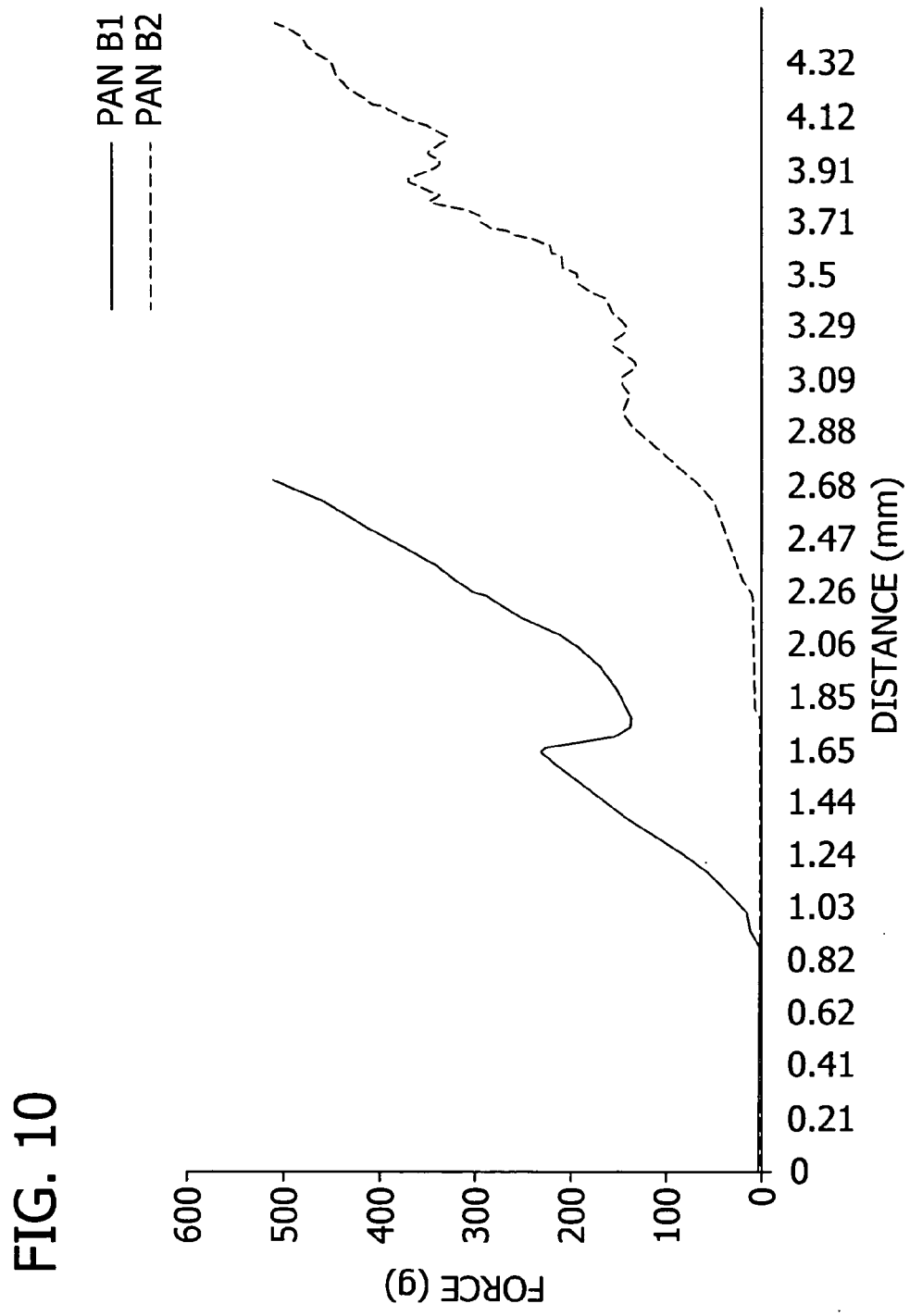
Figure 11:
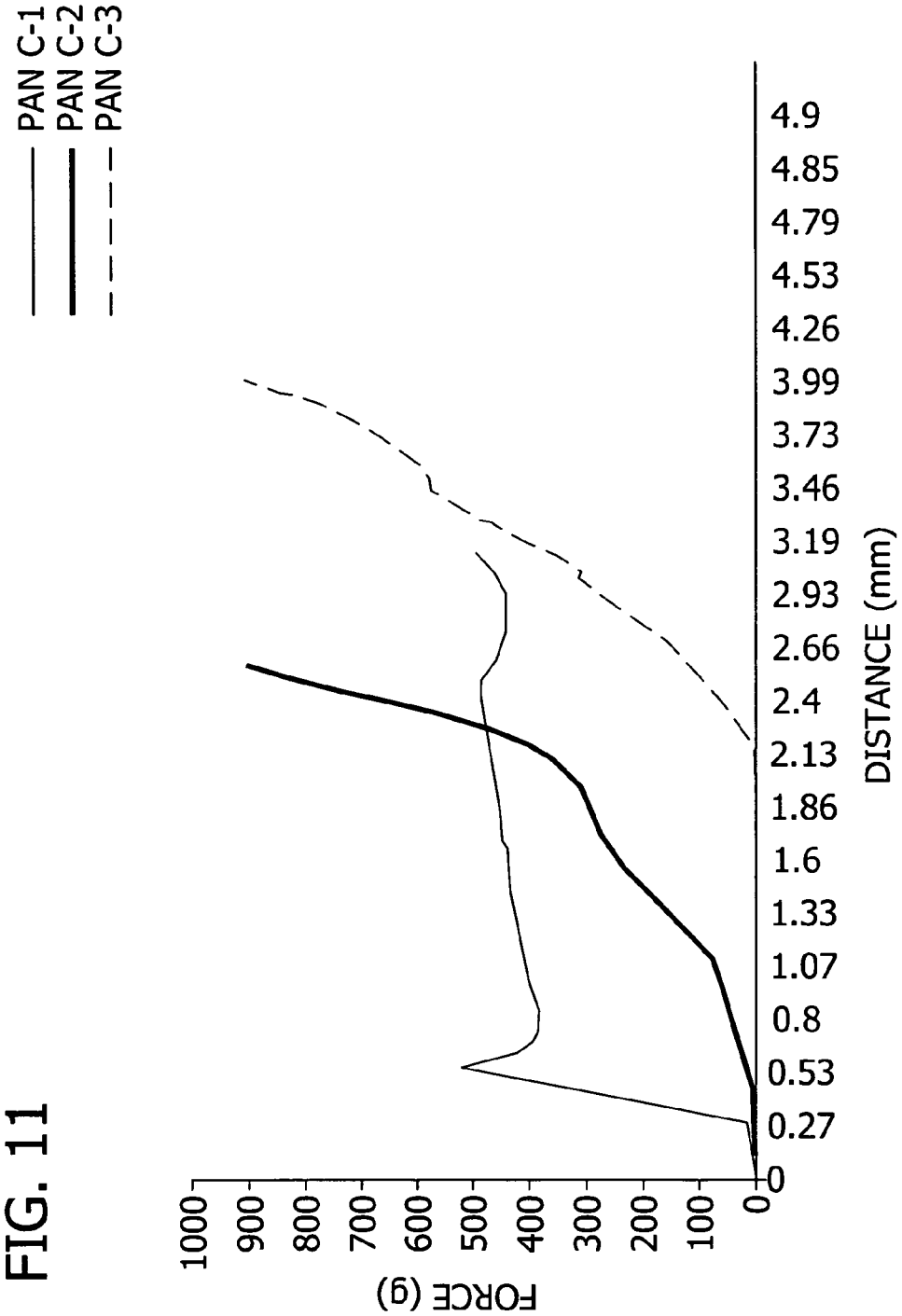

As shown in Table 3 and FIGS. 9-11, more force was required to crush samples of P7-C than samples of P7-A or P7-B. Additionally, as shown in FIGS. 9-11, samples of P7-C, did not appear to deform as samples of P7-A or P7-B, as indicated by the steeper slope of the force curve.

EXAMPLE 15

In this Examples, samples of alginate coated micorencapsulated heat delivery vehicle were produced and analyzed for particle strength. Specifically, the samples were analyzed to determine the rupture point or the point at which the rupture force is strong enough to rupture the particles.

Six samples of P7-F alginate coated microencapsulated heat delivery vehicle were produced using the method of Example 12. Seven samples of P7-G alginate coated microencapsulated heat delivery vehicle were produced using the same method as for making the samples of P7-F with the exception that the samples of P7-G were soaked in the wetting solution of Example 12 for 48 hours at a temperature of 50° C. Four samples of P7-J alginate coated microencapsulated heat delivery vehicle were produced using the method of Example 8. The P7-J samples were then coated with Saran F310 using the method of Example 12 above.

To test particle strength, a TA Texture Analyzer (available from Texture Technologies, Scarsdale, N.Y.) was used as describe above. The results of the measurements are shown in Table 4 and FIGS. 12-14.

TABLE 4

| Pan Coated Alginate Microencapsulated Heat Delivery Vehicle Sample | Sample No. | Force (grams) required to rupture sample particle |
|---|---|---|
| P7-F | 1 | 212 |
| | 2 | 64 |
| | 3 | 190 |
| | 4 | 113 |
| | 5 | 44 |
| | 6 | 145 |
| P7-G | 1 | 163 |
| | 2 | 49 |
| | 3 | 76 |
| | 4 | 260 |
| | 5 | 44 |
| | 6 | 32 |
| P7-J | 1 | 88 |
| | 2 | 233 |
| | 3 | 84 |
| | 4 | 49 |

Figure 12:
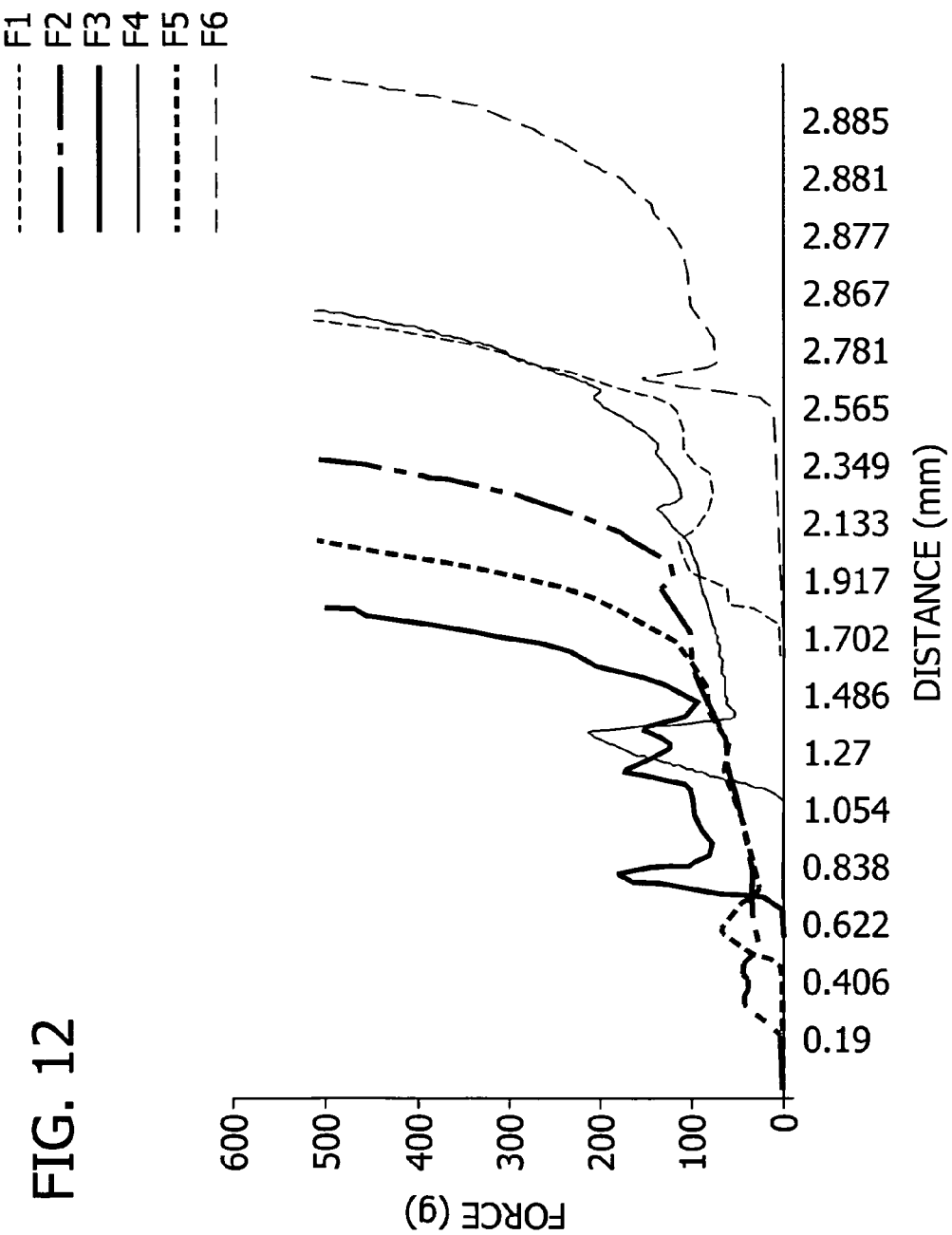
FIGS. 12-14 are graphs illustrating the rupture force required to rupture various microencapsulated heat delivery vehicles as tested in accordance with an experiment described herein.
Figure 13:
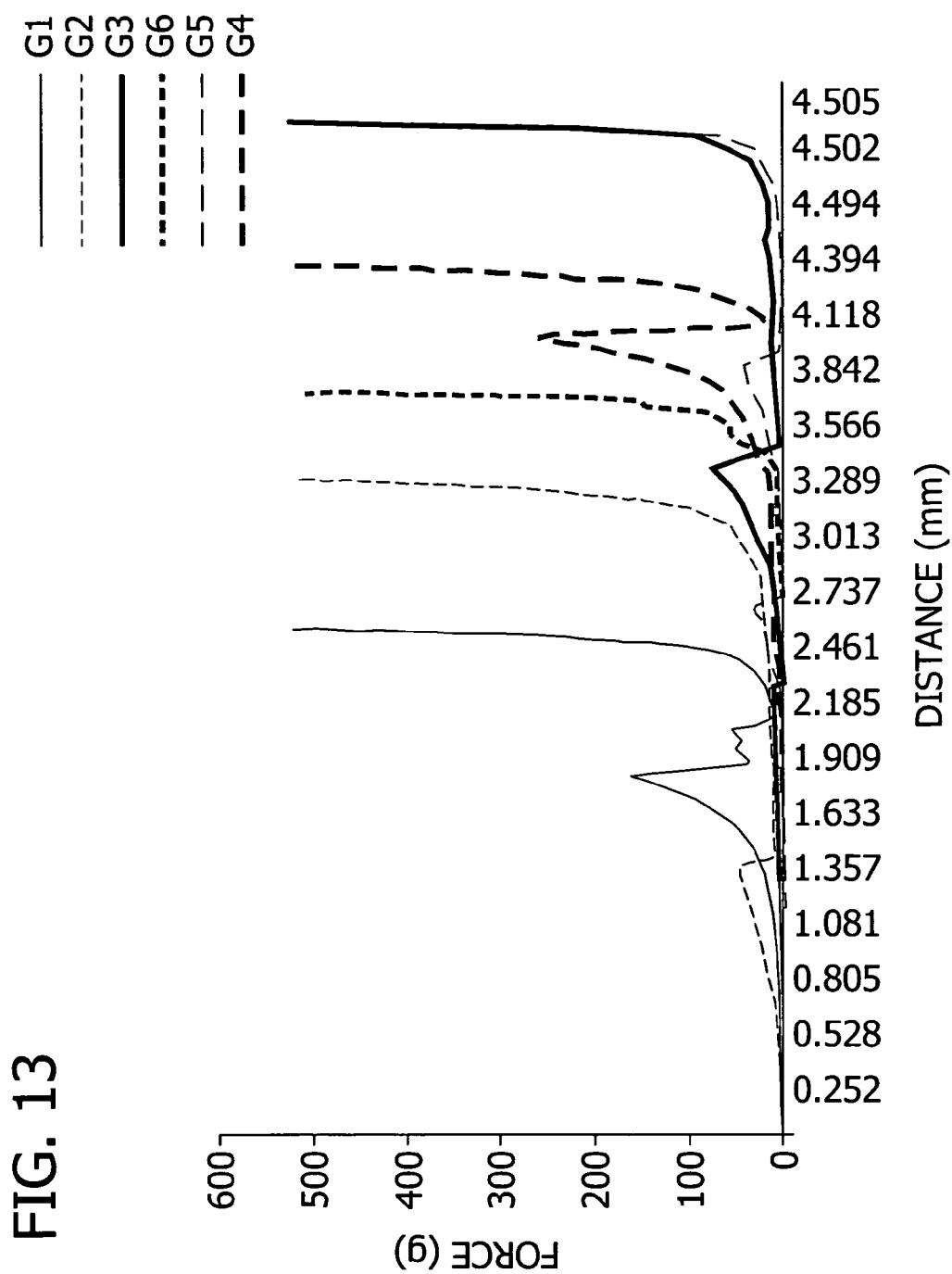
Figure 14:
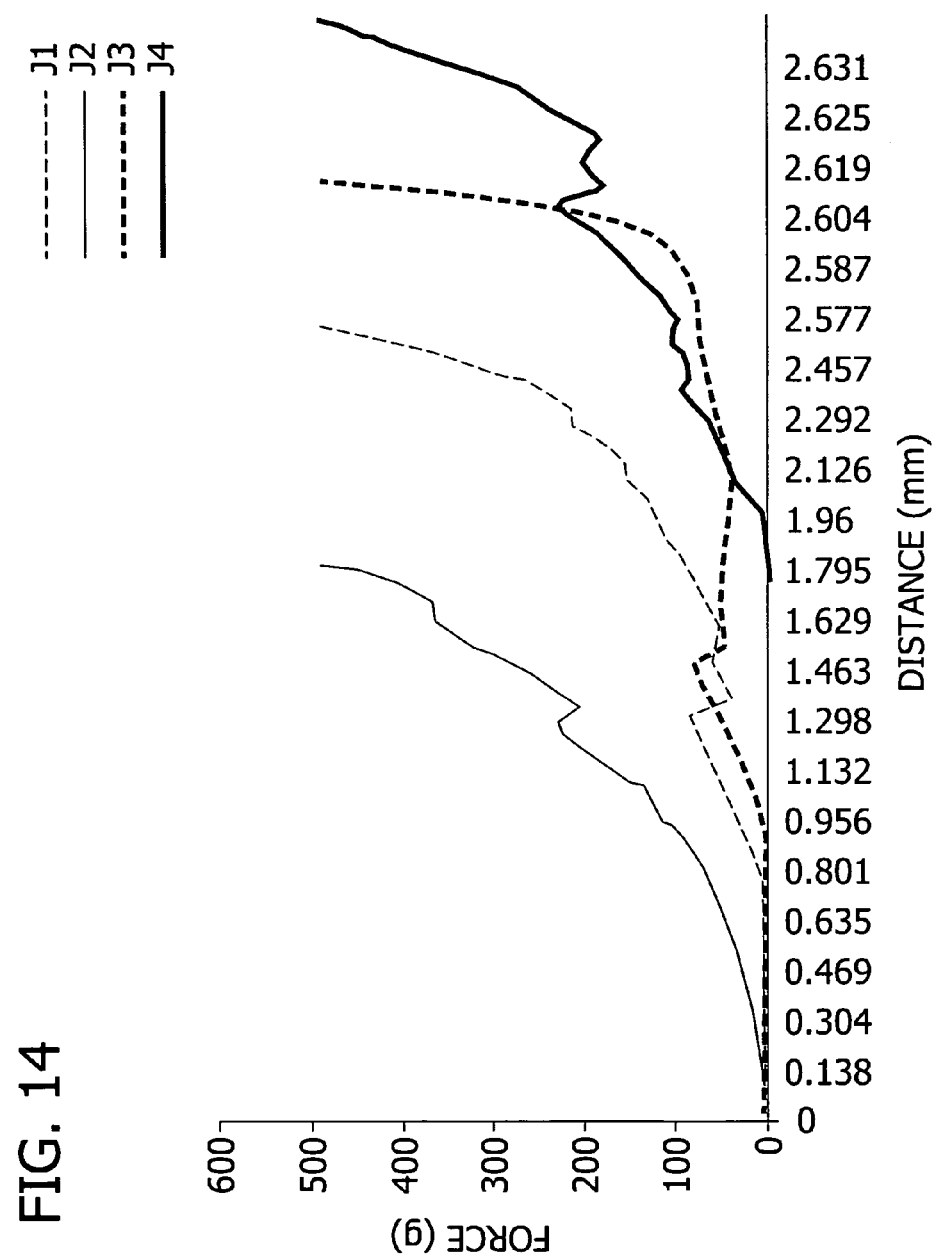

As shown in Table 4 and FIGS. 12-14, more force was required to crush samples of P7-F than samples of P7-G or P7-J. Additionally, as shown in FIG. 13, after the outer shell of the P7-G samples ruptured, the compression force drops to almost zero, which suggests that the P7-G particles are hollow and offer no resistance after the outer shell is ruptured. These results are compared to the P7-F samples, which were not soaked in wetting solution. Once the outer shell ruptured, the compression force drops on the P7-F samples, but plateaus above zero. This resistance after the outer shell of the P7-F samples rupture is attributed to the resistance of the anhydrous magnesium chloride oil mixture being forced out of the shell.

EXAMPLE 16

In this Example, samples of alginate coated microencapsulated heat delivery vehicle comprising either silica or chitosan were produced and analyzed for particle strength. Specifically, the samples were analyzed to determine the rupture point or the point at which the rupture force is strong enough to rupture the particles.

Three samples of P6-C alginate coated microencapsulated heat delivery vehicle were produced using the method of Example 12. Five samples of P6-D alginate coated microencapsulated heat delivery vehicle were produced using the same method as for making the samples of P6-C with the exception that the samples of P6-D were additionally coated with a 0.5% (by weight) aqueous solution of chitosan prior to drying the beads to provide improved particle strength. The samples of P6-D were then rinsed and allowed to air-dry. Three samples of P6-E alginate coated microencapsulated heat delivery vehicle were produced using the same method as for making the samples of P6-C with the exception that the samples of P6-E were additionally coated with fumed silica after drying the beads to provide improved particle strength. The samples of P6-E were coated with 5% (by weight) Cabot M5 silica and allowed to air-dry and then jar rolled for approximately 2 hours.

To test particle strength, a TA Texture Analyzer (available from Texture Technologies, Scarsdale, N.Y.) was used as described above. The results of the measurements are shown in Table 5 and FIGS. 15-17.

TABLE 5

| Pan Coated Alginate Microencapsulated Heat Delivery Vehicle Sample | Sample No. | Force (grams) required to rupture sample particle |
|---|---|---|
| P6-C | 1 | 38 |
|  | 2 | 31 |
|  | 3 | 56 |
| P6-D | 1 | 164 |
|  | 2 | 84 |
|  | 3 | 123 |
|  | 4 | 74 |
|  | 5 | 59 |
| P6-E | 1 | 71 |
|  | 2 | 54 |
|  | 3 | 72 |

Figure 15:
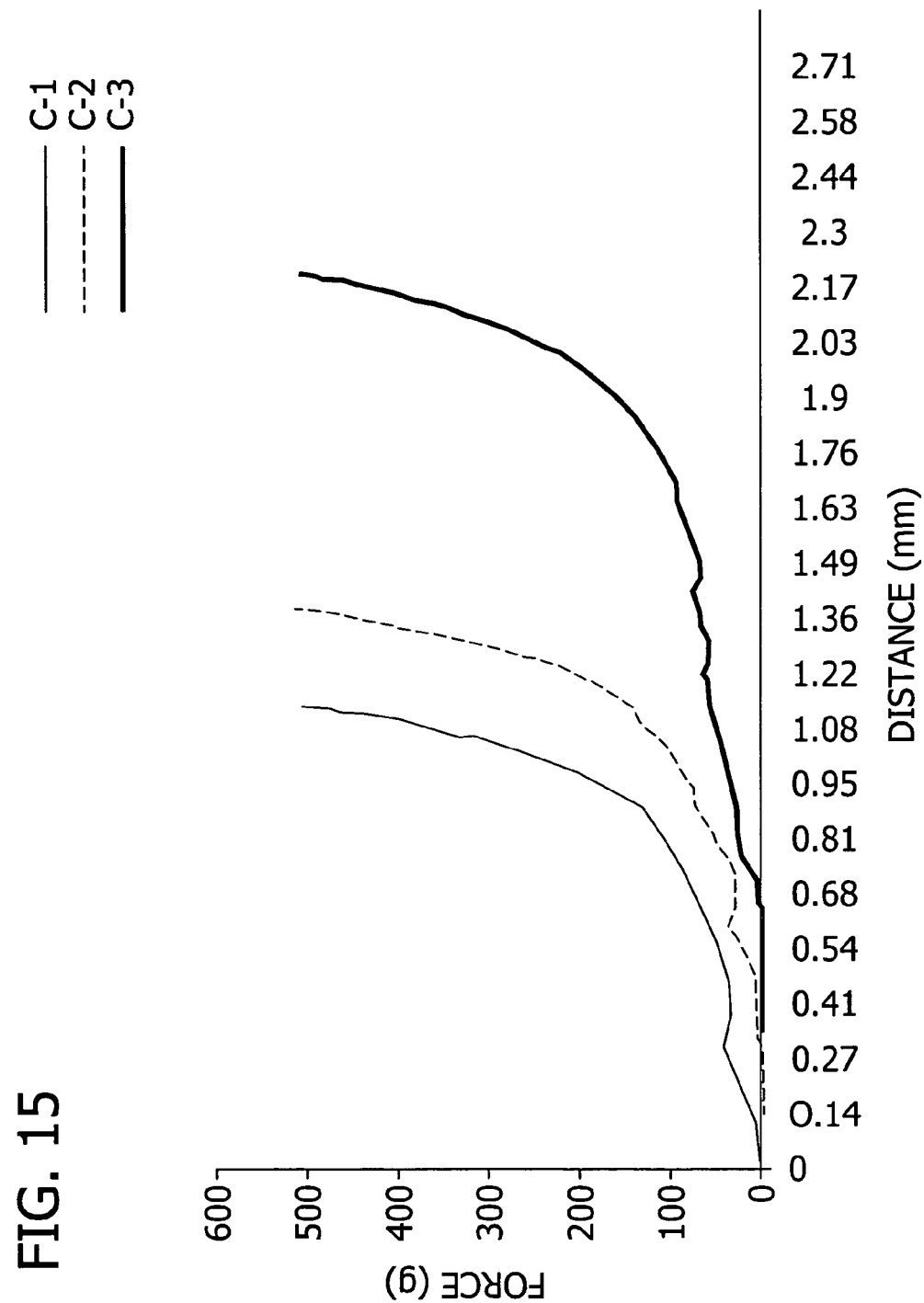
FIGS. 15-17 are graphs illustrating the rupture force required to rupture various microencapsulated heat delivery vehicles as tested in accordance with an experiment described herein.
Figure 16:
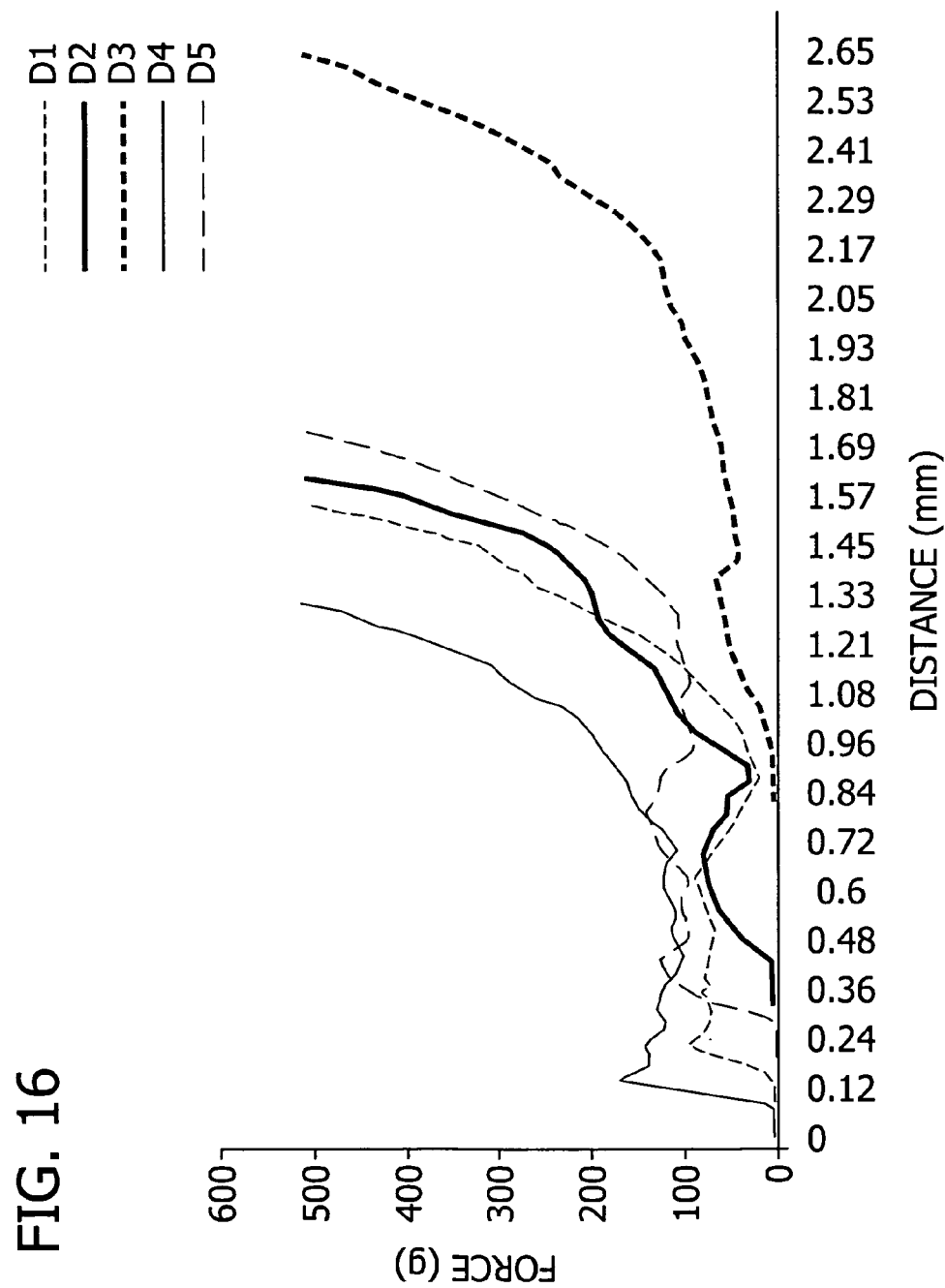
Figure 17:
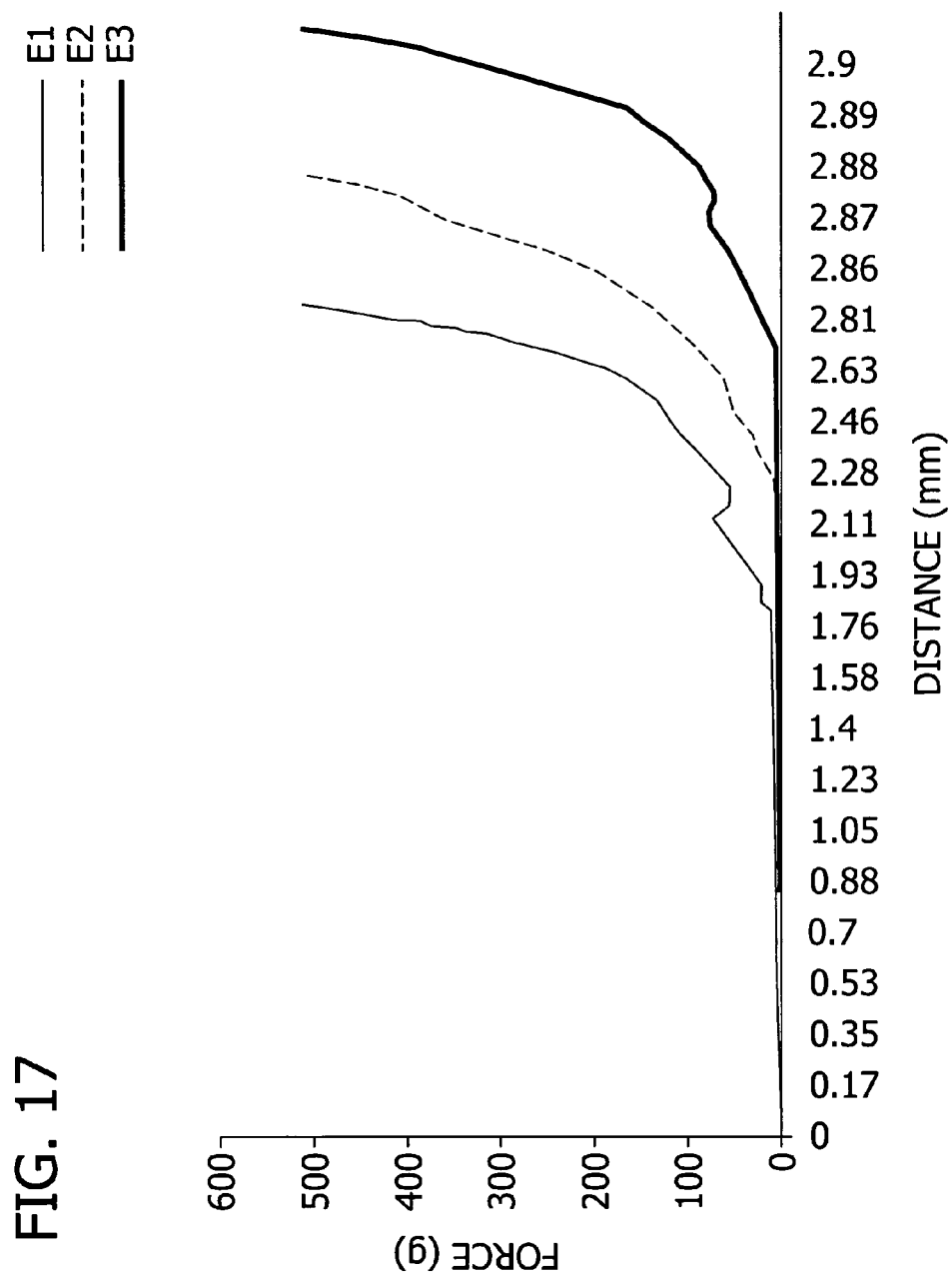
Figure 18:
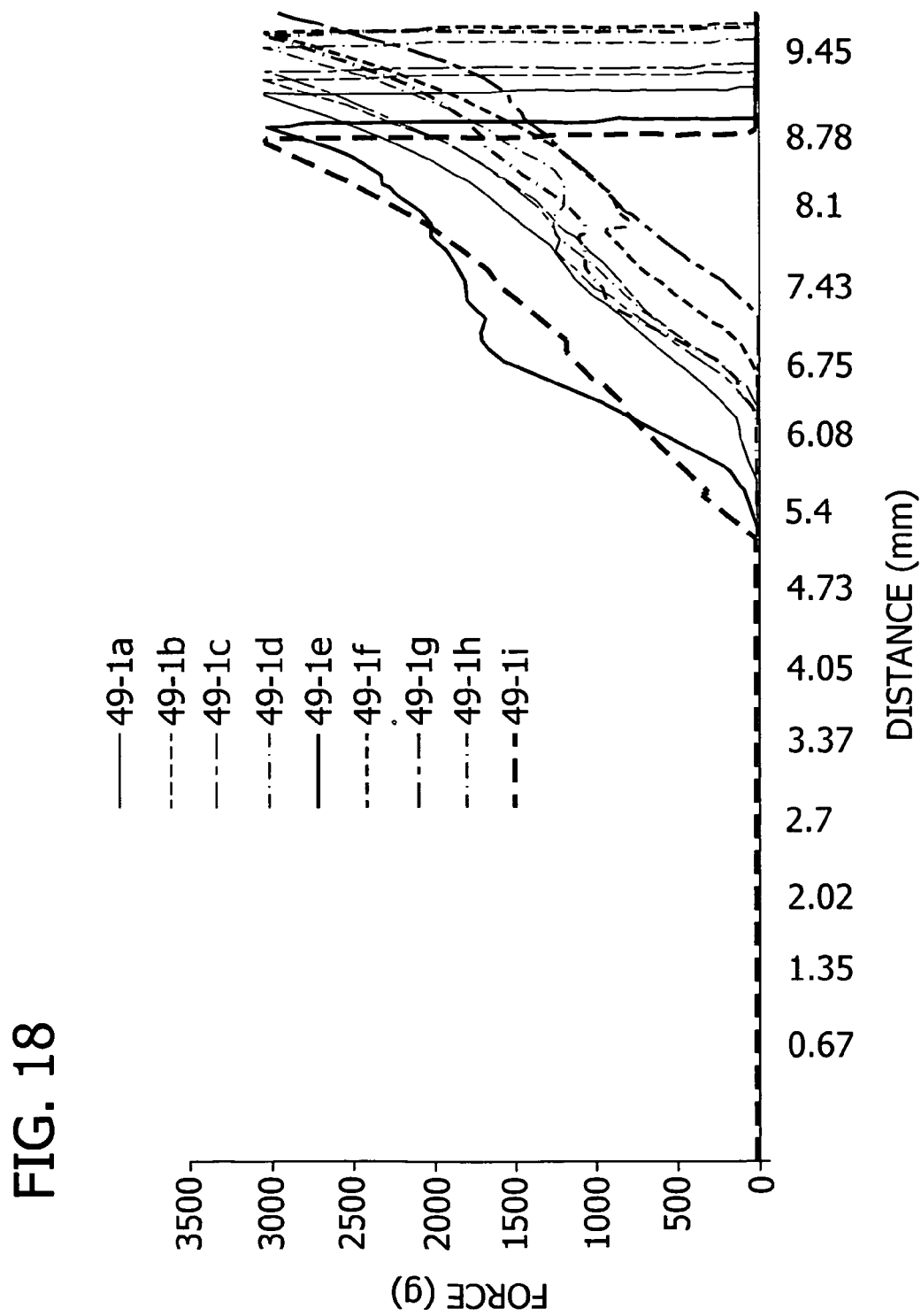
FIGS. 18-24 are graphs illustrating the rupture force required to rupture various microencapsulated heat delivery vehicles as tested in accordance with an experiment described herein.
Figure 19:
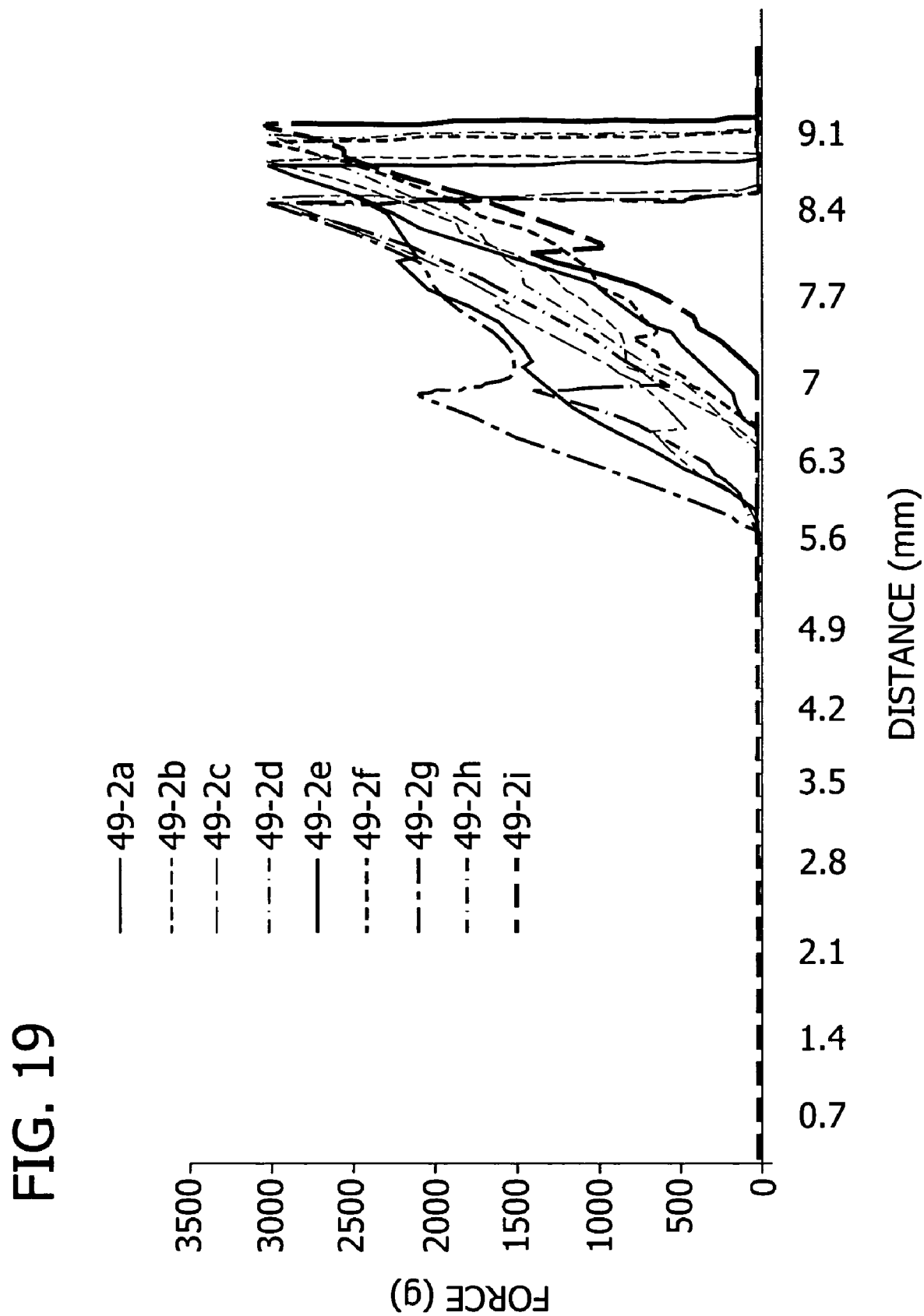
Figure 20:
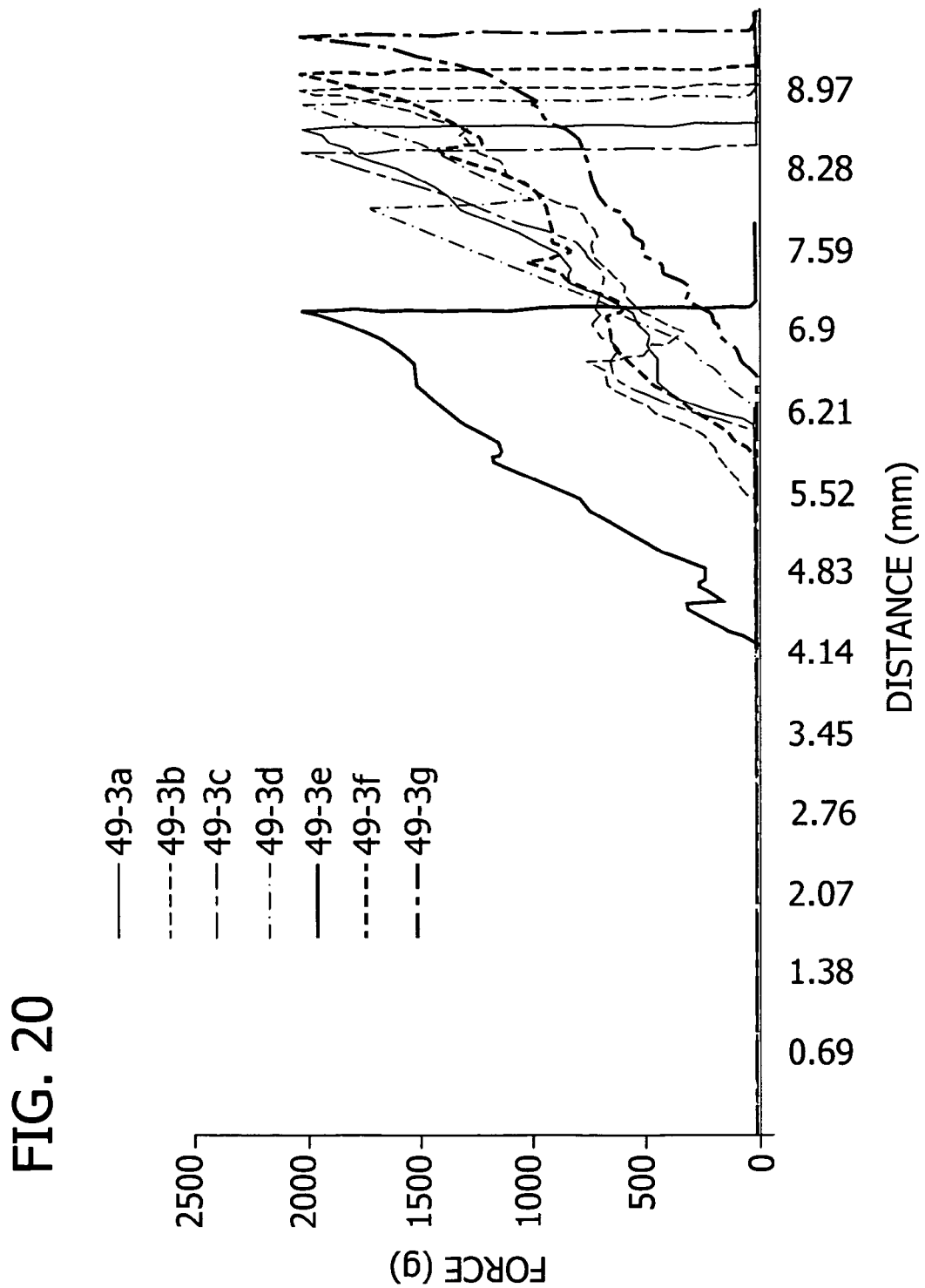
Figure 21:
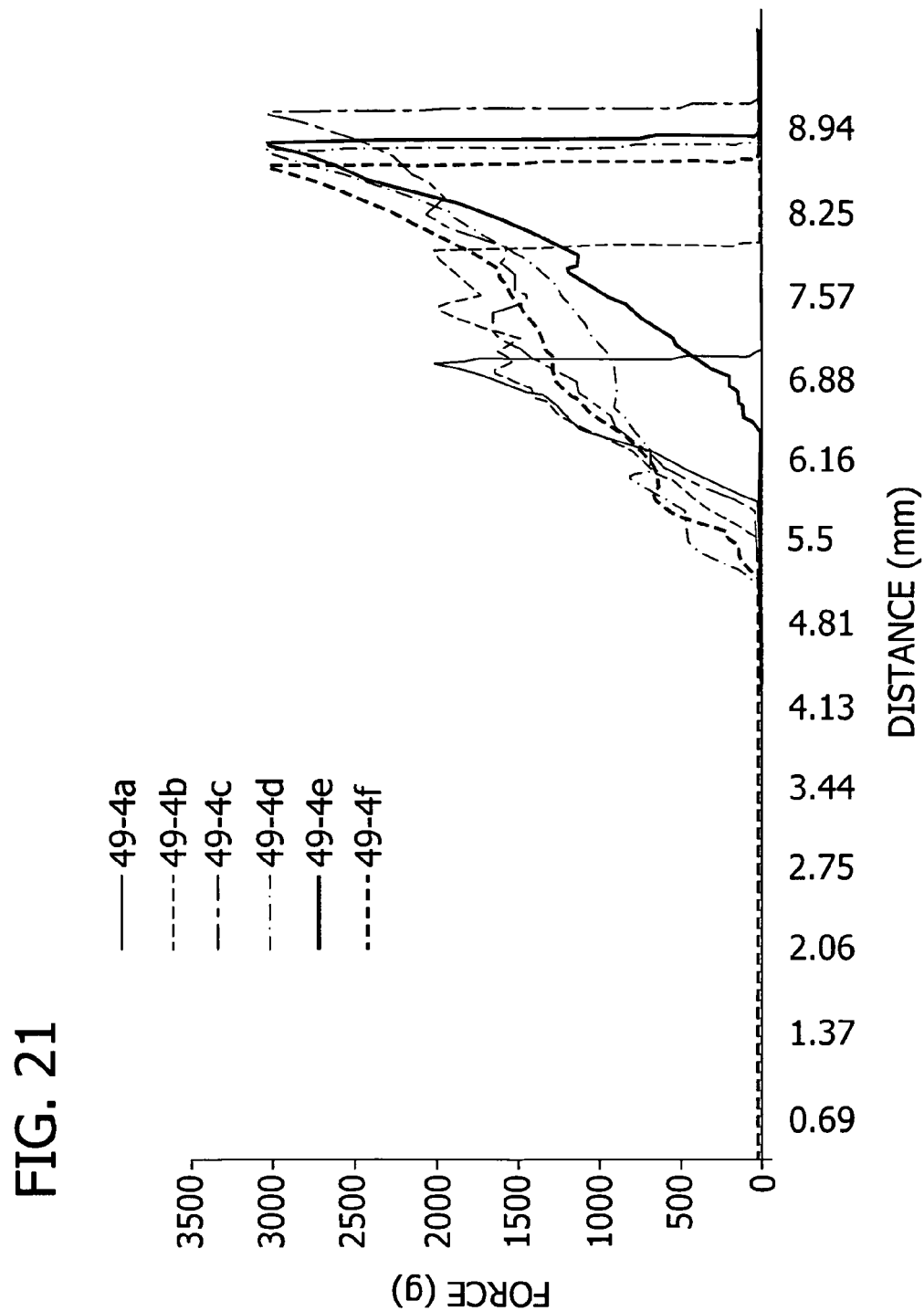
Figure 22:
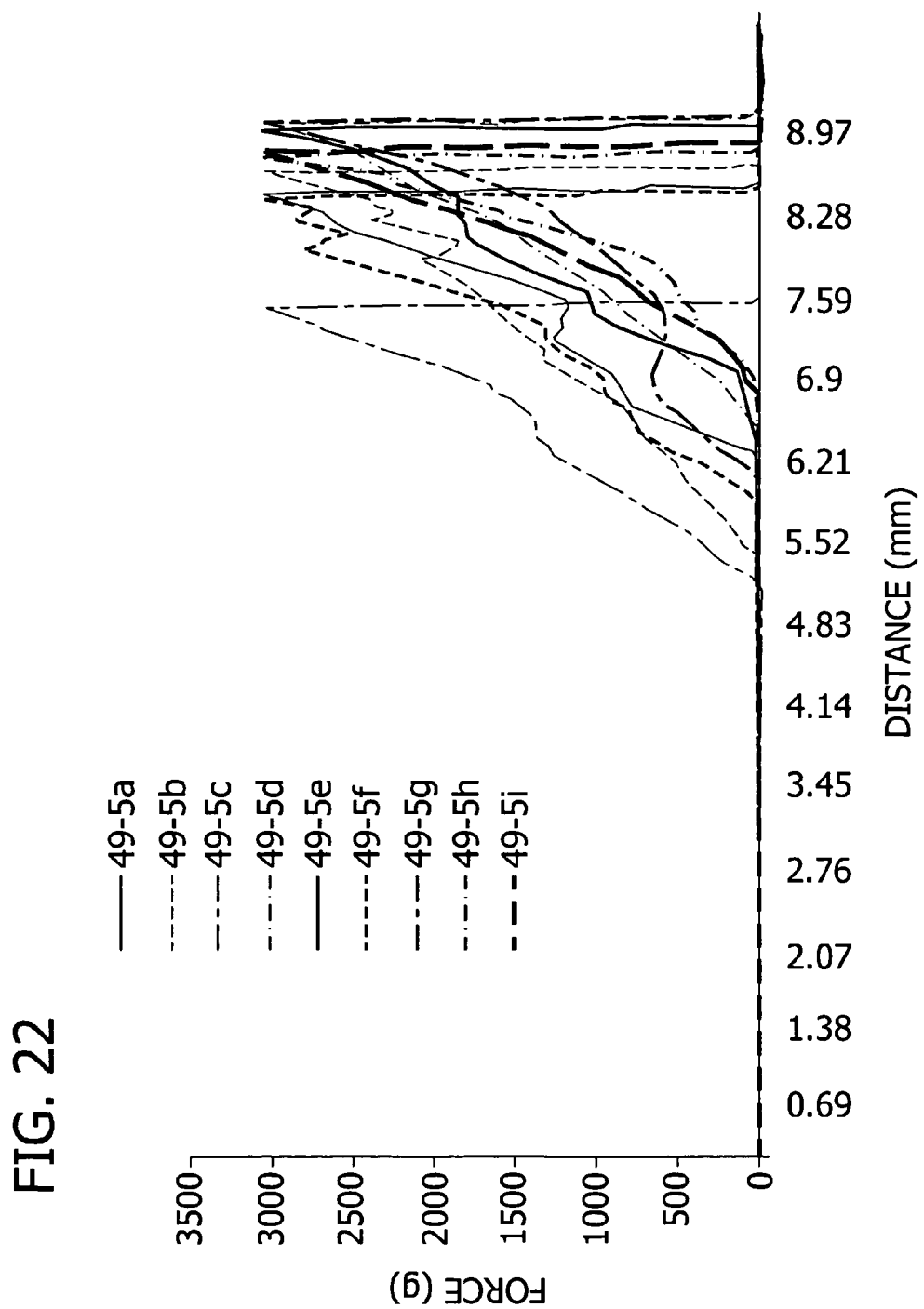
Figure 23:
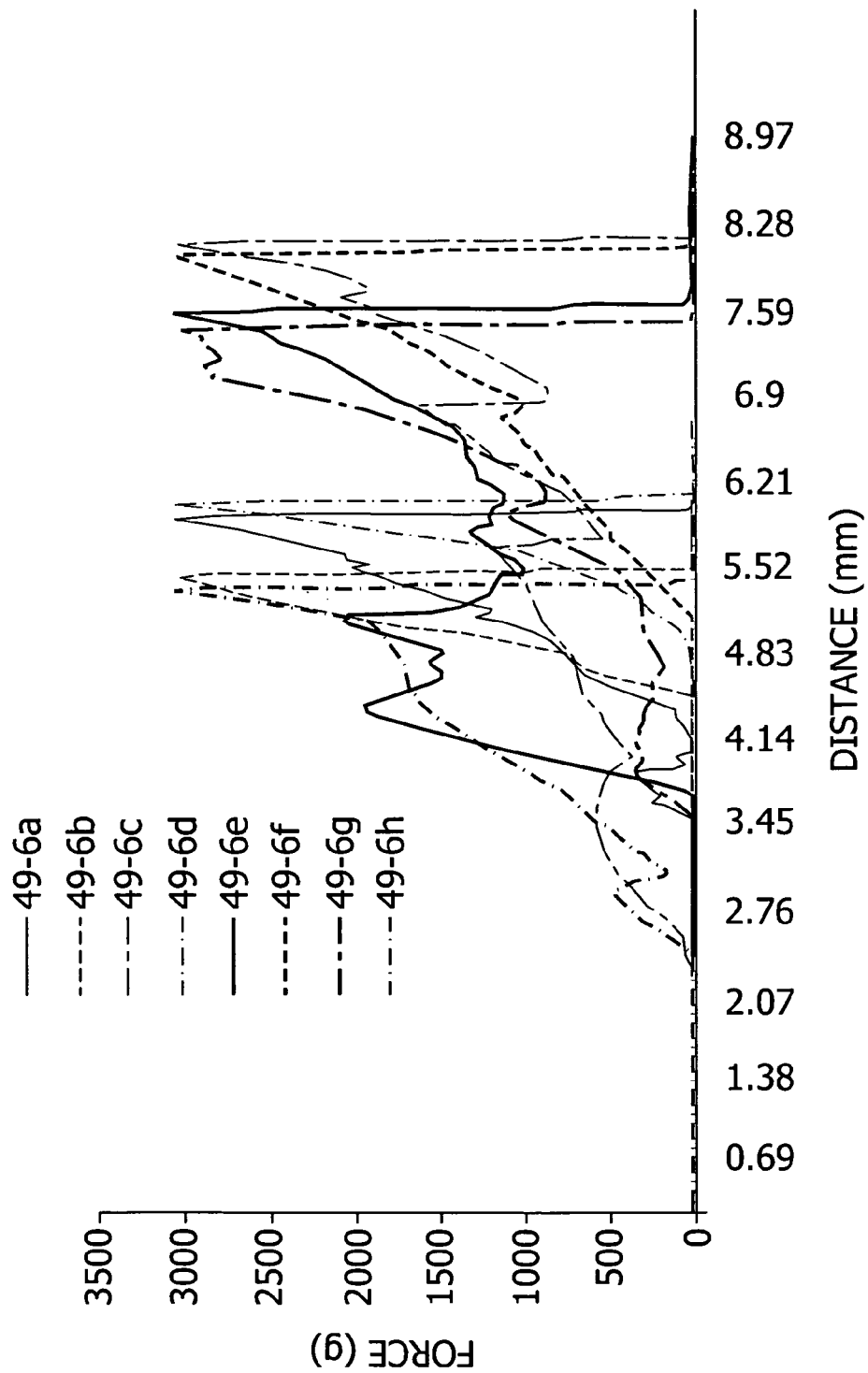
Figure 24:
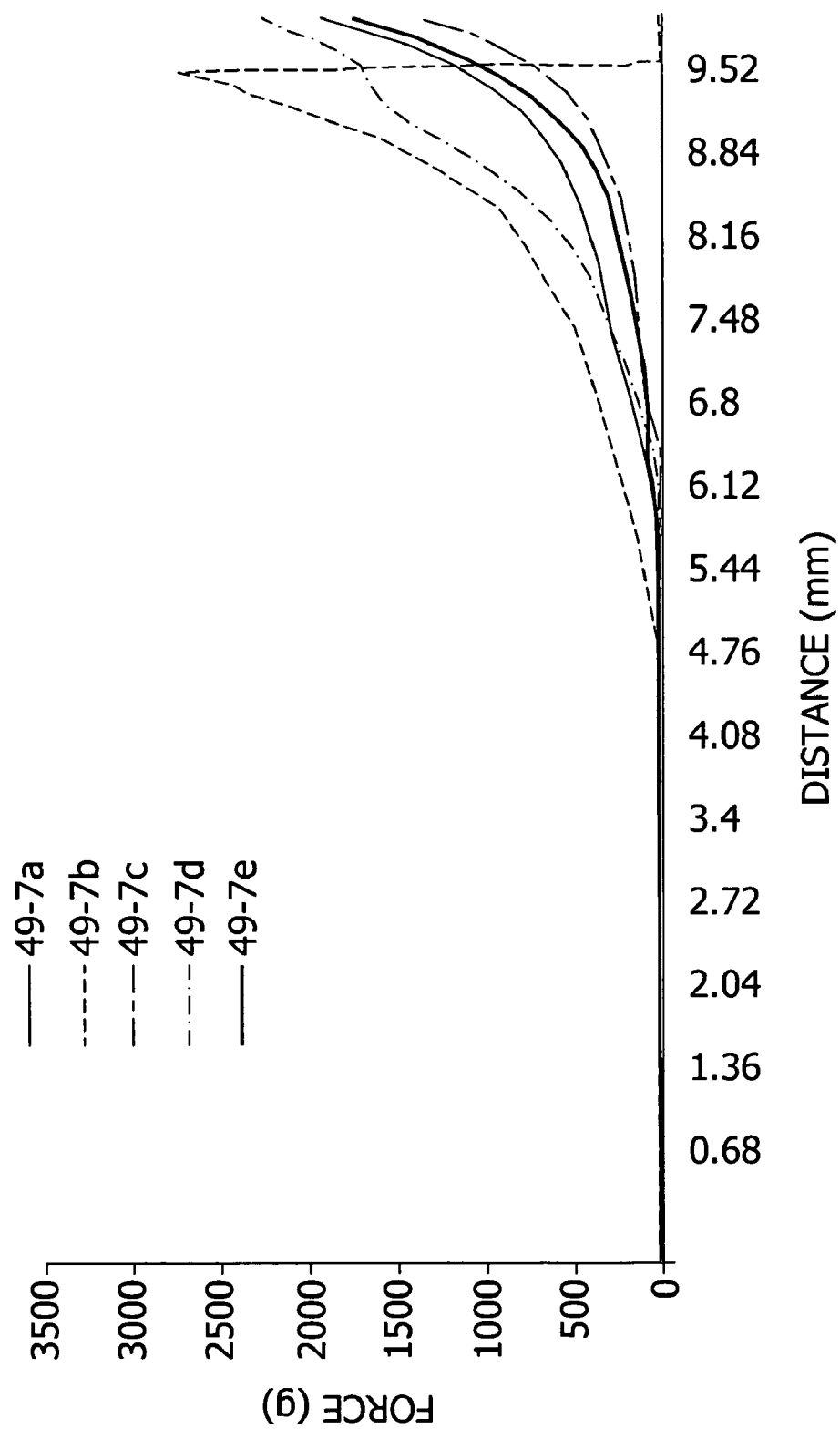

As shown in Table 5 and FIGS. 15-17, more force was required to crush samples of P6-D and P6-E than samples of P6-C. As such, it appears that by adding the additional chitosan or silica protective layers the particle strengths of the samples are increased.

EXAMPLE 17

In this Example, a microencapsulated heat delivery vehicle including a fugitive layer was produced.

To produce the microencapsulated heat delivery vehicle, calcium chloride (about 20 micrometers in particle size) was introduced into mineral oil to form a 25% (by weight) calcium chloride/75% (by weight) mineral oil composition that was mixed together thoroughly and had a resulting viscosity (25° C.) of about 300 centipoise. This composition was introduced dropwise from a separatory funnel into two liters of a sodium alginate solution (1% by weight in de-ionized water, 300 centipoise at 25° C.) and allowed to dwell in the solution for about 30 minutes under sufficient stirring to keep the drops formed upon addition into the sodium alginate solution separate. Most drops of the composition added were between about 4 millimeters in diameter and about 6 millimeters in diameter. After 30 minutes dwell time the formed microencapsulated beads were removed from the sodium alginate solution and rinsed three times with de-ionized water and cast to air-dry at room temperature overnight. Stable microencapsulated heat delivery vehicles were formed having a diameter of about 4 to about 6 millimeters.

Once the microencapsulated heat delivery vehicles were formed, the microencapsulated heat delivery vehicles were surrounded by a moisture protective layer. To produce the moisture protective layer for surrounding the microencapsulated heat delivery vehicles, the microencapsulated heat delivery vehicles were placed onto a Teflon coated pan and individually coated with a 30% (by weight) Saran F-310 in methyl ethyl ketone (MEK) solution using a pipette. The MEK was allowed to evaporate leaving the saran film as a moisture protective layer surrounding the microencapsulated heat delivery vehicles to form substantially fluid impervious microencapsulated heat delivery vehicles.

A polyvinyl alcohol solution was then used to produce a fugitive layer to surround the substantially fluid impervious microencapsulated heat delivery vehicles. To produce the fugitive layer, a 20% (by weight) solution of polyvinyl alcohol was prepared by hand stirring 20 grams of 87-89% hydrolyzed polyvinyl alcohol (available from Sigma-Aldrich Co., St. Louis, Mo.) into 80 grams of de-ionized water having a temperature of 70° C. The polyvinyl alcohol solution was then applied using a pipette to the substantially fluid impervious microencapsulated heat delivery vehicles. Two coats of the polyvinyl solution were applied to the substantially fluid impervious microencapsulated heat delivery vehicles. The substantially fluid impervious microencapsulated heat delivery vehicles coated with the polyvinyl alcohol solution were then dried in an oven at a temperature of 50° C. for 1 hour to produce the microencapsulated heat delivery vehicles including the fugitive layer.

EXAMPLE 18

In this example, a microencapsulated heat delivery vehicle including a fugitive layer was produced.

Substantially fluid impervious microencapsulated heat delivery vehicles were produced as in Example 17 above. A Ticacel® HV solution was then used to produce a fugitive layer to surround the substantially fluid impervious microencapsulated heat delivery vehicles. To produce the fugitive layer, a 1% (by weight) solution of Ticacel® HV was prepared by hand stirring 1 gram of Ticacel® HV powder (commercially available from TIC Gum, Belcamp, Md.) into 99 grams of de-ionized water at room temperature. The Ticacel® HV solution was then applied using a pipette to the substantially fluid impervious microencapsulated heat delivery vehicles. Two coats of the Ticacel® HV solution were applied to the substantially fluid impervious microencapsulated heat delivery vehicles. The substantially fluid impervious microencapsulated heat delivery vehicles coated with the Ticacel® HV solution were then dried in an oven at a temperature of 50° C. for 1 hour to produce the microencapsulated heat delivery vehicles including the fugitive layer.

EXAMPLE 19

In this example, a microencapsulated heat delivery vehicle including a fugitive layer was produced.

Substantially fluid impervious microencapsulated heat delivery vehicles were produced as in Example 17 above. A gum solution was then used to produce a fugitive layer to surround the substantially fluid impervious microencapsulated heat delivery vehicles. To produce the fugitive layer, a 10% (by weight) solution of Gum Arabic FT was prepared by hand stirring 10 grams of Gum Arabic FT (commercially available from TIC Gum, Belcamp, Md.) into 90 grams of de-ionized water at room temperature. The Gum Arabic FT solution was then applied using a pipette to the substantially fluid impervious microencapsulated heat delivery vehicles. To half of the substantially fluid impervious microencapsulated heat delivery vehicles, two coats of the Gum Arabic FT solution were applied. To the other half of the substantially fluid impervious microencapsulated heat delivery vehicles, four coats of the Gum Arabic FT solution were applied. The substantially fluid impervious microencapsulated heat delivery vehicles coated with the Gum Arabic FT solution were then dried in an oven at a temperature of 50° C. for 1 hour to produce the microencapsulated heat delivery vehicles including the fugitive layer.

EXAMPLE 20

In this example, a microencapsulated heat delivery vehicle including a fugitive layer was produced.

Substantially fluid impervious microencapsulated heat delivery vehicles were produced as in Example 17 above. A starch solution was then used to produce a fugitive layer to surround the substantially fluid impervious microencapsulated heat delivery vehicles. To produce the fugitive layer, a 30% (by weight) solution of PURE-COTE® B-792 starch was prepared by hand stirring 30 grams of PURE-COTE® B-792 starch (commercially available from Grain Processing Corporation, Muscatine, Iowa,) into 70 grams of de-ionized water having a temperature of 70° C. The B-792 starch solution was then applied using a pipette to the substantially fluid impervious microencapsulated heat delivery vehicles. Two coats of the B-792 starch solution were applied to the substantially fluid impervious microencapsulated heat delivery vehicles. The substantially fluid impervious microencapsulated heat delivery vehicles coated with the B-792 starch solution were then dried in an oven at a temperature of 50° C. for 1 hour to produce the microencapsulated heat delivery vehicles including the fugitive layer.

EXAMPLE 21

In this Example, the Gum Arabic FT fugitive shell made in Example 19 is removed from the substantially fluid impervious microencapsulated heat delivery vehicle.

To remove the fugitive shell, the substantially fluid impervious microencapsulated heat delivery vehicles including the fugitive shell were immersed in room temperature de-ionized water for 30 minutes. The fugitive shell appeared to dissolve in the water and the substantially fluid impervious microencapsulated heat delivery vehicle became visibly softer.

EXAMPLE 22

In this Example, the alginate microencapsulation method of the present disclosure was used to encapsulate a strawberry fragrance oil.

To produce the encapsulated strawberry fragrance oil, strawberry fragrance oil (commercially available from Intercontinental Fragrances, Houston, Tex.) was utilized to produce a milled (24 hours with one quarter inch zirconium grinding media) 10% (by weight) calcium chloride/89% (by weight) mineral oil (available from Penreco, Dickinson, Tex.)/1% (by weight) strawberry fragrance oil blend in a 250-gram jar to form a dispersion. Essentially all of the dispersion was then added dropwise to 200 grams of a 0.5% (by weight) aqueous sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads were cast onto a screen and rinsed twice with de-ionized water to wash away any unreacted alginate solution. The encapsulated beads were dried at 60° C. for 24 hours. The dried encapsulated beads were stable and had a diameter of less than 10,000 micrometers.

EXAMPLE 23

In this Example, the alginate microencapsulation method of the present disclosure was used to encapsulate an alcohol.

Ethanol was utilized to produce a milled (24 hours with one quarter inch zirconium grinding media) 10% (by weight) calcium chloride/89% (by weight) mineral oil (available from Penreco, Dickinson, Tex.)/1% (by weight) ethanol blend in a 250-gram jar to form a dispersion. Essentially all of the dispersion was then added dropwise to 200 grams of a 0.5% (by weight) aqueous sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads were cast onto a screen and rinsed twice with de-ionized water to wash away any unreacted alginate solution. The encapsulated beads were dried at 60° C. for 24 hours. The dried encapsulated beads were stable and had a diameter of less than 10,000 micrometers.

EXAMPLE 24

In this Example, the alginate microencapsulation method of the present disclosure was used to encapsulate a vegetable oil.

To produce the encapsulated vegetable oil, pure soybean vegetable oil (commercially available as Roundy's vegetable oil from Roundy's, Milwaukee, Wis.) was utilized to produce a milled (1.5 hours with one quarter inch zirconium grinding media) 10% (by weight) calcium chloride/90% (by weight) vegetable oil blend in an attritor mill to form a dispersion. The dispersion (100 grams) was then added dropwise to 2000 grams of a 0.5% (by weight) aqueous sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads were cast onto a screen and rinsed twice with de-ionized water to wash away any unreacted alginate solution. The encapsulated beads were dried at 60° C. for 24 hours. The dried encapsulated beads were stable and had a diameter size of less than 10,000 micrometers.

EXAMPLE 25

In this Example, the alginate microencapsulation method of the present disclosure was used to encapsulate yeast.

To produce the encapsulated yeast, 9 grams yeast (commercially available as Red Star® active dry yeast, Milwaukee, Wis.) was added to a 1-gram milled (24 hours with one quarter inch zirconium grinding media) 10% (by weight) calcium chloride/90% (by weight) mineral oil (available from Penreco, Dickinson, Tex.) blend in an attritor mill to form a dispersion. Essentially all of the dispersion was then added dropwise to 2000 grams of a 0.5% (by weight) aqueous sodium alginate solution including 0.05% (by weight)

sodium lauryl sulfate in a half-liter beaker. Specifically, the drops were added to the shoulder of a one inch diameter vortex and allowed to dwell for about 20 minutes before being removed. The resulting encapsulated beads were cast onto a screen and rinsed twice with de-ionized water to wash away any unreacted alginate solution. The encapsulated beads were dried at 60° C. for 24 hours. The dried encapsulated beads were stable and had a diameter of less than 10,000 micrometers.

EXAMPLE 26

In this Example, the alginate microencapsulation method of the present disclosure was used to encapsulate three different antioxidants.

The three types of antioxidants that were encapsulated included: Ethanox 330 (available from Albemale Corporation, Baton Rouge, La.), gallic acid, and methyl gallate. To encapsulate Ethanox 330, Ethanox 330 was utilized to produce a milled (24 hours with one quarter inch zirconium grinding media) 10% (by weight) calcium chloride/89% (by weight) mineral oil (available from Penreco, Dickinson, Tex.)/1% (by weight) Ethanox 330 blend in a 250-gram jar to form a dispersion. Essentially all of the dispersion was then added dropwise to 200 grams of a 0.5% (by weight) sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads are cast onto a screen to be rinsed twice with de-ionized water to wash away any unreacted alginate solution. The encapsulated beads are dried at 60° C. for 24 hours. The dried encapsulated beads were stable and had a diameter of less than 10,000 micrometers.

To encapsulate gallic acid and methyl gallate, the method described above for encapsulating Ethanox 330 was repeated for each antioxidant with the exception of replacing Ethanox 330 with either gallic acid or methyl gallate. Similar to the encapsulated Ethanox 330 above, the encapsulated beads containing either gallic acid or methyl gallate were stable and had a diameter of less than 10,000 micrometers.

EXAMPLE 27

In this Example, the alginate microencapsulation method of the present disclosure was used to encapsulate a vitamin.

Vitamin C (commercially available from Sigma-Aldrich Co., St. Louis, Mo.) was utilized to produce a milled (24 hours with one quarter inch zirconium grinding media) 10% (by weight) calcium chloride/89% (by weight) mineral oil (available from Penreco, Dickinson, Tex.)/1% (by weight) vitamin C blend in a 250-gram jar to form a dispersion. Essentially all of the dispersion was then added dropwise to 200 grams of a 0.5% (by weight) sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads are cast onto a screen to be rinsed twice with de-ionized water to wash away any unreacted alginate solution. The encapsulated beads are dried at 60° C. for 24 hours. The dried encapsulated beads had a diameter of less than 10,000 micrometers.

EXAMPLE 28

In this Example, the alginate microencapsulation method of the present disclosure was used to encapsulate a coloring agent.

The coloring agent encapsulated was oil soluble LCW D&C yellow 11 (available from Hilton Davis Chemical Company, Cincinnati, Ohio). To encapsulate LCW D&C yellow 11, LCW D&C yellow 11 was utilized to produce a milled (24 hours with one quarter inch zirconium grinding media) 10% (by weight) calcium chloride/89% (by weight) mineral oil (available from Penreco, Dickinson, Tex.)/1% (by weight) LCW D&C yellow 11 blend in a 250-gram jar to form a dispersion. Essentially all of the dispersion was then added dropwise to 200 grams of a 0.5% (by weight) sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads are cast onto a screen to be rinsed twice with de-ionized water to wash away any unreacted alginate solution. The encapsulated beads are dried at 60° C. for 24 hours. The dried encapsulated beads were stable and had a diameter of less than 10,000 micrometers.

EXAMPLE 29

In this Example, the alginate microencapsulation method of the present disclosure was used to encapsulate various polymers.

Two types of polymers, polyacrylic acid (commercially available from Sigma-Aldrich Co., St. Louis, Mo.) and polyvinyl butyral (available as Butvar® B-74 from Solutia, Inc., St. Louis, Mo.), were encapsulated. To encapsulate polyacrylic acid, polyacrylic acid was utilized to produce a milled (24 hours with one quarter inch zirconium grinding media) 10% (by weight) calcium chloride/89% (by weight) mineral oil (available from Penreco, Dickinson, Tex.)/1% (by weight) polyacrylic acid blend in a 250-gram jar to form a dispersion. Essentially all of the dispersion was then added dropwise to 200 grams of a 0.5% (by weight) sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads are cast onto a screen to be rinsed twice with de-ionized water to wash away any unreacted alginate solution. The encapsulated beads are dried at 60° C. for 24 hours. The dried encapsulated beads were stable and had a diameter of less than 10,000 micrometers.

To encapsulate polyvinyl butyral, the method as described above for encapsulating polyacrylic acid was repeated with the exception of replacing polyacrylic acid with polyvinyl butyral. Similar to the encapsulated polyacrylic acid above, the encapsulated beads containing polyvinyl butyral were stable and had a diameter of less than 10,000 micrometers.

EXAMPLE 30

In this Example, the alginate microencapsulation method of the present disclosure was used to encapsulate three different water soluble salts.

The three types of water soluble salts encapsulated were: zinc nitrate, copper nitrate, and zinc acetate (all commercially available from Sigma-Aldrich Co., St. Louis, Mo.). To encapsulate zinc nitrate, zinc nitrate was utilized to produce a milled (24 hours with one quarter inch zirconium grinding media) 10% (by weight) calcium chloride/89% (by weight) mineral oil (available from Penreco, Dickinson, Tex.)/1% (by weight) zinc nitrate blend in a 250-gram jar to form a dispersion. Essentially all of the dispersion was then added dropwise to 200 grams of a 0.5% (by weight) sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads are cast onto a screen to be rinsed twice with de-ionized water to wash away any unreacted alginate solution. The encapsulated beads are dried at 60° C. for 24 hours. The dried encapsulated beads were stable and had a diameter of less than 10,000 micrometers.

To encapsulate copper nitrate and zinc acetate, the method as described above for encapsulating zinc nitrate was repeated for each water soluble salt with the exception of replacing zinc nitrate with either copper nitrate or zinc acetate. Similar to the encapsulated zinc nitrate above, the encapsulated beads containing either the copper nitrate or zinc acetate were stable and had a diameter of less than 10,000 micrometers.

EXAMPLE 31

In this Example, the alginate microencapsulation method of the present disclosure was used to encapsulate calcium carbonate.

To encapsulate calcium carbonate, calcium carbonate (commercially available from Sigma-Aldrich Co., St. Louis, Mo.) was utilized to produce a milled (24 hours with one quarter inch zirconium grinding media) 10% (by weight) calcium chloride/89% (by weight) mineral oil (available from Penreco, Dickinson, Tex.)/1% (by weight) calcium carbonate blend in a 250-gram jar to form a dispersion. Essentially all of the dispersion was then added dropwise to 200 grams of a 0.5% (by weight) sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads are cast onto a screen to be rinsed twice with de-ionized water to wash away any unreacted alginate solution. The encapsulated beads are dried at 60° C. for 24 hours. The dried encapsulated beads were stable and had a diameter of less than 10,000 micrometers.

EXAMPLE 32

In this Example, the alginate microencapsulation method of the present disclosure was used to encapsulate two different metals.

The metals that were encapsulated were iron and silver (each commercially available from Sigma-Aldrich Co., St. Louis, Mo.). To encapsulate iron, iron was utilized to produce a milled (24 hours with one quarter inch zirconium grinding media) 10% (by weight) calcium chloride/89% (by weight) mineral oil (available from Penreco, Dickinson, Tex.)/1% (by weight) iron blend in a 250-gram jar to form a dispersion. Essentially all of the dispersion was then added dropwise to 200 grams of a 0.5% (by weight) sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads are cast onto a screen to be rinsed twice with de-ionized water to wash away any unreacted alginate solution. The encapsulated beads are dried at 60° C. for 24 hours. The encapsulated beads were stable and had a diameter of less than 10,000 micrometers.

To encapsulate silver, the method as described above for encapsulating iron was replaced with the exception of replacing iron with silver. Similar to the encapsulated iron above, the encapsulated beads containing silver were stable and had a diameter of less than 10,000 micrometers.

EXAMPLE 33

In this Example, the alginate microencapsulation method of the present disclosure was used to encapsulate Marathon® 150, which is a commercially available plasticizer.

To encapsulate Marathon® 150, Marathon® 150 (available from Marathon Ashland Petroleum LLC, Garyville, La.) was utilized to produce a milled (24 hours with one quarter inch zirconium grinding media) 10% (by weight) calcium chloride/89% (by weight) mineral oil (available from Penreco, Dickinson, Tex.)/1% (by weight) Marathon® 150 blend in a 250-gram jar to form a dispersion. Essentially all of the dispersion was then added dropwise to 200 grams of a 0.5% (by weight) sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads are cast onto a screen to be rinsed twice with de-ionized water to wash away any unreacted alginate solution. The encapsulated beads are dried at 60° C. for 24 hours. The dried encapsulated beads were stable and had a diameter of less than 10,000 micrometers.

EXAMPLE 34

In this Example, the alginate microencapsulation method of the present disclosure was used to encapsulate various acids.

The acids that were encapsulated included: boric acid, citric acid, succinic acid, salicylic acid, and benzoic acid (all commercially available from Sigma-Aldrich Co., St. Louis, Mo.). To encapsulate boric acid, boric acid was utilized to produce a milled (24 hours with one quarter inch zirconium grinding media) 10% (by weight) calcium chloride/89% (by weight) mineral oil (available from Penreco, Dickinson, Tex.)/1% (by weight) boric acid blend in a 250-gram jar to form a dispersion. Essentially all of the dispersion was then added dropwise to 200 grams of a 0.5% (by weight) sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads are cast onto a screen to be rinsed twice with de-ionized water to wash away any unreacted alginate solution. The encapsulated beads are dried at 60° C. for 24 hours. The dried encapsulated beads were stable and had a diameter of less than 10,000 micrometers.

To encapsulate the other four acids, the method as described above for encapsulating boric acid was repeated for each of the other four acids with the exception of replacing boric acid with one of the other four acids. Similar to the encapsulated boric acid above, the encapsulated beads containing the other acids were stable and had a diameter of less than 10,000 micrometers.

EXAMPLE 35

In this Example, the alginate microencapsulation method of the present disclosure was used to encapsulate ammonium hydroxide.

To encapsulate ammonium hydroxide, ammonium hydroxide (commercially available from Sigma-Aldrich Co., St. Louis, Mo.) was utilized to produce a milled (24 hours with one quarter inch zirconium grinding media) 10% (by weight) calcium chloride/89% (by weight) mineral oil (available from Penreco, Dickinson, Tex.)/1% (by weight) ammonium hydroxide blend in a 250-gram jar to form a dispersion. Essentially all of the dispersion was then added dropwise to 200 grams of a 0.5% (by weight) sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads are cast onto a screen to be rinsed twice with de-ionized water to wash away any unreacted alginate solution. The encapsulated beads are dried at 60° C. for 24 hours. The dried encapsulated beads were stable and had a diameter of less than 10,000 micrometers.

EXAMPLE 36

In this Example, the alginate microencapsulation method of the present disclosure was used to encapsulate various pigments.

Three types of pigments, titanium dioxide (commercially available from DuPont Co., Edge Moor, Del.), zinc oxide (commercially available from Sigma-Aldrich Co., St. Louis, Mo.), and magnesium oxide (commercially available from Sigma-Aldrich Co., St. Louis, Mo.), were encapsulated. To encapsulate titanium dioxide, titanium dioxide was utilized to produce a milled (24 hours with one quarter inch zirconium grinding media) 10% (by weight) calcium chloride/89% (by weight) mineral oil (available from Penreco, Dickinson, Tex.)/1% (by weight) titanium dioxide blend in a 250-gram jar to form a dispersion. Essentially all of the dispersion was then added dropwise to 200 grams of a 0.5% (by weight) sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads are cast onto a screen to be rinsed twice with de-ionized water to wash away any unreacted alginate solution. The encapsulated beads are dried at 60° C. for 24 hours. The dried encapsulated beads were stable and had a diameter of less than 10,000 micrometers.

To encapsulate zinc oxide or magnesium oxide, the method as described above for encapsulating titanium dioxide was repeated with the exception of replacing titanium dioxide with either zinc oxide or magnesium oxide. Similar to the encapsulated titanium dioxide above, the encapsulated beads containing either zinc oxide or magnesium oxide were stable and had a diameter of less than 10,000 micrometers.

EXAMPLE 37

In this Example, the alginate microencapsulation method of the present disclosure was used to encapsulate various fuels.

Three types of fuels, toluene (commercially available from Hawkins Chemical, Minneapolis, Minn., heptane (commercially available from Hawkins Chemical, Minneapolis, Minn.), and naptha (commercially available from Phipps Products Corporation, Boston, Mass.), were encapsulated. To encapsulate toluene, toluene was utilized to produce a milled (24 hours with one quarter inch zirconium grinding media) 10% (by weight) calcium chloride/89% (by weight) mineral oil (available from Penreco, Dickinson, Tex.)/1% (by weight) toluene blend in a 250-gram jar to form a dispersion. Essentially all of the dispersion was then added dropwise to 200 grams of a 0.5% (by weight) sodium alginate solution including 0.05% (by weight) sodium lauryl sulfate in a half-liter beaker. Specifically, the drops were added to the shoulder of a one inch diameter vortex and allowed to dwell for about 20 minutes before being removed. The resulting encapsulated beads are cast onto a screen to be rinsed twice with de-ionized water to wash away any unreacted alginate solution. The encapsulated beads are dried at 60° C. for 24 hours. The dried encapsulated beads were stable and had a diameter of less than 10,000 micrometers.

To encapsulate the heptane or naptha, the method as described above for encapsulating toluene was repeated with the exception of replacing toluene with either heptane or naptha. Similar to the encapsulated toluene above, the encapsulated beads containing either heptane or naptha were stable and had a diameter of less than 10,000 micrometers.

EXAMPLE 38

In this Example, a self-warming wet wipe including microencapsulated heat delivery vehicles was produced according to the present disclosure. The temperature increase in the wet wipe upon activation of the contents of the microencapsulated heat delivery vehicles was then analyzed.

To produce the self-warming wet wipe, two layers of a coform basesheet, each made of 30% (by weight) polypropylene fibers and 70% (by weight) wood pulp fibers and having a basis weight of 30 grams per square meter, were heat sealed together on three sides to form a pouch (2"×2"). Microencapsulated heat delivery vehicles were made by first producing the microencapsulated heat delivery vehicles in accordance with a method described above and then 2.24 grams of the microencapsulated heat delivery vehicles were placed inside the pouch and the fourth side of the pouch was heat sealed to form a wipe.

To produce the microencapsulated heat delivery vehicles, anhydrous magnesium chloride (about 20 micrometers in diameter) was introduced into mineral oil to form a 25% (by weight) magnesium chloride/75% (by weight) mineral oil composition that was mixed together thoroughly and had a resulting viscosity (25° C.) of about 300 centipoise. This composition was introduced dropwise from a separatory funnel into two liters of a sodium alginate solution (1% by weight in de-ionized water, 300 centipoise at 25° C.) and allowed to dwell in the solution for about 30 minutes under sufficient stirring to keep the drops formed upon addition into the sodium alginate solution separate. Most drops of the composition added were about 3 millimeters in diameter. After 30 minutes dwell time the formed microencapsulated beads were removed from the sodium alginate solution and rinsed three times with de-ionized water and cast to air-dry at room temperature overnight. Stable microencapsulated heat delivery vehicles were formed having a diameter of about 3 millimeters.

The wipe containing the microencapsulated heat delivery vehicles was then wetted with 0.7 grams wetting solution using a spray bottle. The wetting solution comprised the following components: about 98.18% (by weight) water; about 0.6% (by weight) potassium laureth phosphate; about 0.30% (by weight) glycerin; about 0.30% (by weight) polysorbate 20; about 0.20% (by weight) tetrasodium EDTA; about 0.20% (by weight) DMDM hydrantoin; about 0.15% (by weight) methylparaben; about 0.07% (by weight) malic acid; about 0.001% (by weight) aloe barbadensis; and about 0.001% (by weight) tocopheryl acetate.

Once the wet wipe was produced, the temperature of the wet wipe was measured by folding the wipe in half and inserting a Type K thermocouple (available from VWR International, West Chester, Pa.) into the center of the folded wipe. The wipe was then introduced into a standard polyethylene bag, which was then laid onto six layers of paper toweling (commercially available as Scott Brand, Kimberly-Clark Worldwide, Inc., Neenah, Wis.). The temperature of the wipe was measured to be 29.9° C.

The microencapsulated heat delivery vehicles were then broken using a Coorstek 60314 pestle (available from CoorsTek, Golden, Colo.). The broken shells of the microencapsulated heat delivery vehicles remained inside of the wipe. As the microencapsulated heat delivery vehicles were crushed and their contents exposed to the wetting solution, the wet wipe began warming. The warming of the wet wipe was analyzed by using a digital thermometer (available from VWR International, West Chester, Pa.), which recorded at a 3 second interval. The temperature was recorded for 90 seconds, starting from the time the microencapsulated heat delivery vehicles were crushed. The temperature of the wet wipe increased to a temperature of 41.2° C.

EXAMPLE 39

In this Example, samples of pan coated alginate microencapsulated heat delivery vehicles having fugitive shell layers made from various materials were produced and analyzed for particle strength. Control samples of pan coated alginate microencapsulated heat delivery vehicles without fugitive shell layers were also produced and analyzed for particle strength.

Nine control samples of 49-1 pan coated alginate microencapsulated heat delivery vehicle without fugitive shell layers were produced using the method of Example 12. Nine samples of 49-2 pan coated alginate microencapsulated heat delivery vehicle having a fugitive shell layer made from Ticacel® HV (commercially available from TIC Gum, Belcamp, Md.) were produced using the method of Example 18. Six samples of 49-4 pan coated alginate microencapsulated heat delivery vehicle having a fugitive shell layer made from PURE-COTE® B-792 starch (commercially available from Grain Processing Corporation, Muscatine, Iowa) were produced using the method of Example 20. Nine samples of 49-5 pan coated alginate microencapsulated heat delivery vehicle having a fugitive shell layer made from polyvinyl alcohol (commercially available from Sigma-Aldrich Co., St. Louis, Mo.) were produced using the method of Example 17. Seven samples of 49-3 pan coated alginate microencapsulated heat delivery vehicle having a fugitive shell layer made from Gum Arabic FT (commercially available from TIC Gum, Belcamp, Md.) were produced using the method of Example 19. Eight samples of 49-6 pan coated alginate microencapsulated heat delivery vehicle having a fugitive shell layer made from Gum Arabic FT were produced using the same method as used to produce the 49-3 samples except that four coats of Gum Arabic FT were applied. Five samples of 49-7 pan coated alginate microencapsulated heat delivery vehicle having a fugitive shell layer made from Gum Arabic FT were produced using the same method as used to produce the 49-3 samples and then the Gum Arabic FT was removed using the method as set forth in Example 21.

To test particle strength, a TA Texture Analyzer (Software Version 1.22) (available from Texture Technologies Corporation, Scarsdale, N.Y.) was used. Specifically, a single particle of each sample was independently placed on a polycarbonate plate and force measurements were made using a one-quarter inch to one inch diameter flat probe, moving at a rate of about 0.25 millimeter/second to about 5.0 millimeters/second. As the force load was applied by the probe, the particle deformed until it cracked or collapsed. Generally, the deformation of the particle continues until the applied force increases exponentially, indicating that the shell of the particle has been ruptured. The results of the measurements were averaged for each type of sample and are shown in Table 6 and FIGS. 18-24.

TABLE 6

| Pan Coated Alginate Microencapsulated Heat Delivery Vehicle Sample | Averaged Force (grams) required to rupture sample particle |
| --- | --- |
| 49-1 | 1123 |
| 49-2 | 1274 |
| 49-3 | 707 |
| 49-4 | 1197 |
| 49-5 | 1131 |
| 49-6 | 849 |
| 49-7 | Not Detectable |

As shown in Table 6 and FIGS. 18-24, on average, more force was required to crush samples of 49-2, 49-4, and 49-5 than samples of 49-1. Specifically, the samples of 49-2, which have a fugitive shell layer made of Ticacel® HV Powder, required the greatest force to rupture, indicating that Ticacel® HV Powder provides the greatest protection among the materials in the Example against rupturing. The samples of 49-4 and 49-5, which have fugitive shell layers made of starch and polyvinyl alcohol, respectively, also provide improved protection against rupturing. The samples having fugitive shell layers made of Gum Arabic FT were more easily ruptured.

Additionally, as shown in FIGS. 18-24, samples of 49-2, 49-4, and 49-5 did not appear to deform as much as samples of 49-1, 49-3, and 49-6, as indicated by the steeper slope of the force curves.

EXAMPLE 40

In this Example, the biocide, polyhexamethylene biguanide, was evaluated at elevated temperatures to determine its efficacy.

This Example utilized 1.5-milliliter tubes containing a 1-milliliter blend of phosphate-buffered saline (pH 7.2) and 5% (w/v) bovine serum albumin soil. The tubes were placed in electric heat blocks set for 22° C., 30° C., 40° C. and 50° C., respectively. The tubes remained in the electric heat blocks for approximately 10 minutes.

After 10 minutes, 0.005% (by weight) active polyhexamehtylene biguanide (PHMB) (commercially available as Cosmocil® CQ from Arch Biocides, Inc., United Kingdom) was added to two tubes at each temperature level. Duplicate tubes without PHMB at each temperature were also made.

The tubes were then vortexed and Methicillin-resistant *Staphylococcus aureus* (approximately $1 \times 10^5$ colony forming units (CFU)) was then added to each tube. All of the tubes were then placed back into the heat blocks at their respective temperatures.

Following a 10-minute contact time, 0.1 milliliters of each sample was transferred to 0.9 milliliters letheen broth to neutralize the PHMB activity. The letheen samples were then plated in duplicate on Tryptic Soy agar plates using a WASP2 spiral plater (commercially available from Don Whitley Scientific, Ltd., Yorkshire, United Kingdom). The plates were inverted and incubated at 37±2° C. for 48 hours.

After 48 hours, the plates were evaluated using a total plate count to determine the biocidal efficacy of each sample. The results are shown in Table 7.

TABLE 7

| Heat blocks @ various temperatures (n = 2) | Total CFU Recovered | |
|---|---|---|
| | MRSA | LOG$_{10}$ Reduction |
| 22° C. | 5.6 | 2.1 |
| 22° C.; 0.005% PHMB | 3.5 | |
| 30° C. | 5.7 | 2.8 |
| 30° C.; 0.005% PHMB | 2.9 | |
| 40° C. | 5.6 | 3.5 |
| 40° C.; 0.005% PHMB | 2.1 | |
| 50° C. | 5.5 | >3.5 |
| 50° C.; 0.005% PHMB | <2 | |

As shown in Table 7, greater efficacy of the 0.005% (by weight) active PHMB was observed as the temperature increased. Specifically, a greater than 1.4 LOG$_{10}$ difference in efficacy was observed between experiments conducted at 22° C. as compared to those conduced at 50° C.

EXAMPLE 41

In this Example, magnesium chloride was evaluated for its ability to increase biocidal efficacy when used in combination with the biocide, polyhexamethylene biguanide.

A 1.5-milliliter tube was prepared using magnesium chloride in water.

Two control samples were also prepared. One control sample was filled with 0.850 milliliters magnesium chloride. A second control sample was prepared by introducing 0.850 milliliters sterile water.

A biocide agent, polyhexamethylene biguanide (PHMB), which has a final concentration of 0.00025% was then introduced into one tube comprising magnesium chloride and water and to the one control tube containing solely water. The tubes were then vortexed until an increase in temperature was observed.

0.05 milliliters of 1×10$^7$ CFU/milliliter culture of *Staphylococcus aureus* was added to each tube. After a 15-minute contact time, 0.1 milliliters of each tube was transferred into 0.9 milliliters letheen broth. To the broth, 10 milligrams/milliliter sodium thiosulfate was also added. The tubes were again vortexed. After vortexing, 0.1 milliliters of each tube was plated on Tryptic soy agar plates. The plates were inverted and incubated at 37° C. for 24 hours. An inoculum control plate was also plated to determine the concentration of the inoculum After 24 hours, the plates were evaluated using a total plate count to determine the biocidal efficacy of each sample. The results are shown in Table 8.

TABLE 8

| PHMB Concentration (%) | Magnesium Chloride Concentration (%) | LOG$_{10}$ recovered |
|---|---|---|
| 0.00025 | 0 | 4.8 |
| 0 | 50 | 1.9 |
| 0.00025 | 50 | 1.0 |

As shown in Table 8, the tube comprising magnesium chloride in combination with PHMB inhibited *Staphylococcus aureus* better than the other tubes.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A wet wipe comprising a fibrous sheet material, a wetting solution, a microencapsulated heat delivery vehicle, and a first phase change material, wherein the first phase change material has a particle size of from about 300 to about 500 micrometers, the microencapsulated heat delivery vehicle comprising an encapsulation layer that surrounds a core composition, wherein the core composition comprises a matrix material, an encapsulating activator, and a heating agent, the heating agent being surrounded by a hydrophobic wax material.

2. The wet wipe as set forth in claim 1 wherein first phase change material has a melting point of from about 22° C. to about 50° C.

3. The wet wipe as set forth in claim 2 wherein the first phase change material is selected from the group consisting of n-Tetracosane, n-Tricosane, n-Docosane, n-Heneicosane, n-Eicosane, n-Nonadecane, n-Octadecane, n-Heptadecane, and combinations thereof.

4. The wet wipe as set forth in claim 1 further comprising a second phase change material, wherein the second phase change material is different than the first phase change material.

5. The wet wipe as set forth in claim 4 wherein the second phase change material has a melting point of from about 50° C. to about 65° C.

6. The wet wipe as set forth in claim 4 wherein the second phase change material is selected from the group consisting of n-Tetracosane, n-Tricosane, n-Docosane, n-Heneicosane, n-Eicosane, n-Nonadecane, n-Octadecane, n-Heptadecane, and combinations thereof.

7. The wet wipe as set forth in claim 1 wherein the first phase change material particle is microencapsulated.

8. A dry wipe comprising a fibrous sheet material, a microencapsulated heat delivery vehicle, and a first phase change material, wherein the first phase change material has a particle size of from about 300 to about 500 micrometers, the microencapsulated heat delivery vehicle comprising an encapsulation layer that surrounds a core composition, wherein the core composition comprises a matrix material, an encapsulating activator, and a heating agent, the heating agent being surrounded by a hydrophobic wax material.

9. The dry wipe as set forth in claim 8 wherein first phase change material has a melting point of from about 22° C. to about 50° C.

10. The dry wipe as set forth in claim 9 wherein the first phase change material is selected from the group consisting of n-Tetracosane, n-Tricosane, n-Docosane, n-Heneicosane, n-Eicosane, n-Nonadecane, n-Octadecane, n-Heptadecane, and combinations thereof.

11. The dry wipe as set forth in claim 8 further comprising a second phase change material, wherein the second phase change material is different than the first phase change material.

12. The dry wipe as set forth in claim 11 wherein the second phase change material has a melting point of from about 50° C. to about 65° C.

13. The dry wipe as set forth in claim 11 wherein the second phase change material is selected from the group consisting of n-Tetracosane, n-Tricosane, n-Docosane, n-Heneicosane, n-Eicosane, n-Nonadecane, n-Octadecane, n-Heptadecane, and combinations thereof.

14. The dry wipe as set forth in claim 8 wherein the first phase change material particle is microencapsulated.

* * * * *